US008834869B2

(12) United States Patent
Pakola et al.

(10) Patent No.: US 8,834,869 B2
(45) Date of Patent: *Sep. 16, 2014

(54) PHARMACOLOGICAL VITREOLYSIS

(71) Applicant: ThromboGenics NV, Leuven (BE)

(72) Inventors: Steve Pakola, Sleepy Hollow, NY (US); Marc De Smet, Amstelveen (NL)

(73) Assignee: ThromboGenics NV, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/689,025

(22) Filed: Nov. 29, 2012

(65) Prior Publication Data

US 2013/0195887 A1  Aug. 1, 2013

Related U.S. Application Data

(63) Continuation of application No. 12/156,907, filed on Jun. 5, 2008, now Pat. No. 8,460,655, which is a continuation of application No. 10/729,475, filed on Dec. 5, 2003, now Pat. No. 7,547,435.

(30) Foreign Application Priority Data

Dec. 6, 2002 (GB) .................................. 0228409.9

(51) Int. Cl.
A61K 38/48 (2006.01)
A61K 38/43 (2006.01)
A61M 35/00 (2006.01)
A61K 45/06 (2006.01)

(52) U.S. Cl.
CPC ............... *A61K 38/484* (2013.01); *A61K 45/06* (2013.01)
USPC ..................... 424/94.64; 424/94.1; 424/94.63

(58) Field of Classification Search
CPC ........... A61K 38/484; A61K 2300/00; A61K 9/0048; C12N 9/6435; C12N 9/50; C12Y 304/21007
USPC .................................. 424/94.64, 94.63, 94.1
See application file for complete search history.

(56) References Cited

U.S. PATENT DOCUMENTS

| 2,624,691 | A | 1/1953 | Loomis |
|---|---|---|---|
| 3,234,106 | A | 2/1966 | Hink |
| 3,950,513 | A | 4/1976 | Jensen |
| 4,462,980 | A | 7/1984 | Diedrichsen et al. |
| 4,774,087 | A | 9/1988 | Wu et al. |
| 4,820,516 | A | 4/1989 | Sawyer et al. |
| 5,288,485 | A | 2/1994 | Kikuta et al. |
| 5,292,509 | A | 3/1994 | Hageman |
| 5,304,118 | A | 4/1994 | Trese et al. |
| 5,637,299 | A | 6/1997 | McDonagh et al. |
| 5,722,428 | A | 3/1998 | Kaplan et al. |
| 5,866,120 | A | 2/1999 | Karageozian et al. |
| 6,051,698 | A | 4/2000 | Janjic et al. |
| 6,183,692 | B1 | 2/2001 | Trese et al. |
| 6,207,066 | B1 | 3/2001 | Trese et al. |
| 6,355,243 | B1 | 3/2002 | Novokhatny et al. |
| 6,378,526 | B1 | 4/2002 | Bowman et al. |
| 6,462,071 | B1 | 10/2002 | Castillejos |
| 6,585,972 | B2 | 7/2003 | Peyman |
| 6,596,725 | B2 | 7/2003 | Peterson et al. |
| 6,610,292 | B2 | 8/2003 | Karageozian et al. |
| 6,733,750 | B1 | 5/2004 | Peyman |
| 6,787,135 | B2 | 9/2004 | Trese et al. |
| 7,547,435 | B2 | 6/2009 | Pakola et al. |
| 7,803,368 | B2 | 9/2010 | Pakola et al. |
| 7,867,489 | B2 | 1/2011 | Pakola et al. |
| 7,914,783 | B2 | 3/2011 | Pakola et al. |
| 8,383,105 | B2 | 2/2013 | Pakola et al. |
| 8,460,655 | B2 | 6/2013 | Pakola et al. |
| 2002/0042652 | A1 | 4/2002 | Peyman |
| 2002/0139378 | A1 | 10/2002 | Trese et al. |
| 2002/0192794 | A1 | 12/2002 | Dadd et al. |
| 2003/0012778 | A1* | 1/2003 | Zimmerman et al. ...... 424/94.64 |
| 2003/0026798 | A1 | 2/2003 | Zimmerman et al. |
| 2003/0082159 | A1* | 5/2003 | Appukuttan et al. ...... 424/93.21 |
| 2003/0113313 | A1 | 6/2003 | Peyman |
| 2003/0147877 | A1 | 8/2003 | Trese et al. |
| 2003/0175263 | A1 | 9/2003 | Trese et al. |
| 2004/0081643 | A1 | 4/2004 | Peyman |

(Continued)

FOREIGN PATENT DOCUMENTS

| GB | 985498 | 3/1965 |
|---|---|---|
| WO | WO-9852602 A1 | 11/1998 |

(Continued)

OTHER PUBLICATIONS

Macular degeneration. University of Maryland Medical Center. downloaded on Aug. 23, 2013 from umm.edu/health/medical/altmed/condition/macular-degeneration. p. 1-8.*

(Continued)

Primary Examiner — Taeyoon Kim
(74) Attorney, Agent, or Firm — Wilmer Cutler Pickering Hale and Dorr LLP

(57) ABSTRACT

A method of treating or preventing a disorder, or a complication of a disorder, of an eye of a subject comprising contacting a vitreous and/or aqueous humor with a composition comprising a truncated form of plasmin comprising a catalytic domain of plasmin (TPCD). TPCDs include, but are not limited to, miniplasmin, microplasmin and derivatives and variants thereof. The methods of the invention can be used to reduce the viscosity of the vitreous, liquefy the vitreous, induce posterior vitreous detachment, reduce hemorrhagic blood from the eye, clear or reduce materials toxic to the eye, clear or reduce intraocular foreign substances from the eye, increase diffusion of a composition administered to an eye, reduce extraretinal neovascularization and any combinations thereof. The method can be used in the absence of, or as an adjunct to, vitrectomy.

32 Claims, 19 Drawing Sheets

(56) References Cited

U.S. PATENT DOCUMENTS

| | | |
|---|---|---|
| 2006/0257391 A1 | 11/2006 | Bartels et al. |
| 2007/0128182 A1 | 6/2007 | Bartels et al. |
| 2007/0141043 A1 | 6/2007 | Bartels et al. |
| 2007/0212358 A1 | 9/2007 | Bartels |
| 2008/0008698 A1 | 1/2008 | Bartels et al. |
| 2008/0050356 A1 | 2/2008 | Pakola et al. |
| 2008/0095753 A1 | 4/2008 | Pakola et al. |
| 2009/0074739 A1 | 3/2009 | Pakola et al. |
| 2009/0081187 A1 | 3/2009 | Pakola et al. |
| 2013/0195887 A1 | 8/2013 | Pakola et al. |
| 2013/0202613 A1 | 8/2013 | Pakola et al. |

FOREIGN PATENT DOCUMENTS

| | | |
|---|---|---|
| WO | WO-01/34797 | 5/2001 |
| WO | WO-02/50290 | 6/2002 |
| WO | WO-02/102837 | 12/2002 |
| WO | WO-2004/045558 A2 | 6/2004 |
| WO | WO-2004/052228 | 6/2004 |

OTHER PUBLICATIONS

Cataract. American optometric association. downloaded on Aug. 23, 2013 from www.aoa.org/patients-and-public/eye-and-vision-problems/glossary-of-eye-and-vision-conditions/cataract p. 1-5.*

What can I do to prevent glaucoma? Glaucom Research Foundcation. downloaded on Aug. 23, 2013 from www.glaucoma.org/gleams/what-can-i-do-prevent-glaucoma.php p. 1-2.*

Asami T, Terasaki H, Kachi S, Nakamura M, Yamamura K, Nabeshima T, and Miyake Y, Ultrastructure of internal limiting membrane removed during plasmin-assisted vitrectomy from eyes with diabetic macular edema. Ophthalmology, 111, 231-237, Feb. 2004.

Azzolini C, D'Angelo A, Maestranzi G, Codenotti M, Della Valle PPM, and Brancato R, Intrasurgical plasmin enzyme in diabetic macular edema. Am J Ophthalmol, 139, 949-950, May 2005.

Azzolini C, D'Angelo A, Maestranzi G, Codenotti M, Della VP, Prati M, and Brancato R, Intrasurgical plasmin enzyme in diabetic macular edema. Am J Ophthalmol, 138, 560-566, Oct. 2004.

Berman et al. "Evidence for a role of the plasminogen activator-plasmin system in corneal ulceration." Invest Ophthalmol Vis Sci., 19(10):1204-21 (Oct. 1980).

Bhisitkul RB, Anticipation for enzymatic vitreolysis. Br J Ophthalmol, 85, 1-2, Jan. 2001.

Bishop PN, Structural macromolecules and supramolecular organisation of the vitreous gel. Prog Retin Eye Res, 19, 323-344, May 2000.

Castellino and Powell, "Human plasminogen," in *Methods Enzymology*, vol. 80: *Proteolytic Enzymes, Part C*, Ed. Laszlo Lorand, pp. 365-378, 1981.

Castellino et al., "Kringle domains of human plasminogen," Ciba Found. Symp., 212:46-60 Feb. 1997.

Castellino et al., "The existence of independent domain structures in human Lys77-plasminogen," J Biol Chem., 256(10):4778-82, May 25, 1981.

Chen W, Huang X, Ma Xw, Mo W, Wang WJ, and Song HY (2008) Enzymatic vitreolysis with recombinant microplasminogen and tissue plasminogen activator. Eye, 22, 300-307. Published online Aug. 17, 2007.

Chow et al. "Successful Closure of Traumatic Macular Holes" The Journal of Retinal and Vitreous Diseases, vol. 19, No. 5, May 1999 (405-409).

Christensen et al.. Enzymic Properties of the NEO-Plasmin-VAL-422 (miniplasmin). Biochimica et Biophysica Acta. 567:472-481, Apr. 1979.

Collen, D. "Revival of Plasmin as a Therapeutic Agent?" Thromb Haemost Sep. 2001; 86: 731-2.

Doyonnas, et al., "Podocalyxin is a CD34-Related Marker of Murine Hematopoietic Stem Cells and Embryoid Erythroid Cells", Blood, 105(11):4170-4178, Jun. 2005.

Examiner's report issued for European Appl. No. 03812818.7, dated Oct. 13, 2009.

Examiners Report, Australian Patent Application No. 2003 300 821, dated Jan. 30, 2009 (2 pages).

Facts About Diabetic Retinopathy from http://www.nei.nih.goy/health/diabetic/retinopathy.asp. Nov. 2010, p. 1-8.

Foos, Robert Y. "Vitreoretinal juncture; topographical variations" Investigative Opthalmology, Oct. 1972, vol. 11, No. 10, (801-808).

Furness, et al., "Beyond Mere Markers: Functions for CD34 Family of Sialomucins in Hematopoiesis", Immunologic Research, 34(1):13-32, Jan. 2006.

Gandorfer A, "Experimental evaluation of microplasmin—an alternative to vital dyes", in *Developments in Ophthalmol*, 42, 153-159, 2008.

Gandorfer A and Kampik A, Intrasurgical plasmin enzyme in diabetic macular edema. Am J Ophthalmol, 139, 949-950, May 2005.

Gandorfer et al., "Plasmin-assisted vitrectomy eliminates cortical vitreous remnants," Eye, 16:95-97, Jan. 2002.

Gandorfer et al., "Vitreoretinal Morphology of Plasmin-Treated Human Eyes," Am. J Opthalmol., 133(1): 156-159 (Jan. 2002).

Gandorfer et al., Ultrastructure of the vitreoretinal interface following plasmin assisted vitrectomy, Br. J. Ophthalmology, 85:6-10, Jan. 2001.

Glaucoma. MayoClinic.com; Mayo Foundation for Medical Education and Research (MFMER). Jul. 7, 2008 <http://www.mayoclinic.com/print/glaucoma/DS00283/METHOD=print&DSECTION=all> (p. 1-14).

Goldberg GI, Strongin A, Collier IE, Genrich LT, and Marmer BL, Interaction of 92-kDa type IV collagenase with the tissue inhibitor of metalloproteinases prevents dimerization, complex formation with interstitial collagenase, and activation ofthe proenzyme with stromelysin. J Biol Chem, 267, 4583-4591, Mar. 1992.

Gonias, Steven and Figler, Nancy. ".alpha.2-Macroglobulin is the primary inhibitor of miniplasmin in vitro and in vivo in the mouse" Biochem. J., Oct. 1988, 255, 725-730.

Grant, M. et al., "Fibronectin Fragments Modulate Human Retinal Capillary Cell Proliferation and Migration," Diabetes, 47: 1335-50. Aug. 1998.

Hara A, Surface structure of rabbit and human retina after enzymatic separation of inner limiting membrane. Jpn J Ophthalmol, 38, 375-381. No Month Available 1994.

Hara, et al., "Identification of Podocalyxin-Like Protein 1 as a Novel Cell Surface Marker for Hemangioblasts in the Murine Aorta-Gonad-Mesonephros Region", Immunity, 11:567-578 Nov. 1999.

Hermel M and Schrage NF, Efficacy of plasmin enzymes and chondroitinase ABC in creating posterior vitreous separation in the pig: a masked, placebo-controlled in vivo study. Graefes Arch Clin Exp Ophthalmol, 245, 399-406, Mar. 2007.

Immonen et al "Plasmin in subretinal fluid," Acta Ophthalmol. (Copenh.), 66(6):647-51 (Dec. 1988).

Immonen et al., "Tissue-type plasminogen activator in subretinal fluid," Curr Eye Res., 8(3):249-52 (Mar. 1989).

Jorge R, Oyamaguchi EK, Cardillo JA, Gobbi A, Laicine EM, and Haddad A, Intravitreal injection of dispase causes retinal hemorrhages in rabbit and human eyes. Curr Eye Res, 26(2), 107-112, Jan. 2003.

Joshi MM, Ciaccia S, Trese MT, and Capone A, Jr., Posterior hyaloid contracture in pediatric vitreoretinopathies. Retina, 26(S7), S38-S41, Sep. 2006.

Joshi MM, Drenser K, Hartzer M, Dailey W, Capone A, Jr., and Trese MT, Intraschisis cavity fluid composition in congenital X-linked retinoschisis. Retina, 26(S7), S57-S60, Sep. 2006.

Kerosuo, et al., "Podocalyxin in Human Haematopoietic Cells", British Journal of Haematology, 124:809-818, Mar. 2004.

Kershaw, et al., "Molecular Cloning and Characterization of Human Podocalyxin-like Protein", Journal of Biological Chemistry, 272(25):15708-15714, Jun. 1997.

Kershaw, et al., "Molecular Cloning, Expression, and Characterization of Podocalyxin-like Protein 1 from Rabbit as a Transmembrane Protein of Glomerular Podocytes and Vascular Endothelium", Journal of Biological Chemistry, 270(49):29439-29446, Dec. 1995.

(56) References Cited

OTHER PUBLICATIONS

Khono et al. "Immunofluorescent Studies of Fibronectin and Laminin in the Human Eye" Investigate Opthalmology & Visual Science, vol. 28. Mar. 1987. (506-514).

Kim NJ, Yu HG, Yu YS, and Chung H, Long-term effect of plasmin on the vitreolysis in rabbit eyes. Korean J Ophthalmol, 18, 35-40, Jun. 2004.

Kobayashi, GenBank Accession No. AB020726 (2 pages), No Month Available 1999.

Komorowicz, et al., "Fibrinolysis with Des-Kringle Derivatives of Plasmin and Its Modulation by Plasma Protease Inhisitors," Biochemistry 37:9112-9118, Jun. 23, 1998.

Laryukhina GM and Ziangirova GG, Experimental enzymatic vitreolysis. Vestn Oftalmol (6) 77-79, Nov./Dec. 1977.

Lasters et al., "Enzymatic properties of phage-displayed fragments of human plasminogen," Eur J Biochem., 244(3):946-52 (Mar. 15, 1997).

Li X, Shi X, and Fan J, Posterior vitreous detachment with plasmin in the isolated human eye. Graefes Arch Clin Exp Ophthalmol, 240, 56-62, Jan. 2002.

Lijnen et al., "On the role of the carbohydrate side chains of human plasminogen in its interaction with alpha 2-antiplasmin and fibrin," Eur. J Biochem., 120(1):149-54 (Nov. 1981).

Liotta et al., "Effect of plasminogen activator (urokinase), plasmin, and thrombin on glycoprotein and collagenous components of basement membrane," Cancer Res., 41(11 Pt 1):4629-36 (Nov. 1981).

Mandl, "Bacterial collegenases and their clinical applications," Arzneimittelforschung, 32(10a): 1381-4, No Month Available 1982.

Marder et al. "Plasmin Induces Local Thromolysis Without Causing Hemorrhage: A Comparison with Tissue Plasminogen Activator in the Rabbit" Thromb Haemost; 86(3): 739-45, Sep. 2001.

Margherio, et al., "Plasmin Enzyme-Assisted Vitrectomy in Traumatic Pediatric Macular Holes", Ophthalmology, 105(9):1617-1620, Sep. 1998.

McNagny, et al., "Thrombomucin, a Novel Cell Surface Protein that Defines Thrombocytes and Multipotent Hematopoietic Progenitors", Journal of Cell Biology, 138(6):1395-1407, Sep. 22, 1997.

Medical Appendix. Macular Degeneration. <http://www.patscotland.org.uk/medical.sub.--appendices/M/MACULAR%20DE- GENERATION.pdf> (pp. 1-6), Sep. 2002.

Moorhead and Radtke, "Enzyme-assisted vitrectomy with bacterial collagenase. Pilot human studies," Retina, 5(2):98-100 (Spring-Summer, 1985).

Moorhead et al., "Bacterial collagenase. Proposed adjunct to vitrectomy with membranectomy," Arch. Ophthalmol.; 98(10): 182939 (Oct. 1980).

Moorhead et al., "Enzyme-assisted vitrectomy with bacterial collagenase.time course and toxicity studies," Arch. Ophthatmol.,101(2):265-74 (Feb. 1983).

Moser TL, Enghild JJ, Pizzo SV, and Stack MS, The extracellular matrix proteins laminin and fibronectin contain binding domains for human plasminogen and tissue plasminogen activator. J Biol Chem, 268, 18917-18923, Sep. 25, 1993.

Nakayama, et al., Clinical Immunology (Rinsho), 36(5):751-8, No Month Available 2001.

O'Neill, R. and Shea, M., "The effects of bacterial collagenase in rabbit vitreous," Can J Ophthalmol., 8(2):366-70 (Apr. 1973).

Okajima K, Abe H, and Binder BR, Endothelial cell injury induced by plasmin in vitro. J Lab Clin Med, 126, 377-384, Oct. 1995.

Onitsuka, et al., "Two Distinct Precursors of Hematopoietic Stem Cells and Endothelial Progenitors Characterized by the PCLP1 Expression", Blood (ASH Annual Meeting Abstracts), Nov. 16, 2005:106(11), Abstract 2274., 1 page.

Onitsuka, et al., Blood (Journal of the American Societ of Hematology), 102(11):166a (Abstract # 579), Epub. Nov. 4, 2003 (2 pages).

Peisach, E. et al., "Crystal Structure of the Proenzyme Domain of Plasminogen," Biochemistry, 38(35): 11180-11188, Aug. 31, 1999.

Powell JR and Castellino FJ, 1980, Activation of human neoplasminogen-Val442 by urokinase and streptokinase and a kinetic characterization of neoplasmin-Val442. J Biol Chem, 255, 5329-5335, Jun. 10, 1980.

Proksch JW, Driot JY, Vandeberg P, and Ward KW, Nonclinical safety and pharmacokinetics of intravitreally administered human-derived plasmin in rabbits and minipigs. J Ocul Pharmacol Ther, 24(3), 320-332, Jun. 2008.

Quiram PA, Leverenz VR, Baker RM, Dang L, Giblin FJ and Trese MT, Microplasmin-induced posterior vitreous detachment affects vitreous oxygen levels. Retina, 27(8), 1090-1096, Oct. 2007.

Rizzo S, Pellegrini G, Benocci F, Belting C, Baicchi U, and Vispi M, Autologous plasmin for pharmacologic vitreolysis prepared 1 hour before surgery. Retina, 26(7), 792-796, Sep. 2006.

Sakuma et al. "Efficacy of autologous plasmin for idiopathic macular hole surgery" Eur J Opthalmol 15(6), 787-794, Nov./Dec. 2005.

Sakuma T, Tanaka M, Inoue J, Mizota A, Souri M, and Ichinose A, Use of autologous plasmin during vitrectomy for diabetic maculopathy. Eur J Ophthalmol, 16(1), 138-140, Jan./Feb. 2006.

Sakuma, et al., "Safety of In Vivo Pharmacologic Vitreolysis with Recombinant Microplasmin in Rabbit Eyes," IOVS, 46(9):3295-3299 (Sep. 2005).

Sakuma, T., "Plasmin assisted vitrectomy for diabetic retinopathy," Clinic All-round 51:2891-2892, No Month Available 2002 (7 pages).

Sebag J, Pharmacologic vitreolysis. Retina, 18(1), 1-3, Jan. 1998.

Sebag J, Molecular biology of pharmacologic vitreolysis. Trans Am Ophthalmol Soc, 103, 473-494, Dec. 2005.

Sebag J, Is pharmacologic vitreolysis brewing Retina, 22, 1-3, Feb. 2002.

Sebag J and Balazs EA, Morphology and ultrastructure of human vitreous fibers. Invest Ophthalmol Vis Sci, 30, 1867-1871, Jan. 1989.

Sebag J, Ansari RR, and Suh KI (2007) Pharmacologic vitreolysis with microplasmin increases vitreous diffusion coefficients. Graefes Arch Clin Exp Ophthalmol, 245, 576-580, published online Aug. 29, 2006.

Seeber, Michelle. "While not preventable, glaucoma is treatable" The Woodward News Online. <http://www.woodwardnews.net/homepage/local.sub.--story.sub.--01809062-2.html/resources.sub.--printstory> (p. 1-2), Jan. 18, 2009.

Shapiro SD, Fliszar CJ, Broekelmann TJ, Mecham RP, Senior RM, and Welgus HG, Activation of the 92-kDa gelatinase by stromelysin and 4-aminophenylmercuric acetate. Differential processing and stabilization of the carboxyl-terminal domain bytissue inhibitor of metalloproteinases (TIMP). J Biol Chem, 270, 6351-6356, Mar. 17, 1995.

Sigma Specification Sheet. 2008. Plasmin from human plasma, lyophilized powder, ≥3 units/mg protein, (http://www.sigmaaldrich.com/catalog/search/SpecificationSheetPage/SIGMA/-P1867?PrtPrv.about.1). Accessed Jun. 13, 2008, 1 page.

Sottrup-Jensen et al., in *Atlas of Protein Sequence and Structure*, vol. 5, suppl. 3 p. 90-91, eds. Dayhoff (National Biomedical Research Foundation, Silver Spring, MD), 1977, 4 pages.

Stack MS, Moser TL and Pizzo SV, Binding of human plasminogen to basement-membrane (type IV) collagen. Biochem J, 284, 103-108, May 1992.

Staubach F, Nober V, and Janknecht P, Enzyme-assisted vitrectomy in enucleated pig eyes: a comparison of hyaluronidase, chondroitinase, and plasmin. Curr Eye Res, 29, 261-268, Jan. 2004.

Suenson, Elisabeth and Thorsen, Sixtus. "Secondary-site binding of Glu-plasmin, Lys-plasmin and miniplasmin to fibrin" Biochem. J., 197, 619-628, Jan. 9, 1981.

Takano A, Hirata A, Inomata Y, Kawaji T, Nakagawa K, Nagata S, and Tanihara H, Intravitreal plasmin injection activates endogenous matrix metalloproteinase-2 in rabbit and human vitreous. Am J Ophthalmol, 140(4), 654-660, Oct. 2005.

Takano A, Hirata A, Ogasawara K, Sagara N, Inomata Y, Kawaji T, and Tanihara H, Posterior vitreous detachment induced by nattokinase (subtilisin NAT): a novel enzyme for pharmacologic vitreolysis. Invest Ophthalmol Vis Sci, 47(5), 2075-2079, May 2006.

Tanaka and Qui, "Pharmacological Vitrectomy," Sem Opthalmol. 15(1):51-61 (Mar. 2000).

Tanaka et al. Pharmacological vitrectomy. Semin. Ophthalmol. 15(1):51-61, Mar. 2000.

(56) References Cited

OTHER PUBLICATIONS

Tanaka, Immunology Frontier, 10(5):300-3003, Jan. 2000.
Tezel et al., "Posterior vitreous detachment with dispase," Retina,18(1 ):7-15, Jan. 1998.
Trese etal., "Autologous Plasmin Enzyme Membrane Peeling and Irrigation by Vitrectomy for Stage 3 Macular Holes", abstract 950, Annual Meeting of the Association for Research in Vision and Opthalmology, Fort Lauderdale (IOVS), Florida; May 9-14, 1999. 2 pages.
Trese MT, Enzymatic vitreous surgery. Semin Ophthalmol, 15, 116-121, Jan. 2000.
Trese, et al., "A New Approach to Stage 3 Macular Holes", Ophthalmology, 107(8):1607-1611, Aug. 2000.
Trese, M. T. "Enzymatic-assisted vitrectomy," EYE, vol. 16(4): 365-368, Jul. 2002.
Van Setten et al., "Plasmin and plasminogen activator activities in tear fluid during corneal wound healing after anterior keratectomy," Curr Eye Res., 8(12): 1293-8 (Dec. 1989).
Verstraeten et al., "Pharmacologic Induction of Posterior Vitreous Detachment in the Rabbit," Arch Ophthalmol., 111:849-854 (Jun. 1993).
Wang F, Wang Z, Sun X, Wang F, Xu X, and Zhang X, Safety and efficacy of dispase and plasmin in pharmacologic vitreolysis. Invest Ophthalmol Vis Sci, 45(9), 3286-3290, Sep. 2004.
Wang ZL, Zhang X, Xu X, Sun XD, and Wang F, PVD following plasmin but not hyaluronidase: implications for combination pharmacologic vitreolysis therapy. Retina, 25, 38-43, Jan. 2005.
Williams et al., "Autologous plasmin enzyme in the surgical management of diabetic retinopathy," Ophthalmology, 108(10): 1902-5; discussion 1905-6 (Oct. 2001).
Wiman and Collen,"Molecular Mechanism of physiological fibrinolysis," Nature 272(6):549-550, Apr. 6, 1978.
Wiman and Wallen, "The specific interaction between plasminogen and fibrin: A physiological role of the lysine binding site in plasminogen," Thrombosis Research, 10(2):213-222, Feb. 1977.
Wu HI, Shi GY, and Bender ML, Preparation and purification of microplasmin. Proc Natl Acad Sci U S A, 84(23), 8292-8295, Dec. 15, 1987.
Wu WC, Drenser KA, Capone A, Williams GA, and Trese MT Plasmin enzyme-assisted vitreoretinal surgery in congenital X-linked retinoschisis: surgical techniques based on a new classification system. Retina, 27(8), 1079-1085, Oct. 2007.
Wu WC, Drenser KA, Trese MT, Williams GA, and Capone A, Pediatric traumatic macular hole: results of autologous plasmin enzyme-assisted vitrectomy. Am J Ophthalmol, 144(5), 668-672, Nov. 2007.
Xiaoxin Li et al., "Posterior vitreous detachment with plasmin in the isolated human eye," Graefe's Arch Clin Exp Ophthalmol, 240: 56-62, Jan. 2002.
Xu et al., "Permeability and Diffusion in Vitreous Humor: Implications for Drug Delivery," Pharm. Res., 17(6):664-669, Jun. 2000.

\* cited by examiner

FIGURE 1 A

| | | | | | | | | | | | | | | | | |
|---|---|---|---|---|---|---|---|---|---|---|---|---|---|---|---|---|
| gag | cct | ctg | gat | gac | tat | gtg | aat | acc | cag | ggg | gct | tca | ctg | ttc | agt | 48 |
| Glu | Pro | Leu | Asp | Asp | Tyr | Val | Asn | Thr | Gln | Gly | Ala | Ser | Leu | Phe | Ser | |
| 1 | | | | 5 | | | | | 10 | | | | | 15 | | |
| gtc | act | aag | aag | cag | ctg | gga | gca | gga | agt | ata | gaa | gaa | tgt | gca | gca | 96 |
| Val | Thr | Lys | Lys | Gln | Leu | Gly | Ala | Gly | Ser | Ile | Glu | Glu | Cys | Ala | Ala | |
| | | | 20 | | | | | 25 | | | | | 30 | | | |
| aaa | tgt | gag | gag | gac | gaa | gaa | ttc | acc | tgc | agg | gca | ttc | caa | tat | cac | 144 |
| Lys | Cys | Glu | Glu | Asp | Glu | Glu | Phe | Thr | Cys | Arg | Ala | Phe | Gln | Tyr | His | |
| | | 35 | | | | | 40 | | | | | 45 | | | | |
| agt | aaa | gag | caa | caa | tgt | gtg | ata | atg | gct | gaa | aac | agg | aag | tcc | tcc | 192 |
| Ser | Lys | Glu | Gln | Gln | Cys | Val | Ile | Met | Ala | Glu | Asn | Arg | Lys | Ser | Ser | |
| | 50 | | | | | 55 | | | | | 60 | | | | | |
| ata | atc | att | agg | atg | aga | gat | gta | gtt | tta | ttt | gaa | aag | aaa | gtg | tat | 240 |
| Ile | Ile | Ile | Arg | Met | Arg | Asp | Val | Val | Leu | Phe | Glu | Lys | Lys | Val | Tyr | |
| 65 | | | | | 70 | | | | | 75 | | | | | 80 | |
| ctc | tca | gag | tgc | aag | act | ggg | aat | gga | aag | aac | tac | aga | ggg | acg | atg | 288 |
| Leu | Ser | Glu | Cys | Lys | Thr | Gly | Asn | Gly | Lys | Asn | Tyr | Arg | Gly | Thr | Met | |
| | | | | 85 | | | | | 90 | | | | | 95 | | |
| tcc | aaa | aca | aaa | aat | ggc | atc | acc | tgt | caa | aaa | tgg | agt | tcc | act | tct | 336 |
| Ser | Lys | Thr | Lys | Asn | Gly | Ile | Thr | Cys | Gln | Lys | Trp | Ser | Ser | Thr | Ser | |
| | | | 100 | | | | | 105 | | | | | 110 | | | |
| ccc | cac | aga | cct | aga | ttc | tca | cct | gct | aca | cac | ccc | tca | gag | gga | ctg | 384 |
| Pro | His | Arg | Pro | Arg | Phe | Ser | Pro | Ala | Thr | His | Pro | Ser | Glu | Gly | Leu | |
| | | 115 | | | | | 120 | | | | | 125 | | | | |
| gag | gag | aac | tac | tgc | agg | aat | cca | gac | aac | gat | ccg | cag | ggg | ccc | tgg | 432 |
| Glu | Glu | Asn | Tyr | Cys | Arg | Asn | Pro | Asp | Asn | Asp | Pro | Gln | Gly | Pro | Trp | |
| | | 130 | | | | | 135 | | | | | 140 | | | | |
| tgc | tat | act | act | gat | cca | gaa | aag | aga | tat | gac | tac | tgc | gac | att | ctt | 480 |
| Cys | Tyr | Thr | Thr | Asp | Pro | Glu | Lys | Arg | Tyr | Asp | Tyr | Cys | Asp | Ile | Leu | |
| 145 | | | | | 150 | | | | | 155 | | | | | 160 | |
| gag | tgt | gaa | gag | gaa | tgt | atg | cat | tgc | agt | gga | gaa | aac | tat | gac | ggc | 528 |
| Glu | Cys | Glu | Glu | Glu | Cys | Met | His | Cys | Ser | Gly | Glu | Asn | Tyr | Asp | Gly | |
| | | | | 165 | | | | | 170 | | | | | 175 | | |
| aaa | att | tcc | aag | acc | atg | tct | gga | ctg | gaa | tgc | cag | gcc | tgg | gac | tct | 576 |
| Lys | Ile | Ser | Lys | Thr | Met | Ser | Gly | Leu | Glu | Cys | Gln | Ala | Trp | Asp | Ser | |
| | | | 180 | | | | | 185 | | | | | 190 | | | |

FIGURE 1B

| cag | agc | cca | cac | gct | cat | gga | tac | att | cct | tcc | aaa | ttt | cca | aac | aag | 624 |
| Gln | Ser | Pro | His | Ala | His | Gly | Tyr | Ile | Pro | Ser | Lys | Phe | Pro | Asn | Lys | |
| | | 195 | | | | | 200 | | | | | 205 | | | | |

| aac | ctg | aag | aag | aat | tac | tgt | cgt | aac | ccc | gat | agg | gag | ctg | cgg | cct | 672 |
| Asn | Leu | Lys | Lys | Asn | Tyr | Cys | Arg | Asn | Pro | Asp | Arg | Glu | Leu | Arg | Pro | |
| | 210 | | | | | 215 | | | | | 220 | | | | | |

| tgg | tgt | ttc | acc | acc | gac | ccc | aac | aag | cgc | tgg | gaa | ctt | tgc | gac | atc | 720 |
| Trp | Cys | Phe | Thr | Thr | Asp | Pro | Asn | Lys | Arg | Trp | Glu | Leu | Cys | Asp | Ile | |
| 225 | | | | | 230 | | | | | 235 | | | | | 240 | |

| ccc | cgc | tgc | aca | aca | cct | cca | cca | tct | tct | ggt | ccc | acc | tac | cag | tgt | 768 |
| Pro | Arg | Cys | Thr | Thr | Pro | Pro | Pro | Ser | Ser | Gly | Pro | Thr | Tyr | Gln | Cys | |
| | | | | 245 | | | | | 250 | | | | | 255 | | |

| ctg | aag | gga | aca | ggt | gaa | aac | tat | cgc | ggg | aat | gtg | gct | gtt | acc | gtt | 816 |
| Leu | Lys | Gly | Thr | Gly | Glu | Asn | Tyr | Arg | Gly | Asn | Val | Ala | Val | Thr | Val | |
| | | | 260 | | | | | 265 | | | | | 270 | | | |

| tcc | ggg | cac | acc | tgt | cag | cac | tgg | agt | gca | cag | acc | cct | cac | aca | cat | 864 |
| Ser | Gly | His | Thr | Cys | Gln | His | Trp | Ser | Ala | Gln | Thr | Pro | His | Thr | His | |
| | | 275 | | | | | 280 | | | | | 285 | | | | |

| aac | agg | aca | cca | gaa | aac | ttc | ccc | tgc | aaa | aat | ttg | gat | gaa | aac | tac | 912 |
| Asn | Arg | Thr | Pro | Glu | Asn | Phe | Pro | Cys | Lys | Asn | Leu | Asp | Glu | Asn | Tyr | |
| | 290 | | | | | 295 | | | | | 300 | | | | | |

| tgc | cgc | aat | cct | gac | gga | aaa | agg | gcc | cca | tgg | tgc | cat | aca | acc | aac | 960 |
| Cys | Arg | Asn | Pro | Asp | Gly | Lys | Arg | Ala | Pro | Trp | Cys | His | Thr | Thr | Asn | |
| 305 | | | | | 310 | | | | | 315 | | | | | 320 | |

| agc | caa | gtg | cgg | tgg | gag | tac | tgt | aag | ata | ccg | tcc | tgt | gac | tcc | tcc | 1008 |
| Ser | Gln | Val | Arg | Trp | Glu | Tyr | Cys | Lys | Ile | Pro | Ser | Cys | Asp | Ser | Ser | |
| | | | | 325 | | | | | 330 | | | | | 335 | | |

| cca | gta | tcc | acg | gaa | caa | ttg | gct | ccc | aca | gca | cca | cct | gag | cta | acc | 1056 |
| Pro | Val | Ser | Thr | Glu | Gln | Leu | Ala | Pro | Thr | Ala | Pro | Pro | Glu | Leu | Thr | |
| | | | 340 | | | | | 345 | | | | | 350 | | | |

| cct | gtg | gtc | cag | gac | tgc | tac | cat | ggt | gat | gga | cag | agc | tac | cga | ggc | 1104 |
| Pro | Val | Val | Gln | Asp | Cys | Tyr | His | Gly | Asp | Gly | Gln | Ser | Tyr | Arg | Gly | |
| | | 355 | | | | | 360 | | | | | 365 | | | | |

| aca | tcc | tcc | acc | acc | acc | aca | gga | aag | aag | tgt | cag | tct | tgg | tca | tct | 1152 |
| Thr | Ser | Ser | Thr | Thr | Thr | Thr | Gly | Lys | Lys | Cys | Gln | Ser | Trp | Ser | Ser | |
| | 370 | | | | | 375 | | | | | 380 | | | | | |

| atg | aca | cca | cac | cgg | cac | cag | aag | acc | cca | gaa | aac | tac | cca | aat | gct | 1200 |
| Met | Thr | Pro | His | Arg | His | Gln | Lys | Thr | Pro | Glu | Asn | Tyr | Pro | Asn | Ala | |

FIGURE 1C

| | 385 | | | | | 390 | | | | | 395 | | | | | 400 | |
|---|---|---|---|---|---|---|---|---|---|---|---|---|---|---|---|---|---|
| ggc Gly | ctg Leu | aca Thr | atg Met | aac Asn 405 | tac Tyr | tgc Cys | agg Arg | aat Asn | cca Pro 410 | gat Asp | gcc Ala | gat Asp | aaa Lys | ggc Gly 415 | ccc Pro | | 1248 |
| tgg Trp | tgt Cys | ttt Phe | acc Thr 420 | aca Thr | gac Asp | ccc Pro | agc Ser | gtc Val 425 | agg Arg | tgg Trp | gag Glu | tac Tyr | tgc Cys 430 | aac Asn | ctg Leu | | 1296 |
| aaa Lys | aaa Lys | tgc Cys 435 | tca Ser | gga Gly | aca Thr | gaa Glu | gcg Ala 440 | agt Ser | gtt Val | gta Val | gca Ala | cct Pro 445 | ccg Pro | cct Pro | gtt Val | | 1344 |
| gtc Val | ctg Leu 450 | ctt Leu | cca Pro | gat Asp | gta Val | gag Glu 455 | act Thr | cct Pro | tcc Ser | gaa Glu | gaa Glu 460 | gac Asp | tgt Cys | atg Met | ttt Phe | | 1392 |
| ggg Gly 465 | aat Asn | ggg Gly | aaa Lys | gga Gly | tac Tyr 470 | cga Arg | ggc Gly | aag Lys | agg Arg | gcg Ala 475 | acc Thr | act Thr | gtt Val | act Thr | ggg Gly 480 | | 1440 |
| acg Thr | cca Pro | tgc Cys | cag Gln | gac Asp 485 | tgg Trp | gct Ala | gcc Ala | cag Gln | gag Glu 490 | ccc Pro | cat His | aga Arg | cac His | agc Ser 495 | att Ile | | 1488 |
| ttc Phe | act Thr | cca Pro | gag Glu 500 | aca Thr | aat Asn | cca Pro | cgg Arg | gcg Ala 505 | ggt Gly | ctg Leu | gaa Glu | aaa Lys | aat Asn 510 | tac Tyr | tgc Cys | | 1536 |
| cgt Arg | aac Asn | cct Pro 515 | gat Asp | ggt Gly | gat Asp | gta Val | ggt Gly 520 | ggt Gly | ccc Pro | tgg Trp | tgc Cys | tac Tyr 525 | acg Thr | aca Thr | aat Asn | | 1584 |
| cca Pro | aga Arg 530 | aaa Lys | ctt Leu | tac Tyr | gac Asp | tac Tyr 535 | tgt Cys | gat Asp | gtc Val | cct Pro | cag Gln 540 | tgt Cys | gcg Ala | gcc Ala | cct Pro | | 1632 |
| tca Ser 545 | ttt Phe | gat Asp | tgt Cys | ggg Gly | aag Lys 550 | cct Pro | caa Gln | gtg Val | gag Glu | ccg Pro 555 | aag Lys | aaa Lys | tgt Cys | cct Pro | gga Gly 560 | | 1680 |
| agg Arg | gtt Val | gtg Val | ggg Gly | ggg Gly 565 | tgt Cys | gtg Val | gcc Ala | cac His | cca Pro 570 | cat His | tcc Ser | tgg Trp | ccc Pro | tgg Trp 575 | caa Gln | | 1728 |
| gtc Val | agt Ser | ctt Leu | aga Arg 580 | aca Thr | agg Arg | ttt Phe | gga Gly | atg Met 585 | cac His | ttc Phe | tgt Cys | gga Gly | ggc Gly 590 | acc Thr | ttg Leu | | 1776 |
| ata | tcc | cca | gag | tgg | gtg | ttg | act | gct | gcc | cac | tgc | ttg | gag | aag | tcc | | 1824 |

FIGURE 1D

| | | | | | | | | | | | | | | | |
|---|---|---|---|---|---|---|---|---|---|---|---|---|---|---|---|
| Ile | Ser | Pro 595 | Glu | Trp | Val | Leu | Thr 600 | Ala | Ala | His | Cys | Leu 605 | Glu | Lys | Ser |
| cca Pro | agg Arg 610 | cct Pro | tca Ser | tcc Ser | tac Tyr | aag Lys 615 | gtc Val | atc Ile | ctg Leu | ggt Gly | gca Ala 620 | cac His | caa Gln | gaa Glu | gtg Val | 1872 |
| aat Asn 625 | ctc Leu | gaa Glu | ccg Pro | cat His | gtt Val 630 | cag Gln | gaa Glu | ata Ile | gaa Glu | gtg Val 635 | tct Ser | agg Arg | ctg Leu | ttc Phe | ttg Leu 640 | 1920 |
| gag Glu | ccc Pro | aca Thr | cga Arg | aaa Lys 645 | gat Asp | att Ile | gcc Ala | ttg Leu | cta Leu 650 | aag Lys | cta Leu | agc Ser | agt Ser | cct Pro 655 | gcc Ala | 1968 |
| gtc Val | atc Ile | act Thr | gac Asp 660 | aaa Lys | gta Val | atc Ile | cca Pro | gct Ala 665 | tgt Cys | ctg Leu | cca Pro | tcc Ser | cca Pro 670 | aat Asn | tat Tyr | 2016 |
| gtg Val | gtc Val | gct Ala 675 | gac Asp | cgg Arg | acc Thr | gaa Glu | tgt Cys 680 | ttc Phe | atc Ile | act Thr | ggc Gly | tgg Trp 685 | gga Gly | gaa Glu | acc Thr | 2064 |
| caa Gln | ggt Gly 690 | act Thr | ttt Phe | gga Gly | gct Ala | ggc Gly 695 | ctt Leu | ctc Leu | aag Lys | gaa Glu | gcc Ala 700 | cag Gln | ctc Leu | cct Pro | gtg Val | 2112 |
| att Ile 705 | gag Glu | aat Asn | aaa Lys | gtg Val | tgc Cys 710 | aat Asn | cgc Arg | tat Tyr | gag Glu | ttt Phe 715 | ctg Leu | aat Asn | gga Gly | aga Arg | gtc Val 720 | 2160 |
| caa Gln | tcc Ser | acc Thr | gaa Glu | ctc Leu 725 | tgt Cys | gct Ala | ggg Gly | cat His | ttg Leu 730 | gcc Ala | gga Gly | ggc Gly | act Thr | gac Asp 735 | agt Ser | 2208 |
| tgc Cys | cag Gln | ggt Gly | gac Asp 740 | agt Ser | gga Gly | ggt Gly | cct Pro | ctg Leu 745 | gtt Val | tgc Cys | ttc Phe | gag Glu | aag Lys 750 | gac Asp | aaa Lys | 2256 |
| tac Tyr | att Ile | tta Leu 755 | caa Gln | gga Gly | gtc Val | act Thr | tct Ser 760 | tgg Trp | ggt Gly | ctt Leu | ggc Gly | tgt Cys 765 | gca Ala | cgc Arg | ccc Pro | 2304 |
| aat Asn | aag Lys 770 | cct Pro | ggt Gly | gtc Val | tat Tyr | gtt Val 775 | cgt Arg | gtt Val | tca Ser | agg Arg | ttt Phe 780 | gtt Val | act Thr | tgg Trp | att Ile | 2352 |
| gag Glu 785 | gga Gly | gtg Val | atg Met | aga Arg | aat Asn 790 | aat Asn | taa  SEQ ID NO: 9<br>SEQ ID NO: 10 | | | | | | | | | 2400 |

FIGURE 2A

| | | | | | | | | | | | | | | | gcc | cct | 1632 |
|---|---|---|---|---|---|---|---|---|---|---|---|---|---|---|---|---|---|
| | | | | | | | | | | | | | | | Ala | Pro | |

| tca | ttt | gat | tgt | ggg | aag | cct | caa | gtg | gag | ccg | aag | aaa | tgt | cct | gga | 1680 |
|---|---|---|---|---|---|---|---|---|---|---|---|---|---|---|---|---|
| Ser 545 | Phe | Asp | Cys | Gly | Lys 550 | Pro | Gln | Val | Glu | Pro 555 | Lys | Lys | Cys | Pro | Gly 560 | |
| agg | gtt | gtg | ggg | ggg | tgt | gtg | gcc | cac | cca | cat | tcc | tgg | ccc | tgg | caa | 1728 |
| Arg | Val | Val | Gly | Gly 565 | Cys | Val | Ala | His | Pro | His 570 | Ser | Trp | Pro | Trp 575 | Gln | |
| gtc | agt | ctt | aga | aca | agg | ttt | gga | atg | cac | ttc | tgt | gga | ggc | acc | ttg | 1776 |
| Val | Ser | Leu | Arg 580 | Thr | Arg | Phe | Gly | Met 585 | His | Phe | Cys | Gly | Gly 590 | Thr | Leu | |
| ata | tcc | cca | gag | tgg | gtg | ttg | act | gct | gcc | cac | tgc | ttg | gag | aag | tcc | 1824 |
| Ile | Ser | Pro 595 | Glu | Trp | Val | Leu | Thr 600 | Ala | Ala | His | Cys | Leu 605 | Glu | Lys | Ser | |
| cca | agg | cct | tca | tcc | tac | aag | gtc | atc | ctg | ggt | gca | cac | caa | gaa | gtg | 1872 |
| Pro | Arg 610 | Pro | Ser | Ser | Tyr | Lys 615 | Val | Ile | Leu | Gly | Ala 620 | His | Gln | Glu | Val | |
| aat | ctc | gaa | ccg | cat | gtt | cag | gaa | ata | gaa | gtg | tct | agg | ctg | ttc | ttg | 1920 |
| Asn 625 | Leu | Glu | Pro | His | Val 630 | Gln | Glu | Ile | Glu | Val 635 | Ser | Arg | Leu | Phe | Leu 640 | |
| gag | ccc | aca | cga | aaa | gat | att | gcc | ttg | cta | aag | cta | agc | agt | cct | gcc | 1968 |
| Glu | Pro | Thr | Arg | Lys 645 | Asp | Ile | Ala | Leu | Leu 650 | Lys | Leu | Ser | Ser | Pro 655 | Ala | |
| gtc | atc | act | gac | aaa | gta | atc | cca | gct | tgt | ctg | cca | tcc | cca | aat | tat | 2016 |
| Val | Ile | Thr | Asp 660 | Lys | Val | Ile | Pro | Ala 665 | Cys | Leu | Pro | Ser | Pro 670 | Asn | Tyr | |
| gtg | gtc | gct | gac | cgg | acc | gaa | tgt | ttc | atc | act | ggc | tgg | gga | gaa | acc | 2064 |
| Val | Val | Ala 675 | Asp | Arg | Thr | Glu | Cys 680 | Phe | Ile | Thr | Gly | Trp 685 | Gly | Glu | Thr | |
| caa | ggt | act | ttt | gga | gct | ggc | ctt | ctc | aag | gaa | gcc | cag | ctc | cct | gtg | 2112 |
| Gln | Gly 690 | Thr | Phe | Gly | Ala | Gly 695 | Leu | Leu | Lys | Glu | Ala 700 | Gln | Leu | Pro | Val | |
| att | gag | aat | aaa | gtg | tgc | aat | cgc | tat | gag | ttt | ctg | aat | gga | aga | gtc | 2160 |
| Ile 705 | Glu | Asn | Lys | Val | Cys 710 | Asn | Arg | Tyr | Glu | Phe 715 | Leu | Asn | Gly | Arg | Val 720 | |

FIGURE 2B

| | | | | | | | | | | | | | | | | |
|---|---|---|---|---|---|---|---|---|---|---|---|---|---|---|---|---|
| caa | tcc | acc | gaa | ctc | tgt | gct | ggg | cat | ttg | gcc | gga | ggc | act | gac | agt | 2208 |
| Gln | Ser | Thr | Glu | Leu<br>725 | Cys | Ala | Gly | His | Leu<br>730 | Ala | Gly | Gly | Thr | Asp<br>735 | Ser | |
| tgc | cag | ggt | gac | agt | gga | ggt | cct | ctg | gtt | tgc | ttc | gag | aag | gac | aaa | 2256 |
| Cys | Gln | Gly | Asp<br>740 | Ser | Gly | Gly | Pro | Leu<br>745 | Val | Cys | Phe | Glu | Lys<br>750 | Asp | Lys | |
| tac | att | tta | caa | gga | gtc | act | tct | tgg | ggt | ctt | ggc | tgt | gca | cgc | ccc | 2304 |
| Tyr | Ile | Leu<br>755 | Gln | Gly | Val | Thr | Ser<br>760 | Trp | Gly | Leu | Gly | Cys<br>765 | Ala | Arg | Pro | |
| aat | aag | cct | ggt | gtc | tat | gtt | cgt | gtt | tca | agg | ttt | gtt | act | tgg | att | 2352 |
| Asn | Lys<br>770 | Pro | Gly | Val | Tyr<br>775 | Val | Arg | Val | Ser | Arg | Phe<br>780 | Val | Thr | Trp | Ile | |
| gag | gga | gtg | atg | aga | aat | aat | taa | SEQ ID NO: 3 | | | | | | | | 2400 |
| Glu | Gly | Val | Met | Arg | Asn<br>790 | Asn | | SEQ ID NO: 4 | | | | | | | | |
| Glu<br>785 | | | | | | | | | | | | | | | | |

FIGURE 3A

|  |  |  |  |  |  |  |  |  |  |  |  |  |  |  | gca<br>Ala<br>445 | cct<br>Pro | ccg<br>Pro | cct<br>Pro | gtt<br>Val | 1344 |
|---|---|---|---|---|---|---|---|---|---|---|---|---|---|---|---|---|---|---|---|---|
| gtc<br>Val | ctg<br>Leu<br>450 | ctt<br>Leu | cca<br>Pro | gat<br>Asp | gta<br>Val | gag<br>Glu<br>455 | act<br>Thr | cct<br>Pro | tcc<br>Ser | gaa<br>Glu | gaa<br>Glu<br>460 | gac<br>Asp | tgt<br>Cys | atg<br>Met | ttt<br>Phe | | | | | 1392 |
| ggg<br>Gly<br>465 | aat<br>Asn | ggg<br>Gly | aaa<br>Lys | gga<br>Gly | tac<br>Tyr<br>470 | cga<br>Arg | ggc<br>Gly | aag<br>Lys | agg<br>Arg | gcg<br>Ala<br>475 | acc<br>Thr | act<br>Thr | gtt<br>Val | act<br>Thr | ggg<br>Gly<br>480 | | | | | 1440 |
| acg<br>Thr | cca<br>Pro | tgc<br>Cys | cag<br>Gln | gac<br>Asp<br>485 | tgg<br>Trp | gct<br>Ala | gcc<br>Ala | cag<br>Gln | gag<br>Glu<br>490 | ccc<br>Pro | cat<br>His | aga<br>Arg | cac<br>His | agc<br>Ser<br>495 | att<br>Ile | | | | | 1488 |
| ttc<br>Phe | act<br>Thr | cca<br>Pro | gag<br>Glu<br>500 | aca<br>Thr | aat<br>Asn | cca<br>Pro | cgg<br>Arg | gcg<br>Ala<br>505 | ggt<br>Gly | ctg<br>Leu | gaa<br>Glu | aaa<br>Lys | aat<br>Asn<br>510 | tac<br>Tyr | tgc<br>Cys | | | | | 1536 |
| cgt<br>Arg | aac<br>Asn | cct<br>Pro<br>515 | gat<br>Asp | ggt<br>Gly | gat<br>Asp | gta<br>Val | ggt<br>Gly<br>520 | ggt<br>Gly | ccc<br>Pro | tgg<br>Trp | tgc<br>Cys | tac<br>Tyr<br>525 | acg<br>Thr | aca<br>Thr | aat<br>Asn | | | | | 1584 |
| cca<br>Pro | aga<br>Arg<br>530 | aaa<br>Lys | ctt<br>Leu | tac<br>Tyr | gac<br>Asp | tac<br>Tyr<br>535 | tgt<br>Cys | gat<br>Asp | gtc<br>Val | cct<br>Pro | cag<br>Gln<br>540 | tgt<br>Cys | gcg<br>Ala | gcc<br>Ala | cct<br>Pro | | | | | 1632 |
| tca<br>Ser<br>545 | ttt<br>Phe | gat<br>Asp | tgt<br>Cys | ggg<br>Gly | aag<br>Lys<br>550 | cct<br>Pro | caa<br>Gln | gtg<br>Val | gag<br>Glu | ccg<br>Pro<br>555 | aag<br>Lys | aaa<br>Lys | tgt<br>Cys | cct<br>Pro | gga<br>Gly<br>560 | | | | | 1680 |
| agg<br>Arg | gtt<br>Val | gtg<br>Val | ggg<br>Gly | ggg<br>Gly<br>565 | tgt<br>Cys | gtg<br>Val | gcc<br>Ala | cac<br>His | cca<br>Pro<br>570 | cat<br>His | tcc<br>Ser | tgg<br>Trp | ccc<br>Pro | tgg<br>Trp<br>575 | caa<br>Gln | | | | | 1728 |
| gtc<br>Val | agt<br>Ser | ctt<br>Leu | aga<br>Arg<br>580 | aca<br>Thr | agg<br>Arg | ttt<br>Phe | gga<br>Gly | atg<br>Met<br>585 | cac<br>His | ttc<br>Phe | tgt<br>Cys | gga<br>Gly | ggc<br>Gly<br>590 | acc<br>Thr | ttg<br>Leu | | | | | 1776 |
| ata<br>Ile | tcc<br>Ser | cca<br>Pro<br>595 | gag<br>Glu | tgg<br>Trp | gtg<br>Val | ttg<br>Leu | act<br>Thr<br>600 | gct<br>Ala | gcc<br>Ala | cac<br>His | tgc<br>Cys | ttg<br>Leu<br>605 | gag<br>Glu | aag<br>Lys | tcc<br>Ser | | | | | 1824 |
| cca<br>Pro | agg<br>Arg<br>610 | cct<br>Pro | tca<br>Ser | tcc<br>Ser | tac<br>Tyr | aag<br>Lys<br>615 | gtc<br>Val | atc<br>Ile | ctg<br>Leu | ggt<br>Gly | gca<br>Ala<br>620 | cac<br>His | caa<br>Gln | gaa<br>Glu | gtg<br>Val | | | | | 1872 |
| aat<br>  | ctc<br>  | gaa<br>  | ccg<br>  | cat<br>  | gtt<br>  | cag<br>  | gaa<br>  | ata<br>  | gaa<br>  | gtg<br>  | tct<br>  | agg<br>  | ctg<br>  | ttc<br>  | ttg<br>  | | | | | 1920 |

FIGURE 3B

| | | | | | | | | | | | | | | | |
|---|---|---|---|---|---|---|---|---|---|---|---|---|---|---|---|
| Asn 625 | Leu | Glu | Pro | His | Val 630 | Gln | Glu | Ile | Glu | Val 635 | Ser | Arg | Leu | Phe | Leu 640 |
| gag Glu | ccc Pro | aca Thr | cga Arg | aaa Lys 645 | gat Asp | att Ile | gcc Ala | ttg Leu | cta Leu 650 | aag Lys | cta Leu | agc Ser | agt Ser | cct Pro 655 | gcc Ala | 1968 |
| gtc Val | atc Ile | act Thr | gac Asp 660 | aaa Lys | gta Val | atc Ile | cca Pro | gct Ala 665 | tgt Cys | ctg Leu | cca Pro | tcc Ser | cca Pro 670 | aat Asn | tat Tyr | 2016 |
| gtg Val | gtc Val | gct Ala 675 | gac Asp | cgg Arg | acc Thr | gaa Glu | tgt Cys 680 | ttc Phe | atc Ile | act Thr | ggc Gly | tgg Trp 685 | gga Gly | gaa Glu | acc Thr | 2064 |
| caa Gln | ggt Gly 690 | act Thr | ttt Phe | gga Gly | gct Ala | ggc Gly 695 | ctt Leu | ctc Leu | aag Lys | gaa Glu | gcc Ala 700 | cag Gln | ctc Leu | cct Pro | gtg Val | 2112 |
| att Ile 705 | gag Glu | aat Asn | aaa Lys | gtg Val | tgc Cys 710 | aat Asn | cgc Arg | tat Tyr | gag Glu | ttt Phe 715 | ctg Leu | aat Asn | gga Gly | aga Arg | gtc Val 720 | 2160 |
| caa Gln | tcc Ser | acc Thr | gaa Glu | ctc Leu 725 | tgt Cys | gct Ala | ggg Gly | cat His | ttg Leu 730 | gcc Ala | gga Gly | ggc Gly | act Thr | gac Asp 735 | agt Ser | 2208 |
| tgc Cys | cag Gln | ggt Gly | gac Asp 740 | agt Ser | gga Gly | ggt Gly | cct Pro | ctg Leu 745 | gtt Val | tgc Cys | ttc Phe | gag Glu | aag Lys 750 | gac Asp | aaa Lys | 2256 |
| tac Tyr | att Ile | tta Leu 755 | caa Gln | gga Gly | gtc Val | act Thr | tct Ser 760 | tgg Trp | ggt Gly | ctt Leu | ggc Gly | tgt Cys 765 | gca Ala | cgc Arg | ccc Pro | 2304 |
| aat Asn | aag Lys 770 | cct Pro | ggt Gly | gtc Val | tat Tyr | gtt Val 775 | cgt Arg | gtt Val | tca Ser | agg Arg | ttt Phe 780 | gtt Val | act Thr | tgg Trp | att Ile | 2352 |
| gag Glu 785 | gga Gly | gtg Val | atg Met | aga Arg | aat Asn 790 | aat Asn | taa | SEQ ID NO: 7 SEQ ID NO: 8 | | | | | | | | 2400 |

SEQUENCE LISTING

```
<160> NUMBER OF SEQ ID NOS: 15

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
ggggtatctc tcgagaaaag agccccttca tttgattg                              38

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
gtttttgttc tagattaatt atttctcatc actccctc                              38

<210> SEQ ID NO 3
<211> LENGTH: 750
<212> TYPE: DNA
<213> ORGANISM: Homo sapiens
<220> FEATURE:
<221> NAME/KEY: CDS
```

<222> LOCATION: (1)..(747)

<400> SEQUENCE: 3

```
gcc cct tca ttt gat tgt ggg aag cct caa gtg gag ccg aag aaa tgt      48
Ala Pro Ser Phe Asp Cys Gly Lys Pro Gln Val Glu Pro Lys Lys Cys
1               5                   10                  15 cct gga agg gtt gtg ggg ggg tgt gtg gcc cac cca cat tcc tgg ccc      96
Pro Gly Arg Val Val Gly Gly Cys Val Ala His Pro His Ser Trp Pro
            20                  25                  30 tgg caa gtc agt ctt aga aca agg ttt gga atg cac ttc tgt gga ggc     144
Trp Gln Val Ser Leu Arg Thr Arg Phe Gly Met His Phe Cys Gly Gly
        35                  40                  45 acc ttg ata tcc cca gag tgg gtg tta act gct gcc cac tgc ttg gag     192
Thr Leu Ile Ser Pro Glu Trp Val Leu Thr Ala Ala His Cys Leu Glu
    50                  55                  60 aag tcc cca agg cct tca tcc tac aag gtc atc ctg ggt gca cac caa     240
Lys Ser Pro Arg Pro Ser Ser Tyr Lys Val Ile Leu Gly Ala His Gln
65                  70                  75                  80 gaa gtg aat ctc gaa ccg cat gtt cag gaa ata gaa gtg tct agg ctg     288
Glu Val Asn Leu Glu Pro His Val Gln Glu Ile Glu Val Ser Arg Leu
                85                  90                  95 ttc ttg gag ccc aca cga aaa gat att gcc ttg cta aag cta agc agt     336
Phe Leu Glu Pro Thr Arg Lys Asp Ile Ala Leu Leu Lys Leu Ser Ser
            100                 105                 110 cct gcc gtc atc act gac aaa gta atc cca gct tgt ctg cca tcc cca     384
Pro Ala Val Ile Thr Asp Lys Val Ile Pro Ala Cys Leu Pro Ser Pro
        115                 120                 125 aat tat gtg gtc gct gac cgg acc gaa tgt ttc atc act ggc tgg gga     432
Asn Tyr Val Val Ala Asp Arg Thr Glu Cys Phe Ile Thr Gly Trp Gly
    130                 135                 140 gaa acc caa ggt act ttt gga gct ggc ctt ctc aag gaa gcc cag ctc     480
Glu Thr Gln Gly Thr Phe Gly Ala Gly Leu Leu Lys Glu Ala Gln Leu
145                 150                 155                 160 cct gtg att gag aat aaa gtg tgc aat cgc tat gag ttt ctg aat gga     528
Pro Val Ile Glu Asn Lys Val Cys Asn Arg Tyr Glu Phe Leu Asn Gly
                165                 170                 175 aga gtc caa tcc acc gaa ctc tgt gct ggg cat ttg gcc gga ggc act     576
Arg Val Gln Ser Thr Glu Leu Cys Ala Gly His Leu Ala Gly Gly Thr
            180                 185                 190 gac agt tgc cag ggt gac agt gga ggt cct ctg gtt tgc ttc gag aag     624
Asp Ser Cys Gln Gly Asp Ser Gly Gly Pro Leu Val Cys Phe Glu Lys
        195                 200                 205 gac aaa tac att tta caa gga gtc act tct tgg ggt ctt ggc tgt gca     672
Asp Lys Tyr Ile Leu Gln Gly Val Thr Ser Trp Gly Leu Gly Cys Ala
    210                 215                 220 cgc ccc aat aag cct ggt gtc tat gtt cgt gtt tca agg ttt gtt act     720
Arg Pro Asn Lys Pro Gly Val Tyr Val Arg Val Ser Arg Phe Val Thr
225                 230                 235                 240 tgg att gag gga gtg atg aga aat aat taa                             750
Trp Ile Glu Gly Val Met Arg Asn Asn
                245
```

<210> SEQ ID NO 4
<211> LENGTH: 249
<212> TYPE: PRT
<213> ORGANISM: Homo sapiens

<400> SEQUENCE: 4

```
Ala Pro Ser Phe Asp Cys Gly Lys Pro Gln Val Glu Pro Lys Lys Cys
1               5                   10                  15
```

```
Pro Gly Arg Val Val Gly Gly Cys Val Ala His Pro His Ser Trp Pro
             20                  25                  30

Trp Gln Val Ser Leu Arg Thr Arg Phe Gly Met His Cys Gly Gly
         35                  40                  45

Thr Leu Ile Ser Pro Glu Trp Val Leu Thr Ala Ala His Cys Leu Glu
     50                  55                  60

Lys Ser Pro Arg Pro Ser Ser Tyr Lys Val Ile Leu Gly Ala His Gln
 65                  70                  75                  80

Glu Val Asn Leu Glu Pro His Val Gln Ile Glu Val Ser Arg Leu
                 85                  90                  95

Phe Leu Glu Pro Thr Arg Lys Asp Ile Ala Leu Leu Lys Leu Ser Ser
             100                 105                 110

Pro Ala Val Ile Thr Asp Lys Val Ile Pro Ala Cys Leu Pro Ser Pro
             115                 120                 125

Asn Tyr Val Val Ala Asp Arg Thr Glu Cys Phe Ile Thr Gly Trp Gly
 130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
             165                 170                 175

Arg Val Gln Ser Thr Glu Leu Cys Ala Gly His Leu Ala Gly Gly Thr
             180                 185                 190

Asp Ser Cys Gln Gly Asp Ser Gly Gly Pro Leu Val Cys Phe Glu Lys
         195                 200                 205

Asp Lys Tyr Ile Leu Gln Gly Val Thr Ser Trp Gly Leu Gly Cys Ala
 210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ggggtatctc tcgagaaaag agcacctccg cctgttgtcc tgcttcc          47

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gcagtgggct gcagtcaaca cccactc                               27

<210> SEQ ID NO 7
<211> LENGTH: 1047
<212> TYPE: DNA
<213> ORGANISM: Homo sapiens
<220> FEATURE:
<221> NAME/KEY: CDS
<222> LOCATION: (1)..(1044)

<400> SEQUENCE: 7

| | | |
|---|---|---|
| gca cct ccg cct gtt gtc ctg ctt cca gat gta gag act cct tcc gaa<br>Ala Pro Pro Pro Val Val Leu Leu Pro Asp Val Glu Thr Pro Ser Glu<br>1               5                   10                  15 | 48 |
| gaa gac tgt atg ttt ggg aat ggg aaa gga tac cga ggc aag agg gcg<br>Glu Asp Cys Met Phe Gly Asn Gly Lys Gly Tyr Arg Gly Lys Arg Ala<br>            20                  25                  30 | 96 |
| acc act gtt act ggg acg cca tgc cag gac tgg gct gcc cag gag ccc<br>Thr Thr Val Thr Gly Thr Pro Cys Gln Asp Trp Ala Ala Gln Glu Pro<br>        35                  40                  45 | 144 |
| cat aga cac agc att ttc act cca gag aca aat cca cgg gcg ggt ctg<br>His Arg His Ser Ile Phe Thr Pro Glu Thr Asn Pro Arg Ala Gly Leu<br>    50                  55                  60 | 192 |
| gaa aaa aat tac tgc cgt aac cct gat ggt gat gta ggt ggt ccc tgg<br>Glu Lys Asn Tyr Cys Arg Asn Pro Asp Gly Asp Val Gly Gly Pro Trp<br>65                  70                  75                  80 | 240 |
| tgc tac acg aca aat cca aga aaa ctt tac gac tac tgt gat gtc cct<br>Cys Tyr Thr Thr Asn Pro Arg Lys Leu Tyr Asp Tyr Cys Asp Val Pro<br>                85                  90                  95 | 288 |
| cag tgt gcg gcc cct tca ttt gat tgt ggg aag cct caa gtg gag ccg<br>Gln Cys Ala Ala Pro Ser Phe Asp Cys Gly Lys Pro Gln Val Glu Pro<br>            100                 105                 110 | 336 |
| aag aaa tgt cct gga agg gtt gtg ggg ggt tgt gtg gcc cac cca cat<br>Lys Lys Cys Pro Gly Arg Val Val Gly Gly Cys Val Ala His Pro His<br>        115                 120                 125 | 384 |
| tcc tgg ccc tgg caa gtc agt ctt aga aca agg ttt gga atg cac ttc<br>Ser Trp Pro Trp Gln Val Ser Leu Arg Thr Arg Phe Gly Met His Phe<br>    130                 135                 140 | 432 |
| tgt gga ggc acc ttg ata tcc cca gag tgg gtg ttg act gct gcc cac<br>Cys Gly Gly Thr Leu Ile Ser Pro Glu Trp Val Leu Thr Ala Ala His<br>145                 150                 155                 160 | 480 |
| tgc ttg gag aag tcc cca agg cct tca tcc tac aag gtc atc ctg ggt<br>Cys Leu Glu Lys Ser Pro Arg Pro Ser Ser Tyr Lys Val Ile Leu Gly<br>                165                 170                 175 | 528 |
| gca cac caa gaa gtg aat ctc gaa ccg cat gtt cag gaa ata gaa gtg<br>Ala His Gln Glu Val Asn Leu Glu Pro His Val Gln Glu Ile Glu Val<br>            180                 185                 190 | 576 |
| tct agg ctg ttc ttg gag ccc aca cga aaa gat att gcc ttg cta aag<br>Ser Arg Leu Phe Leu Glu Pro Thr Arg Lys Asp Ile Ala Leu Leu Lys<br>        195                 200                 205 | 624 |
| cta agc agt cct gcc gtc atc act gac aaa gta atc cca gct tgt ctg<br>Leu Ser Ser Pro Ala Val Ile Thr Asp Lys Val Ile Pro Ala Cys Leu<br>    210                 215                 220 | 672 |
| cca tcc cca aat tat gtg gtc gct gac cgg acc gaa tgt ttc atc act<br>Pro Ser Pro Asn Tyr Val Val Ala Asp Arg Thr Glu Cys Phe Ile Thr<br>225                 230                 235                 240 | 720 |
| ggc tgg gga gaa acc caa ggt act ttt gga gct ggc ctt ctc aag gaa<br>Gly Trp Gly Glu Thr Gln Gly Thr Phe Gly Ala Gly Leu Leu Lys Glu<br>                245                 250                 255 | 768 |
| gcc cag ctc cct gtg att gag aat aaa gtg tgc aat cgc tat gag ttt<br>Ala Gln Leu Pro Val Ile Glu Asn Lys Val Cys Asn Arg Tyr Glu Phe<br>            260                 265                 270 | 816 |
| ctg aat gga aga gtc caa tcc acc gaa ctc tgt gct ggg cat ttg gcc<br>Leu Asn Gly Arg Val Gln Ser Thr Glu Leu Cys Ala Gly His Leu Ala<br>        275                 280                 285 | 864 |
| gga ggc act gac agt tgc cag ggt gac agt gga ggt cct ctg gtt tgc<br>Gly Gly Thr Asp Ser Cys Gln Gly Asp Ser Gly Gly Pro Leu Val Cys<br>    290                 295                 300 | 912 |

```
ttc gag aag gac aaa tac att tta caa gga gtc act tct tgg ggt ctt        960
Phe Glu Lys Asp Lys Tyr Ile Leu Gln Gly Val Thr Ser Trp Gly Leu
305                 310                 315                 320 ggc tgt gca cgc ccc aat aag cct ggt gtc tat gtt cgt gtt tca agg       1008
Gly Cys Ala Arg Pro Asn Lys Pro Gly Val Tyr Val Arg Val Ser Arg
                325                 330                 335 ttt gtt act tgg att gag gga gtg atg aga aat aat taa                   1047
Phe Val Thr Trp Ile Glu Gly Val Met Arg Asn Asn
                340                 345
```

<210> SEQ ID NO 8
<211> LENGTH: 348
<212> TYPE: PRT
<213> ORGANISM: Homo sapiens

<400> SEQUENCE: 8

```
Ala Pro Pro Val Val Leu Leu Pro Asp Val Glu Thr Pro Ser Glu
 1               5                  10                  15

Glu Asp Cys Met Phe Gly Asn Gly Lys Gly Tyr Arg Gly Lys Arg Ala
            20                  25                  30

Thr Thr Val Thr Gly Thr Pro Cys Gln Asp Trp Ala Ala Gln Glu Pro
        35                  40                  45

His Arg His Ser Ile Phe Thr Pro Glu Thr Asn Pro Arg Ala Gly Leu
    50                  55                  60

Glu Lys Asn Tyr Cys Arg Asn Pro Asp Gly Asp Val Gly Gly Pro Trp
65                  70                  75                  80

Cys Tyr Thr Thr Asn Pro Arg Lys Leu Tyr Asp Tyr Cys Asp Val Pro
                85                  90                  95

Gln Cys Ala Ala Pro Ser Phe Asp Cys Gly Lys Pro Gln Val Glu Pro
            100                 105                 110

Lys Lys Cys Pro Gly Arg Val Val Gly Gly Cys Val Ala His Pro His
        115                 120                 125

Ser Trp Pro Trp Gln Val Ser Leu Arg Thr Arg Phe Gly Met His Phe
    130                 135                 140

Cys Gly Gly Thr Leu Ile Ser Pro Glu Trp Val Leu Thr Ala Ala His
145                 150                 155                 160

Cys Leu Glu Lys Ser Pro Arg Pro Ser Ser Tyr Lys Val Ile Leu Gly
                165                 170                 175

Ala His Gln Glu Val Asn Leu Glu Pro His Val Gln Glu Ile Glu Val
            180                 185                 190

Ser Arg Leu Phe Leu Glu Pro Thr Arg Lys Asp Ile Ala Leu Leu Lys
        195                 200                 205

Leu Ser Ser Pro Ala Val Ile Thr Asp Lys Val Ile Pro Ala Cys Leu
    210                 215                 220

Pro Ser Pro Asn Tyr Val Ala Asp Arg Thr Glu Cys Phe Ile Thr
225                 230                 235                 240

Gly Trp Gly Glu Thr Gln Gly Thr Phe Gly Ala Gly Leu Leu Lys Glu
                245                 250                 255

Ala Gln Leu Pro Val Ile Glu Asn Lys Val Cys Asn Arg Tyr Glu Phe
            260                 265                 270

Leu Asn Gly Arg Val Gln Ser Thr Glu Leu Cys Ala Gly His Leu Ala
        275                 280                 285

Gly Gly Thr Asp Ser Cys Gln Gly Asp Ser Gly Gly Pro Leu Val Cys
    290                 295                 300

Phe Glu Lys Asp Lys Tyr Ile Leu Gln Gly Val Thr Ser Trp Gly Leu
305                 310                 315                 320
```

```
Gly Cys Ala Arg Pro Asn Lys Pro Gly Val Tyr Val Arg Val Ser Arg
                325                 330                 335

Phe Val Thr Trp Ile Glu Gly Val Met Arg Asn Asn
            340                 345

<210> SEQ ID NO 9
<211> LENGTH: 2376
<212> TYPE: DNA
<213> ORGANISM: Homo sapiens
<220> FEATURE:
<221> NAME/KEY: CDS
<222> LOCATION: (1)..(2373)

<400> SEQUENCE: 9 gag cct ctg gat gac tat gtg aat acc cag ggg gct tca ctg ttc agt     48
Glu Pro Leu Asp Asp Tyr Val Asn Thr Gln Gly Ala Ser Leu Phe Ser
 1               5                  10                  15 gtc act aag aag cag ctg gga gca gga agt ata gaa gaa tgt gca gca     96
Val Thr Lys Lys Gln Leu Gly Ala Gly Ser Ile Glu Glu Cys Ala Ala
            20                  25                  30 aaa tgt gag gag gac gaa gaa ttc acc tgc agg gca ttc caa tat cac    144
Lys Cys Glu Glu Asp Glu Glu Phe Thr Cys Arg Ala Phe Gln Tyr His
        35                  40                  45 agt aaa gag caa caa tgt gtg ata atg gct gaa aac agg aag tcc tcc    192
Ser Lys Glu Gln Gln Cys Val Ile Met Ala Glu Asn Arg Lys Ser Ser
    50                  55                  60 ata atc att agg atg aga gat gta gtt tta ttt gaa aag aaa gtg tat    240
Ile Ile Ile Arg Met Arg Asp Val Val Leu Phe Glu Lys Lys Val Tyr
65                  70                  75                  80 ctc tca gag tgc aag act ggg aat gga aag aac tac aga ggg acg atg    288
Leu Ser Glu Cys Lys Thr Gly Asn Gly Lys Asn Tyr Arg Gly Thr Met
                85                  90                  95 tcc aaa aca aaa aat ggc atc acc tgt caa aaa tgg agt tcc act tct    336
Ser Lys Thr Lys Asn Gly Ile Thr Cys Gln Lys Trp Ser Ser Thr Ser
            100                 105                 110 ccc cac aga cct aga ttc tca cct gct aca cac cca tca gag gga ctg    384
Pro His Arg Pro Arg Phe Ser Pro Ala Thr His Pro Ser Glu Gly Leu
        115                 120                 125 gag gag aac tac tgc agg aat cca gac aac gat ccg cag ggg ccc tgg    432
Glu Glu Asn Tyr Cys Arg Asn Pro Asp Asn Asp Pro Gln Gly Pro Trp
    130                 135                 140 tgc tat act act gat cca gaa aag aga tat gac tac tgc gac att ctt    480
Cys Tyr Thr Thr Asp Pro Glu Lys Arg Tyr Asp Tyr Cys Asp Ile Leu
145                 150                 155                 160 gag tgt gaa gag gaa tgt atg cat tgc agt gga gaa aac tat gac ggc    528
Glu Cys Glu Glu Glu Cys Met His Cys Ser Gly Glu Asn Tyr Asp Gly
                165                 170                 175 aaa att tcc aag acc atg tct gga ctg gaa tgc cag gcc tgg gac tct    576
Lys Ile Ser Lys Thr Met Ser Gly Leu Glu Cys Gln Ala Trp Asp Ser
            180                 185                 190 cag agc cca cac gct cat gga tac att cct tcc aaa ttt cca aac aag    624
Gln Ser Pro His Ala His Gly Tyr Ile Pro Ser Lys Phe Pro Asn Lys
        195                 200                 205 aac ctg aag aag aat tac tgt cgt aac ccc gat agg gag ctg cgg cct    672
Asn Leu Lys Lys Asn Tyr Cys Arg Asn Pro Asp Arg Glu Leu Arg Pro
    210                 215                 220 tgg tgt ttc acc acc gac ccc aac aag cgc tgg gaa ctt tgc gac atc    720
Trp Cys Phe Thr Thr Asp Pro Asn Lys Arg Trp Glu Leu Cys Asp Ile
225                 230                 235                 240 ccc cgc tgc aca aca cct cca cca tct tct ggt ccc acc tac cag tgt    768
```

```
                Pro Arg Cys Thr Thr Pro Pro Ser Ser Gly Pro Thr Tyr Gln Cys
                                245                 250                 255 ctg aag gga aca ggt gaa aac tat cgc ggg aat gtg gct gtt acc gtt         816
Leu Lys Gly Thr Gly Glu Asn Tyr Arg Gly Asn Val Ala Val Thr Val
            260                 265                 270 tcc ggg cac acc tgt cag cac tgg agt gca cag acc cct cac aca cat         864
Ser Gly His Thr Cys Gln His Trp Ser Ala Gln Thr Pro His Thr His
            275                 280                 285 aac agg aca cca gaa aac ttc ccc tgc aaa aat ttg gat gaa aac tac         912
Asn Arg Thr Pro Glu Asn Phe Pro Cys Lys Asn Leu Asp Glu Asn Tyr
        290                 295                 300 tgc cgc aat cct gac gga aaa agg gcc cca tgg tgc cat aca acc aac         960
Cys Arg Asn Pro Asp Gly Lys Arg Ala Pro Trp Cys His Thr Thr Asn
305                 310                 315                 320 agc caa gtg cgg tgg gag tac tgt aag ata ccg tcc tgt gac tcc tcc        1008
Ser Gln Val Arg Trp Glu Tyr Cys Lys Ile Pro Ser Cys Asp Ser Ser
            325                 330                 335 cca gta tcc acg gaa caa ttg gct ccc aca gca cca cct gag cta acc        1056
Pro Val Ser Thr Glu Gln Leu Ala Pro Thr Ala Pro Pro Glu Leu Thr
            340                 345                 350 cct gtg gtc cag gac tgc tac cat ggt gat gga cag agc tac cga ggc        1104
Pro Val Val Gln Asp Cys Tyr His Gly Asp Gly Gln Ser Tyr Arg Gly
            355                 360                 365 aca tcc tcc acc acc acc aca gga aag aag tgt cag tct tgg tca tct        1152
Thr Ser Ser Thr Thr Thr Thr Gly Lys Lys Cys Gln Ser Trp Ser Ser
    370                 375                 380 atg aca cca cac cgg cac cag aag acc cca gaa aac tac cca aat gct        1200
Met Thr Pro His Arg His Gln Lys Thr Pro Glu Asn Tyr Pro Asn Ala
385                 390                 395                 400 ggc ctg aca atg aac tac tgc agg aat cca gat gcc gat aaa ggc ccc        1248
Gly Leu Thr Met Asn Tyr Cys Arg Asn Pro Asp Ala Asp Lys Gly Pro
            405                 410                 415 tgg tgt ttt acc aca gac ccc agc gtc agg tgg gag tac tgc aac ctg        1296
Trp Cys Phe Thr Thr Asp Pro Ser Val Arg Trp Glu Tyr Cys Asn Leu
            420                 425                 430 aaa aaa tgc tca gga aca gaa gcg agt gtt gta gca cct ccg cct gtt        1344
Lys Lys Cys Ser Gly Thr Glu Ala Ser Val Val Ala Pro Pro Pro Val
            435                 440                 445 gtc ctg ctt cca gat gta gag act cct tcc gaa gaa gac tgt atg ttt        1392
Val Leu Leu Pro Asp Val Glu Thr Pro Ser Glu Glu Asp Cys Met Phe
    450                 455                 460 ggg aat ggg aaa gga tac cga ggc aag agg gcg acc act gtt act ggg        1440
Gly Asn Gly Lys Gly Tyr Arg Gly Lys Arg Ala Thr Thr Val Thr Gly
465                 470                 475                 480 acg cca tgc cag gac tgg gct gcc cag gag ccc cat aga cac agc att        1488
Thr Pro Cys Gln Asp Trp Ala Ala Gln Glu Pro His Arg His Ser Ile
            485                 490                 495 ttc act cca gag aca aat cca cgg gcg ggt ctg gaa aaa aat tac tgc        1536
Phe Thr Pro Glu Thr Asn Pro Arg Ala Gly Leu Glu Lys Asn Tyr Cys
            500                 505                 510 cgt aac cct gat ggt gat gta ggt ggt ccc tgg tgc tac acg aca aat        1584
Arg Asn Pro Asp Gly Asp Val Gly Gly Pro Trp Cys Tyr Thr Thr Asn
            515                 520                 525 cca aga aaa ctt tac gac tac tgt gat gtc cct cag tgt gcg gcc cct        1632
Pro Arg Lys Leu Tyr Asp Tyr Cys Asp Val Pro Gln Cys Ala Ala Pro
        530                 535                 540 tca ttt gat tgt ggg aag cct caa gtg gag ccg aag aaa tgt cct gga        1680
Ser Phe Asp Cys Gly Lys Pro Gln Val Glu Pro Lys Lys Cys Pro Gly
545                 550                 555                 560
```

-continued

| | | |
|---|---|---|
| agg gtt gtg ggg ggg tgt gtg gcc cac cca cat tcc tgg ccc tgg caa<br>Arg Val Val Gly Gly Cys Val Ala His Pro His Ser Trp Pro Trp Gln<br>565                                  570                          575 | 1728 |
| gtc agt ctt aga aca agg ttt gga atg cac ttc tgt gga ggc acc ttg<br>Val Ser Leu Arg Thr Arg Phe Gly Met His Phe Cys Gly Gly Thr Leu<br>580                                  585                          590 | 1776 |
| ata tcc cca gag tgg gtg ttg act gct gcc cac tgc ttg gag aag tcc<br>Ile Ser Pro Glu Trp Val Leu Thr Ala Ala His Cys Leu Glu Lys Ser<br>595                                  600                          605 | 1824 |
| cca agg cct tca tcc tac aag gtc atc ctg ggt gca cac caa gaa gtg<br>Pro Arg Pro Ser Ser Tyr Lys Val Ile Leu Gly Ala His Gln Glu Val<br>610                                  615                          620 | 1872 |
| aat ctc gaa ccg cat gtt cag gaa ata gaa gtg tct agg ctg ttc ttg<br>Asn Leu Glu Pro His Val Gln Glu Ile Glu Val Ser Arg Leu Phe Leu<br>625                                  630                          635                          640 | 1920 |
| gag ccc aca cga aaa gat att gcc ttg cta aag cta agc agt cct gcc<br>Glu Pro Thr Arg Lys Asp Ile Ala Leu Leu Lys Leu Ser Ser Pro Ala<br>                        645                          650                          655 | 1968 |
| gtc atc act gac aaa gta atc cca gct tgt ctg cca tcc cca aat tat<br>Val Ile Thr Asp Lys Val Ile Pro Ala Cys Leu Pro Ser Pro Asn Tyr<br>                        660                          665                          670 | 2016 |
| gtg gtc gct gac cgg acc gaa tgt ttc atc act ggc tgg gga gaa acc<br>Val Val Ala Asp Arg Thr Glu Cys Phe Ile Thr Gly Trp Gly Glu Thr<br>                      675                          680                          685 | 2064 |
| caa ggt act ttt gga gct ggc ctt ctc aag gaa gcc cag ctc cct gtg<br>Gln Gly Thr Phe Gly Ala Gly Leu Leu Lys Glu Ala Gln Leu Pro Val<br>690                                  695                          700 | 2112 |
| att gag aat aaa gtg tgc aat cgc tat gag ttt ctg aat gga aga gtc<br>Ile Glu Asn Lys Val Cys Asn Arg Tyr Glu Phe Leu Asn Gly Arg Val<br>705                                  710                          715                          720 | 2160 |
| caa tcc acc gaa ctc tgt gct ggg cat ttg gcc gga ggc act gac agt<br>Gln Ser Thr Glu Leu Cys Ala Gly His Leu Ala Gly Gly Thr Asp Ser<br>                        725                          730                          735 | 2208 |
| tgc cag ggt gac agt gga ggt cct ctg gtt tgc ttc gag aag gac aaa<br>Cys Gln Gly Asp Ser Gly Gly Pro Leu Val Cys Phe Glu Lys Asp Lys<br>740                                  745                          750 | 2256 |
| tac att tta caa gga gtc act tct tgg ggt ctt ggc tgt gca cgc ccc<br>Tyr Ile Leu Gln Gly Val Thr Ser Trp Gly Leu Gly Cys Ala Arg Pro<br>755                                  760                          765 | 2304 |
| aat aag cct ggt gtc tat gtt cgt gtt tca agg ttt gtt act tgg att<br>Asn Lys Pro Gly Val Tyr Val Arg Val Ser Arg Phe Val Thr Trp Ile<br>770                                  775                          780 | 2352 |
| gag gga gtg atg aga aat aat taa<br>Glu Gly Val Met Arg Asn Asn<br>785                                  790 | 2376 |

<210> SEQ ID NO 10
<211> LENGTH: 791
<212> TYPE: PRT
<213> ORGANISM: Homo sapiens

<400> SEQUENCE: 10

Glu Pro Leu Asp Asp Tyr Val Asn Thr Gln Gly Ala Ser Leu Phe Ser
1                 5                       10                       15

Val Thr Lys Lys Gln Leu Gly Ala Gly Ser Ile Glu Glu Cys Ala Ala
                 20                       25                       30

Lys Cys Glu Glu Asp Glu Glu Phe Thr Cys Arg Ala Phe Gln Tyr His
                 35                       40                       45

Ser Lys Glu Gln Gln Cys Val Ile Met Ala Glu Asn Arg Lys Ser Ser
        50                       55                       60

-continued

```
Ile Ile Ile Arg Met Arg Asp Val Val Leu Phe Glu Lys Lys Val Tyr
 65                  70                  75                  80

Leu Ser Glu Cys Lys Thr Gly Asn Gly Lys Asn Tyr Arg Gly Thr Met
             85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
        130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
        290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
            325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
            355                 360                 365

Thr Ser Ser Thr Thr Thr Gly Lys Lys Cys Gln Ser Trp Ser Ser
        370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
            435                 440                 445

Val Leu Leu Pro Asp Val Glu Thr Pro Ser Glu Glu Asp Cys Met Phe
            450                 455                 460

Gly Asn Gly Lys Gly Tyr Arg Gly Lys Arg Ala Thr Thr Val Thr Gly
465                 470                 475                 480
```

```
Thr Pro Cys Gln Asp Trp Ala Ala Gln Glu Pro His Arg His Ser Ile
            485                 490                 495

Phe Thr Pro Glu Thr Asn Pro Arg Ala Gly Leu Glu Lys Asn Tyr Cys
        500                 505                 510

Arg Asn Pro Asp Gly Asp Val Gly Gly Pro Trp Cys Tyr Thr Thr Asn
        515                 520                 525

Pro Arg Lys Leu Tyr Asp Tyr Cys Asp Val Pro Gln Cys Ala Ala Pro
        530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
                580                 585                 590

Ile Ser Pro Glu Trp Val Leu Thr Ala Ala His Cys Leu Glu Lys Ser
            595                 600                 605

Pro Arg Pro Ser Ser Tyr Lys Val Ile Leu Gly Ala His Gln Glu Val
        610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
                660                 665                 670

Val Val Ala Asp Arg Thr Glu Cys Phe Ile Thr Gly Trp Gly Glu Thr
            675                 680                 685

Gln Gly Thr Phe Gly Ala Gly Leu Leu Lys Glu Ala Gln Leu Pro Val
        690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
        770                 775                 780

Glu Gly Val Met Arg Asn Asn
785                 790

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:
      Illustrative RGD containing peptide

<400> SEQUENCE: 11

Gly Arg Gly Asp Ser
  1               5

<210> SEQ ID NO 12
<211> LENGTH: 6
<212> TYPE: PRT
<213> ORGANISM: Artificial Sequence
```

```
<220> FEATURE:
<223> OTHER INFORMATION: Description of Artificial Sequence:
      Illustrative RGD containing peptide

<400> SEQUENCE: 12

Gly Arg Gly Asp Thr Pro
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6-His tag

<400> SEQUENCE: 13

His His His His His His
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 14

Glu Lys Arg Glu Ala Glu Ala
 1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 15

Leu Glu Lys Arg
 1
```

PHARMACOLOGICAL VITREOLYSIS

CROSS REFERENCE TO RELATED APPLICATIONS

This application is a continuation of U.S. application Ser. No. 12/156,907, filed Jun. 5, 2008, entitled "Pharmacological Vitreolysis", which is a continuation of U.S. application Ser. No. 10/729,475, entitled, "Pharmacological Vitreolysis," filed Dec. 5, 2003, which in turn claims the benefit of priority to Great Britain Application No. 0228409.9 filed Dec. 6, 2002, the contents of both of which are herein incorporated by reference in their entirety.

FIELD OF THE INVENTION

The present invention relates generally to methods of treating or preventing a disorder, or a complication of a disorder, of the mammalian eye. More specifically, the present invention relates to the use of a truncated plasmin protein comprising a catalytic domain in methods of treating or preventing a disorder, or a complication of a disorder, of the mammalian eye.

BACKGROUND OF THE INVENTION

The adult human eye is a slightly asymmetrical sphere with an approximate sagittal diameter of 24 to 25 mm, a transverse diameter of 24 mm, and a volume of about 6.5 cc. The human eye can be divided into three different layers namely, an external layer, an intermediate layer and an internal layer. The external layer of the eye consists of the sclera, which is often referred to as the "white of the eye," and the cornea, which covers the front of the eye. The intermediate layer is divided into an anterior portion and a posterior portion; the anterior portion consists of the circular pigmented iris, the crystalline lens and ciliary body, while the posterior portion consists of the choroid layer. The internal layer consists of the retina, which is the sensory part of the eye. The retina is essentially a layer of nervous tissue, which runs along the inside rear surface of the choroid layer and can be divided into an optic portion and a non-optic portion. The optic portion, which participates in the visual mechanism, contains the rods and cones that are the effectual organs of vision.

The human eye can also be divided into three chambers. The anterior chamber between the cornea and the iris, and the posterior chamber between the iris and the crystalline lens, are filled with aqueous humor. In contrast, the vitreous chamber between the crystalline lens and the retina is filled with a more viscous liquid, called the vitreous (also known as the vitreous body or vitreous humor). The vitreous humor in a normal eye is a clear gel occupying about 80% of the volume of the eyeball. Light that enters the eye through the cornea, pupil, and lens, is transmitted through the vitreous to the retina.

The vitreous humor of a normal human eye is a gel that is roughly 99% water and 1% macromolecules. These macromolecules include a network of collagen fibrils, hyaluronic acid, soluble glycoproteins, sugars and other low molecular weight metabolites. Type II collagen is the principal fibrillar collagen of the vitreous, but the vitreous also contains collagen types V, IX, and XI. The posterior portion of the vitreous body, the posterior hyaloid surface (also known as the posterior vitreous cortex), is in direct contact with the inner retinal surface most prominently at the vitreous base, optic disc, and along the major retinal vessels. Normal adhesion of the vitreous to the retina is mediated by cellular and molecular interactions between the posterior vitreous cortex and the inner limiting membrane (ILM) of the retina. The ILM is essentially the basement membrane of retinal Mueller cells. The ILM contains collagen types I and IV, glycoproteins such as laminin and fibronectin and other glycoconjugates. These components are thought to bridge and bind collagen fibers between the vitreous and the ILM.

With age, the vitreous humor changes from gel to liquid and as it does so it gradually shrinks and separates from the ILM of the retina. This process is known as "posterior vitreous detachment" (PVD) and is a normal occurrence after age 40. However, degenerative changes in the vitreous may also be induced by pathological conditions such as diabetes, Eale's disease and uveitis. Also, PVD may occur earlier than normal in nearsighted people and in those who have had cataract surgery. Usually, the vitreous makes a clean break from the retina. Occasionally, however, the vitreous adheres tightly to the retina in certain places. These small foci of resisting, abnormally firm attachments of the vitreous can transmit great tractional forces from the vitreous to the retina at the attachment site. This persistent tugging by the vitreous often results in horseshoe-shaped tears in the retina. Unless the retinal tears are repaired, vitreous fluid can seep through this tear into or underneath the retina and cause a retinal detachment, a very serious, sight-threatening condition. In addition, persistent attachment between the vitreous and the ILM can result in bleeding from rupture of blood vessels, which results in the clouding and opacification of the vitreous.

The development of an incomplete PVD has an impact on many vitreoretinal diseases including vitreomacular traction syndrome, vitreous hemorrhage, macular holes, macular edema, diabetic retinopathy, diabetic maculopathy and retinal detachment. Thus, an important goal of vitreous surgery is to separate the vitreous from the retina in a manner that prevents vitreous traction.

In order to remove the vitreous from the eye, a microsurgical procedure called vitrectomy is usually performed. In this procedure the vitreous is removed from the eye with a miniature handheld cutting device while simultaneously replacing the removed vitreous with saline solution to prevent collapse of the eye. Surgical removal of the vitreous using this method is highly skill-dependent, and complete removal of the cortical vitreous remains a difficult task. Furthermore, mechanical vitrectomy carries the risk of complications such as scarring, tearing and other damage to the retina. Obviously, such damage is highly undesirable as it can compromise the patient's vision after surgery.

Thus, alternative methods to remove the vitreous from the retina have been the focus of recent investigation. Such methods have explored the use of enzymes and chemical substances, which can be used to induce/promote liquefaction of the vitreous and/or separation of the vitreoretinal interface (PVD). These approaches, which are referred to as "pharmacological vitrectomy," have included several proteolytic enzymes such as alpha-chymotrypsin, hyaluronidase, bacterial collagenase, chondroitinase and dispase, which have been injected intravitreally in experimental and/or clinical trials to induce PVD. However, most of these techniques do not release the posterior hyaloid from the ILM completely or without complications. In addition, in several of these cases, the risk of adverse reactions is high. For example, the use of bacterial proteases in mammalian systems generates an immune response, which leads to proliferative vitreoretinopathy resulting in complex retinal re-detachment. Collagenase has been reported to liquefy the vitreous, but it has also been shown to disrupt the outer layers of the retina. Alpha-chymotrypsin has been reported to produce peripapillary and vitreous hemorrhage in the injected eyes. Finally, dispase has been reported to cause toxicity to the inner layer of the retina 15 minutes after injection. Depending on the concentration of dispase used, proliferative retinopathy or epiretinal cellular membranes can develop in the injected eyes.

Given the immunogenicity and other adverse effects of bacterial proteases, pharmacological vitreolysis using endogenous human derived proteases may be desirable. Plasmin is a serine protease derived from plasminogen. Plasminogen is an important component of mammalian blood. Human plasminogen is a single chain glycoprotein consisting of 791 amino acids, which has a molecular weight of about 92,000 daltons (see Forsgren M. et al., *FEBS Lett.* 213(2):254-60, 1987). Native plasminogen with an amino-terminal glutamic acid (termed "Glu-plasminogen") is converted by limited digestion by plasmin of the $Arg_{68}$-$Met_{69}$, $Lys_{77}$-$Lys_{78}$, or $Lys_{78}$-$Val_{79}$ peptide bonds to proteins commonly designated as "Lys-plasminogen." Activation of plasminogen by plasminogen activators such as urokinase or streptokinase, cleaves the peptide bond between $Arg_{561}$ and $Val_{562}$ converting the plasminogen molecule into a double chain, enzymatically active form called plasmin. Plasmin contains two polypeptides, a heavy A chain connected by two disulphide bonds to a light B chain; the B chain contains the serine protease catalytic domain. The serine protease catalytic activity of plasmin has been implicated in its ability to dissolve blood clots in vivo.

Recently, plasmin has also been suggested as an adjunct for vitrectomy. In addition, autologous plasmin enzyme (APE) has been suggested as an agent for pharmacological vitrectomy. However, there are several disadvantages associated with the use of plasmin. First, so far all clinical interventions with plasmin have relied on the use of APE, the isolation of which necessitates a laborious and time-consuming process involving drawing of a patient's blood, isolation of plasminogen, activation of the isolated plasminogen to plasmin, and purification and sterility testing of the plasmin enzyme. Furthermore, this procedure can be costly and the presence of blood-borne pathogens can further complicate this procedure. Also, plasmin is highly prone to degradation and thus cannot be stored for prolonged periods prior to its use. A further disadvantage is plasmin's large molecular weight, which ranges between 65,000 and 83,000 daltons. Thus, the diffusion of large molecules like plasmin from its injected position in the vitreous to the vitreoretinal interface would be hindered compared to smaller molecules.

Accordingly, there is a need in the art for methods of treating or preventing disorders, or complications of disorders, of the eye of a subject that overcome the disadvantages of plasmin, for pharmacological vitreolysis. Specifically, there is a need for methods of treating or preventing a disorder, or a complication of a disorder, of the eye using smaller molecules than plasmin, which can diffuse through the vitreous to the vitreoretinal interface faster than plasmin, and which can be readily obtained in large quantities without the delay and other attendant problems of isolating autologous plasmin enzyme on a patient-by-patient basis.

SUMMARY OF THE INVENTION

The present invention provides methods of treating or preventing a disorder, or a complication of a disorder, of the eye of a subject using a composition comprising a truncated plasmin protein comprising a catalytic domain of plasmin (TPCD). In one embodiment, a TPCD is selected from the group consisting of miniplasmin, recombinant miniplasmin, stabilized miniplasmin, stabilized, recombinant miniplasmin, variants of miniplasmin, microplasmin, recombinant microplasmin, stabilized microplasmin, stabilized, recombinant microplasmin, variants of microplasmin, and any combinations thereof.

The present invention also provides methods of treating or preventing a disorder, or a complication of a disorder, of the eye of a subject using a composition comprising a modified TPCD. A modified TPCD is a TPCD, which comprises a modified catalytic domain of plasmin.

The present invention provides methods of treating or preventing a disorder, or a complication of a disorder, of the eye of a subject by contacting a vitreous and/or an aqueous humor of the subject with a composition comprising a TPCD. The present invention provides methods of treating or preventing eye disorders such as, but not limited to, retinal detachment, retinal tear, vitreous hemorrhage, diabetic vitreous hemorrhage, proliferative diabetic retinopathy, non-proliferative diabetic retinopathy, age-related macular degeneration, macular holes, vitreomacular traction, macular pucker, macular exudates, cystoid macular edema, fibrin deposition, retinal vein occlusion, retinal artery occlusion, subretinal hemorrhage, amblyopia, endophthalmitis, retinopathy of prematurity, glaucoma, retinitis pigmentosa and any combinations thereof. The methods of the invention can be practiced independent of vitrectomy, or as an adjunct to vitrectomy.

The present invention also provides methods of treatment or prevention of an eye disorder, or a complication of an eye disorder, of a subject comprising administering to the subject a composition comprising at least two TPCDs. In one embodiment of this aspect of the invention, a composition is administered to a subject by contacting a vitreous and/or an aqueous humor with a composition comprising at least two TPCDs.

The present invention further encompasses methods of treatment or prevention of an eye disorder, or a complication of an eye disorder, comprising providing a subject with a first composition comprising at least one TPCD, and a second composition comprising at least one TPCD. In one embodiment of this aspect of the invention, a first composition comprising at least one TPCD and a second composition comprising at least one TPCD are provided to a subject by contacting a vitreous and/or an aqueous humor. In another embodiment of this aspect of the invention, the TPCDs of the first composition comprising at least one TPCD and the second composition comprising at least one TPCD are the same TPCD. In yet another embodiment of this aspect of the invention, the TPCDs of the first composition comprising at least one TPCD and the second composition comprising at least one TPCD are different TPCDs. In a further embodiment of this aspect of the invention, the first composition comprising at least one TPCD and the second composition comprising at least one TPCD are administered to a subject at substantially the same time. In yet another embodiment, the first composition comprising at least one TPCD and the second compositions composition comprising at least one TPCD are administered to a subject at separate times.

The present invention additionally provides methods of treatment or prevention of an eye disorder, or a complication of an eye disorder, of a subject by administering a composition comprising at least one TPCD and at least one second agent to the subject. A second agent includes any substance that is useful either alone, or in combination with a TPCD, in treating or preventing an eye disorder or a complication of an eye disorder. A second agent, includes without limitation, hyaluronidase, dispase, chondroitinase, collagenase, RGD containing peptides, anti-integrin antibody, urea, hydroxyurea, thiourea, P2Y receptor agonists, and any angiogenic inhibitors including, but not limited to, VEGF inhibitors and PlGF inhibitors.

The present invention also encompasses methods of treatment or prevention of an eye disorder, or a complication of an eye disorder, of a subject by administering to the subject a composition comprising at least one TPCD prior to or after administration of a composition comprising a second agent.

The methods of the invention can be used to treat or prevent an eye disorder, or a complication of an eye disorder, of a subject by effecting one or more outcomes including, but not limited to, reducing the viscosity of the vitreous, liquefying the vitreous, inducing posterior vitreous detachment, clearing or reducing hemorrhagic blood from the vitreous and/or aqueous humor, clearing or reducing intraocular foreign substances from the vitreous and/or aqueous humor, clearing or reducing materials toxic to the retina, increasing diffusion of an agent or a composition administered to the vitreous and/or aqueous humor, reducing extraretinal neovascularization and any combinations thereof.

The present invention also provides methods of performing a vitrectomy comprising contacting the vitreous of a subject with a composition comprising a TPCD. The contacting step can be performed prior to or at the same time as the vitrectomy or independent of vitrectomy.

The present invention also provides a composition comprising at least two TPCDs.

The present invention further provides a composition comprising at least one TPCD and at least one second agent.

BRIEF DESCRIPTION OF THE DRAWINGS

FIGS. 1 A-D provide the DNA (SEQ ID NO:9) and amino acid sequence (SEQ ID NO:10) of human plasminogen.

FIGS. 2A-B provide the DNA (SEQ ID NO:3) and amino acid sequence (SEQ ID NO:4) of human microplasminogen.

FIGS. 3A-B provide the DNA (SEQ ID NO:7) and amino acid sequence (SEQ ID NO:8) of human miniplasminogen.

DETAILED DESCRIPTION OF THE INVENTION

Figure 4:
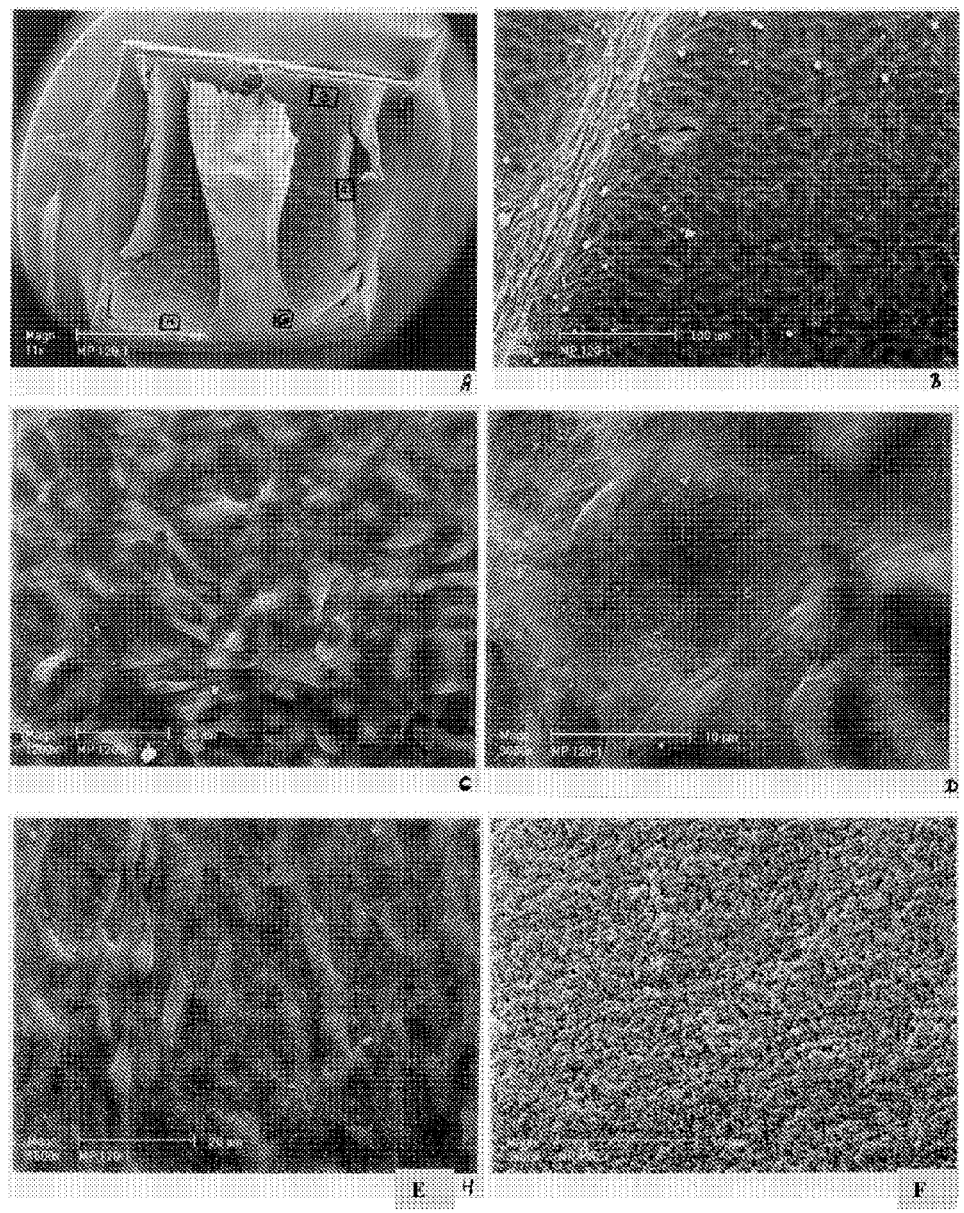
FIG. 4 shows the effect of treating porcine eyes with microplasmin. Panel A is a low magnification image (11×) of the mid-peripheral retina after slow dehydration of a porcine eye treated with 0.125 mg of microplasmin in 0.1 ml BSS PLUS® for 120 minutes. In the centre of this image, is a vitreous strand. It is likely that this vitreous strand is vitreous that has collapsed onto the retinal surface. Most of the retinal surface is free of vitreous as shown in the remaining panels. Panel B shows an area of bare retina adjacent to a blood vessel (magnification 800×). Few cells are seen on the retinal surface. The irregular surface is that of the vessel itself Panel C and D are magnifications of the retinal area in B at 1200× and 3600× magnification respectively showing a smooth retinal surface largely devoid of vitreous or cellular material. At 3600× only a few fibrillar strands are visible. Panel E is an image at a magnification of 1500× essentially showing the same findings as in Panel C at a more central retinal location, while panel F shows the coarse granular structure of the vitreous, which has lost its fibrillar structure. The structure of the vitreous in the microplasmin treated eyes is very different in appearance compared to the vitreous in control eyes (data not shown).

The patent applications, patents, and literature references cited herein indicate the knowledge of those of ordinary skill in this field and are hereby incorporated by reference in their entirety. In the case of inconsistencies between any reference cited herein and the specific teachings of the present disclosure, this disclosure will prevail.

The following detailed description and the accompanying examples are provided for purposes of describing and explaining only certain preferred embodiments of the invention, and are not intended to limit the scope of the invention in any way. Unless defined otherwise, all technical and scientific terms used herein have the same meanings as commonly understood by one of ordinary skill in the art to which this invention belongs.

Prior to setting forth the invention in detail, it may be helpful to an understanding thereof to set forth definitions of certain terms that will be used hereafter.

Definitions

"treating," means the reduction or amelioration of any medical disorder to any extent, and includes, but does not require, a complete cure of the disorder.

"preventing" means to defend or protect against the development of a disorder, i.e., to function as a prophylactic.

"disorder" means any disease, dysfunction, syndrome, condition, pain, or any combination thereof. Disorder also includes any complications from any disease, dysfunction, syndrome, condition, pain or any combination thereof "subject" means any mammal, particularly a human.

"contacting" means any mode of administration that results in interaction between a composition and an object being contacted (e.g., vitreous, aqueous humor, etc.). The interaction of the composition with the object being contacted can occur at substantially the same time as the administration of the composition, over an extended period of time starting from around the time of administration of the composition, or be delayed from the time of administration of the composition.

"composition" means a combination or mixture of one or more substances.

"substance" means that which has mass and occupies space.

"foreign substance" means any substance that is determined by a medical doctor, clinician, veterinarian or researcher to be harmful or toxic to the eye of a subject and/or to be a substance that is not normally found in a healthy mammalian eye.

"ophthalmologically acceptable carrier" is a substance with which a second substance (for e.g., a TPCD) can be combined, without making the second substance unsuitable (as determined by a medical doctor, clinician, veterinarian or researcher) for its intended use in the eye of a subject. Non-limiting examples of an ophthalmologically acceptable carrier include balanced salt solution (BSS) and BSS-PLUS®.

"pharmaceutically acceptable carrier" includes, without limitation, water, buffered saline, polyol (for e.g., glycerol, propylene glycol, liquid polyethylene glycol), or suitable mixtures thereof. Other examples of pharmaceutically acceptable carriers and methods for making such carriers and formulations thereof are found, for example, in *Remington's Pharmaceutical Sciences* (20th Edition, A. Gennaro (ed.), Lippincott, Williams & Wilkins, 2000).

"an effective amount" means an amount of a substance or composition that elicits a response in an eye of a human or other mammal that is being sought by a researcher, veterinarian, medical doctor or other clinician.

"inducing" means to bring about or stimulate the occurrence of a desired result.

"reduce" means to decrease to any extent.

"toxic effects to the eye" means any adverse effect to the eye of a subject that is determined to be harmful to the subject by a researcher, veterinarian, medical doctor or other clinician.

"vitreous" means the vitreous humor, also referred to as the vitreous body, which occupies the chamber between the crystalline lens of the eye and the retina.

"TPCD" is an acronym for "truncated plasmin protein comprising a catalytic domain of plasmin." A "truncated plasmin protein" means any plasmin protein obtained by deleting one or more amino acids of $Val_{79}$-plasmin (i.e., amino acids 79-791 of human plasminogen), wherein the resulting protein possesses serine protease catalytic activity. Such amino acid deletions can be at the N-terminus (resulting in TPCDs consisting for example of, amino acids 444-791, 543-791, or 562-791 of SEQ ID NO:10) and/or at the C-terminus and/or at any internal position or positions of amino acids 79-791 of SEQ ID NO:10. It is to be understood that if a truncated protein derived from SEQ ID NO:10 is made as an enzymatically inactive form, it must be activated using a plasminogen activator to convert it into the corresponding active form of the truncated protein. For example, if a protein consisting of amino acids 543-791 of SEQ ID NO:10 is made recombinantly, it is highly likely that the protein will not be in its enzymatically active form. Thus, the protein should be treated with a plasminogen activator to cleave the peptide bond between $Arg_{561}$ and $Val_{562}$, thereby activating the protein. Non-limiting examples of a TPCD include miniplasmin, recombinant miniplasmin, stabilized miniplasmin, stabilized, recombinant miniplasmin, variants of miniplasmin, microplasmin, recombinant microplasmin, stabilized microplasmin, stabilized, recombinant microplasmin and variants of microplasmin wherein, the variants of microplasmin and miniplasmin include a catalytic domain of plasmin.

"plasmin protein" means any protein made or derived from the amino acid sequence of human plasminogen (SEQ ID NO:10) that has a cleavage of the peptide bond between Arg$_{561}$ and Val$_{562}$ of human plasminogen. The cleavage of the peptide bond between Arg$_{561}$ and Val$_{562}$ can be accomplished using plasminogen activators. Non-limiting examples of plasmin proteins include Lys-plasmin, miniplasmin and microplasmin.

"catalytic domain of plasmin" means an amino acid sequence of about 130-240 amino acids derived from amino acids 543 to 791 of SEQ ID NO:10 (human plasminogen), which includes the catalytic triad of plasmin namely, His$_{603}$, Asp$_{646}$ and Ser$_{741}$, wherein the amino acid sequence possesses serine protease activity.

"modified catalytic domain of plasmin" means a catalytic domain of plasmin that has been altered by changing the amino acid sequence of the catalytic domain by addition and/or deletion and/or substitution of one or more amino acids. Of course it is to be understood that the amino acids corresponding to the catalytic triad of plasmin namely, His$_{603}$, Asp$_{646}$ and Ser$_{741}$, are not altered. The modification may increase, decrease or leave unchanged the plasmin-like catalytic activity of the protein. For example, the modified catalytic domain of microplasmin and miniplasmin may increase, decrease or leave unchanged the catalytic activity of these proteins.

"modified TPCD" is a TPCD containing a modified catalytic domain of plasmin, wherein the TPCD possesses plasmin-like serine protease catalytic activity.

"second agent" means any substance that can be used, either by itself, or in combination with a TPCD, in treating or preventing an eye disorder or a complication of an eye disorder of a subject. Preferably the second agent does not prevent the catalytic activity of a TPCD.

"stabilizing a protein" means protecting a protein from degradation and/or inactivation through the use of one or more stabilizing agents.

Although any methods and materials similar or equivalent to those described herein can be used in the practice or testing of the present invention, the preferred methods and materials are described below.

Pharmacological vitreolysis is a method of using one or more proteinaceous and/or chemical and/or nucleic acid agents to treat or prevent a disorder, or a complication of a disorder, of an eye of a subject. The present invention provides methods of pharmacological vitreolysis using at least one truncated plasmin protein comprising a catalytic domain (TPCD). Specifically, the present invention provides methods of treatment or prevention of eye disorders, or complications of eye disorders, by contacting the vitreous and/or aqueous humor with an effective amount of a composition comprising a TPCD. These methods results in outcomes such as, but not limited to, liquefaction of the vitreous, posterior vitreous detachment, reduction or clearing of hemorrhagic blood from the vitreous and/or aqueous humor, reduction or clearing of intraocular foreign substances from the vitreous and/or aqueous humor, increasing diffusion of an agent or composition administered to the vitreous and/or aqueous humor, decreasing extraretinal neovascularization, and any combinations thereof. These methods may be used either as an adjunct to vitrectomy, or in the absence of vitrectomy.

Accordingly, the present invention provides, as a first aspect, a method of treating or preventing a disorder, or a complication of a disorder, of the eye of a subject comprising contacting the vitreous and/or aqueous humor with an effective amount of a composition comprising a TPCD. In one embodiment, a TPCD has a molecular weight less than about 40,000 daltons. In another embodiment, a TPCD has a molecular weight of about 26,500 daltons in reduced form or about 29,000 daltons in non-reduced form. In yet another embodiment a TPCD has a molecular weight of between about 20,000 and 30,000 daltons. In a further embodiment, a TPCD has a molecular weight of less than about 20,000 daltons.

In a second aspect, the present invention provides a method of treating or preventing a disorder, or a complication of a disorder, of the eye of a subject comprising contacting the vitreous and/or aqueous humor with an effective amount of a composition comprising at least two TPCDs.

In a third aspect, the present invention provides a method of treating or preventing a disorder, or a complication of a disorder, of the eye of a subject comprising contacting the vitreous and/or aqueous humor with an effective amount of a first composition comprising at least one TPCD and an effective amount of a second composition comprising at least one TPCD. In one embodiment of this aspect of the invention, the first composition comprising at least one TPCD and the second composition comprising at least one TPCD can comprise the same TPCD In another embodiment of this aspect of the invention, the first composition comprising at least one TPCD and the second composition comprising at least one TPCD can comprise different TPCDs. In a further embodiment of this aspect of the invention, the first and second compositions may be administered to a subject at substantially the same time or at different times.

In a fourth aspect, the present invention provides a method of treating or preventing a disorder, or a complication of a disorder, of the eye of a subject comprising contacting the vitreous and/or aqueous humor with an effective amount of a composition comprising at least one TPCD and at least one second agent. In this aspect of the invention, the second agent is not intended to be a TPCD.

In a fifth aspect, the present invention provides a method of treating or preventing a disorder, or a complication of a disorder, of the eye of a subject comprising contacting the vitreous and/or aqueous humor with an effective amount of a composition comprising at least one TPCD prior to, at the same time as, or after contacting the vitreous and/or aqueous humor with an effective amount of a composition comprising at least one second agent.

In a sixth aspect, the present invention provides a method of liquefying the vitreous comprising contacting the vitreous and/or aqueous humor with an effective amount of a composition comprising at least one TPCD. In one embodiment of this aspect of the invention, the liquefaction of the vitreous decreases the viscosity of the vitreous humor. In other embodiments of the invention, the liquefaction of the vitreous increases the rate of clearance from the vitreous cavity and/or aqueous humor of blood, deposited material, foreign substances and/or materials toxic to the eye, especially the retina. In another embodiment of this aspect of the invention, the liquefaction of the vitreous decreases extraretinal neovascularization. In yet another embodiment of this aspect of the invention, the liquefaction of the vitreous increases the diffusion of an agent or composition administered to the vitreous and/or aqueous humor. In a further embodiment of this aspect of the invention, the liquefaction of the vitreous helps in the removal of the vitreous during standard vitrectomy or 25 Gauge (or smaller) vitrectomy.

In a seventh aspect, the present invention provides a method of inducing posterior vitreous detachment comprising contacting the vitreous and/or aqueous humor with an effective amount of a composition comprising at least one TPCD.

In any of the first to seventh aspects of the invention described above, the step of contacting the vitreous and/or aqueous humor with a composition comprising a TPCD can be performed as an adjunct to, or in the absence of vitrectomy.

In an eighth aspect, the present invention provides a method of performing a vitrectomy comprising the step of contacting the vitreous and/or aqueous humor with a composition comprising at least one TPCD. The contacting step can be performed at the same time as, or prior to vitrectomy.

In a ninth aspect, the present invention provides a composition comprising at least two TPCDs.

In a tenth aspect, the present invention provides a composition comprising at least one TPCD and at least one second agent.

In one embodiment of all aspects of the present invention, a TPCD is selected from the group consisting of miniplasmin, recombinant miniplasmin, stabilized miniplasmin, stabilized, recombinant miniplasmin, variants of miniplasmin, microplasmin, recombinant microplasmin, stabilized microplasmin, stabilized, recombinant microplasmin, variants of microplasmin, and any combinations thereof. In another embodiment of all aspects of the invention, the methods of treatment or prevention of an eye disorder, or complications of an eye disorder, and methods of performing a vitrectomy result in the amelioration of an eye disorder by one or more of the following outcomes: reducing the viscosity of the vitreous, liquefying the vitreous, inducing posterior vitreous detachment, clearing or reducing hemorrhagic blood from the vitreous, vitreous cavity and/or aqueous humor, clearing or reducing intraocular foreign substances from the vitreous, vitreous cavity and/or aqueous humor, clearing or reducing materials toxic to the retina from the vitreous, vitreous cavity and/or aqueous humor, increasing the diffusion of an agent or a composition administered to the vitreous and/or aqueous humor, or reducing retinal neovascularization. In yet another embodiment of all aspects of the invention, the eye disorder or complication of an eye disorder sought to be treated or prevented is selected from the group consisting of retinal detachment, retinal tear, vitreous hemorrhage, diabetic vitreous hemorrhage, proliferative diabetic retinopathy, non-proliferative diabetic retinopathy, age-related macular degeneration, macular holes, vitreomacular traction, macular pucker, macular exudates, cystoid macular edema, fibrin deposition, retinal vein occlusion, retinal artery occlusion, subretinal hemorrhage, amblyopia, endophthalmitis, retinopathy of prematurity, glaucoma, retinitis pigmentosa, and any combination thereof.

A TPCD includes any truncated plasmin protein comprising a catalytic domain of plasmin. A truncated plasmin protein encompasses any plasmin protein obtained by deleting one or more amino acids of $Val_{79}$-plasmin (i.e., amino acids 79-791 of human plasminogen), wherein the resulting protein possesses serine protease catalytic activity. Thus, all TPCDs must contain the catalytic triad of the plasmin serine protease domain namely, $His_{603}$, $Asp_{646}$ and $Ser_{741}$. Truncations of $Val_{79}$-plasmin can be made by deletions of one or more amino acids in amino acids 79-791 of SEQ ID NO:10 (human plasminogen). Such deletions can be at the N-terminus, C-terminus or at an internal location of amino acids 79-791 of SEQ ID NO:10. It should be understood that if a protein resulting from a truncation of amino acids 79-791 of SEQ ID NO:10 (human plasminogen) is made in an enzymatically inactive form, the protein must be converted to its active form using a plasminogen activator, to be considered a TPCD. Plasminogen activators cleave the peptide bond between $Arg_{561}$ and $Val_{562}$, thereby activating a protein. In one embodiment a TPCD includes proteins consisting essentially of amino acids 444-791 of SEQ ID NO:10. In another embodiment, a TPCD includes proteins with one or more amino acid deletions in amino acids 444-791 of human plasminogen, wherein the resulting protein possesses serine protease catalytic activity. In another embodiment, a TPCD includes proteins consisting essentially of amino acids 543-791 of SEQ ID NO:10. In yet another embodiment a TPCD includes proteins with one or more deletions in amino acids 543-791 of human plasminogen, wherein the resulting protein possesses serine protease catalytic activity. In another embodiment, a TPCD includes proteins consisting essentially of amino acids 562-791 of SEQ ID NO:10. In another embodiment a TPCD includes proteins with one or more deletions in amino acids 562-791 of human plasminogen, wherein the resulting protein possesses serine protease catalytic activity. The deletions can be at the N-terminus, C-terminus or at an internal location of amino acids 444-791, 543-791 and 562-791 of SEQ ID NO:10 (human plasminogen), respectively. Methods of making amino acid deletions in a protein are well known to those of ordinary skill in the art (for e.g., *Current Protocols in Molecular Biology*, Ausubel et al. (eds.), John Wiley & Sons, 2001; and *Molecular Cloning: A Laboratory Manual*, Third Edition, Sambrook and Russell, 2000). The catalytic activity of a TPCD can be determined by measuring the amidolytic activity of the TPCD, using the chromogenic substrate S2403 (Chromogenix, Antwerp, Belgium) (see Example 2), any other chromogenic substrate, or by any other methods known in the art.

The present invention also envisions the use of a modified TPCD. A modified TPCD is a TPCD with a modified form of the catalytic domain of plasmin, wherein the modified TPCD possesses plasmin-like serine protease catalytic activity. Modifications to the catalytic domain include amino acid insertions and/or deletions and/or substitutions in the catalytic domain of plasmin. However, the amino acids corresponding to the catalytic triad of the plasmin serine protease domain namely, $Histidine_{603}$, $Aspartic Acid_{646}$ and $Serine_{741}$ are not altered. Preferably the modifications of the catalytic domain involve one or more conservative substitution(s) of amino acids that are not part of the catalytic triad. Conservative amino acid substitutions and methods of making such conservative amino acid substitutions are well known to one of ordinary skill in the art (see, e.g., *Current Protocols in Molecular Biology*, supra; and *Molecular Cloning: A Laboratory Manual*, supra). These modifications may increase, decrease or leave unchanged the catalytic activity of the original domain. The catalytic activity of a modified TPCD can be determined by measuring the amidolytic activity of the TPCD, using the chromogenic substrate S2403 (Chromogenix, Antwerp, Belgium) (see Example 2) or by any other methods known in the art.

TPCD includes, but is not limited to, miniplasmin, recombinant miniplasmin, stabilized miniplasmin, stabilized, recombinant miniplasmin, variants of miniplasmin, microplasmin, recombinant microplasmin, stabilized microplasmin, stabilized, recombinant microplasmin, and variants of microplasmin. Variants of microplasmin and miniplasmin include shorter forms of microplasmin and miniplasmin that can be produced by amino acid deletions from these proteins. All variants of microplasmin and miniplasmin are expected to have serine protease catalytic activity, even if they do not possess the same level of catalytic activity as microplasmin and miniplasmin, respectively. Thus, all variants of microplasmin and miniplasmin are required to contain amino acids 603-741 of SEQ ID NO:10, which contains the catalytic triad of the plasmin serine protease domain namely, $His_{603}$, $Asp_{646}$ and $Ser_{741}$ of human plasminogen. In one embodiment a variant of miniplasmin includes proteins containing one or more amino acid deletions in amino acids 444-791 of human plasminogen, wherein the resulting protein possesses serine protease catalytic activity. In another embodiment, a variant of microplasmin includes proteins containing one or more deletions in amino acids 543-791 of human plasminogen, wherein the resulting protein possesses serine protease catalytic activity. In yet another embodiment, a variant of microplasmin includes proteins containing one or more deletions in amino acids 562-791 of human plasminogen, wherein the resulting protein possesses serine protease catalytic activity. The deletions can be at the N-terminus, C-terminus or at an internal location of amino acids 444-791, 543-791 and 562-791 of SEQ ID NO:10, respectively; however, all variants of microplasmin and miniplasmin are required to contain amino acids 603-741 of SEQ ID NO:10. Variants of microplasmin and miniplasmin also include, but are not limited to, amino acid insertions and/or substitutions in these proteins. It is envisioned that amino acid substitutions made in microplasmin or miniplasmin are preferably conservative substitutions. Any variant of microplasmin and miniplasmin or any other TPCD can be prepared by recombinant methods and activated to the active plasmin form with a plasminogen activator. Alternatively, variants of microplasmin and miniplasmin or any other TPCD can be prepared by any other means well known in the art such as, but not limited to, digestion of human plasminogen with elastase or partial reduction and alkylation of plasmin, microplasmin or miniplasmin. These variants of microplasmin, miniplasmin, or for that matter any TPCD, can be assayed for serine protease catalytic activity using the chromogenic substrate S2403 or any other chromogenic substrate. In addition, the variants of microplasmin, miniplasmin or any other TPCD can be tested for their ability to induce PVD and/or effect vitreous liquefaction by injecting different doses of the variant in any balanced saline solution into porcine, feline or post-mortem human eyes. If a TPCD can induce PVD and/or effect vitreous liquefaction in any of these eyes, that TPCD is considered to be useful for treating eye disorders of mammals. Preferably, the TPCD does not result in toxicity to the injected eye. Non-limiting examples of variants of microplasmin are provided in Table 1.

TABLE 1

Non-limiting Examples of Variants of Microplasmin
The variants of microplasmin listed below correspond to the amino acid sequence and numbering of human plasminogen, which consists of amino acids 1-791
(see, FIG. 1, SEQ ID NO: 10).

542-741, 542-742, 542-743, 542-744, 542-745, 542-746, 542-747, 542-748, 542-749, 542-750, 542-751, 542-752, 542-753, 542-754, 542-755, 542-756, 542-757, 542-758, 542-759, 542-760, 542-761, 542-762, 542-763, 542-764, 542-765, 542-766, 542-767, 542-768, 542-769, 542-770, 542-771, 542-772, 542-773, 542-774, 542-775, 542-776, 542-777, 542-778, 542-779, 542-780, 542-781, 542-782, 542-783, 542-784, 542-785, 542-786, 542-787, 542-788, 542-789, 542-790, 542-791;
543-741, 543-742, 543-743, 543-744, 543-745, 543-746, 543-747, 543-748, 543-749, 543-750, 543-751, 543-752, 543-753, 543-754, 543-755, 543-756, 543-757, 543-758, 543-759, 543-760, 543-761, 543-762, 543-763, 543-764, 543-765, 543-766, 543-767, 543-768, 543-769, 543-770, 543-771, 543-772, 543-773, 543-774, 543-775, 543-776, 543-777, 543-778, 543-779, 543-780, 543-781, 543-782, 543-783, 543-784, 543-785, 543-786, 543-787, 543-788, 543-789, 543-790, 543-791;
544-741, 544-742, 544-743, 544-744, 544-745, 544-746, 544-747, 544-748, 544-749, 544-750, 544-751, 544-752, 544-753, 544-754, 544-755, 544-756, 544-757, 544-758, 544-759, 544-760, 544-761, 544-762, 544-763, 544-764, 544-765, 544-766, 544-767, 544-768, 544-769, 544-770, 544-771, 544-772, 544-773, 544-774, 544-775, 544-776, 544-777, 544-778, 544-779, 544-780, 544-781, 544-782, 544-783, 544-784, 544-785, 544-786, 544-787, 544-788, 544-789, 544-790, 544-791;
545-741, 545-742, 545-743, 545-744, 545-745, 545-746, 545-747, 545-748, 545-749, 545-750, 545-751, 545-752, 545-753, 545-754, 545-755, 545-756, 545-757, 545-758, 545-759, 545-760, 545-761, 545-762, 545-763, 545-764, 545-765, 545-766, 545-767, 545-768, 545-769, 545-770, 545-771, 545-772, 545-773, 545-774, 545-775, 545-776, 545-777, 545-778, 545-779, 545-780, 545-781, 545-782, 545-783, 545-784, 545-785, 545-786, 545-787, 545-788, 545-789, 545-790, 545-791;
546-741, 546-742, 546-743, 546-744, 546-745, 546-746, 546-747, 546-748, 546-749, 546-750, 546-751, 546-752, 546-753, 546-754, 546-755, 546-756, 546-757, 546-758, 546-759, 546-760, 546-761, 546-762, 546-763, 546-764, 546-765, 546-766, 546-767, 546-768, 546-769, 546-770, 546-771, 546-772, 546-773, 546-774, 546-775, 546-776, 546-777, 546-778, 546-779, 546-780, 546-781, 546-782, 546-783, 546-784, 546-785, 546-786, 546-787, 546-788, 546-789, 546-790, 546-791;
547-741, 547-742, 547-743, 547-744, 547-745, 547-746, 547-747, 547-748, 547-749, 547-750, 547-751, 547-752, 547-753, 547-754, 547-755, 547-756, 547-757, 547-758, 547-759, 547-760, 547-761, 547-762, 547-763, 547-764, 547-765, 547-766, 547-767, 547-768, 547-769, 547-770, 547-771, 547-772, 547-773, 547-774, 547-775, 547-776, 547-777, 547-778, 547-779, 547-780, 547-781, 547-782, 547-783, 547-784, 547-785, 547-786, 547-787, 547-788, 547-789, 547-790, 547-791;
548-741, 548-742, 548-743, 548-744, 548-745, 548-746, 548-747, 548-748, 548-749, 548-750, 548-751, 548-752, 548-753, 548-754, 548-755, 548-756, 548-757, 548-758, 548-759, 548-760, 548-761, 548-762, 548-763, 548-764, 548-765, 548-766, 548-767, 548-768, 548-769, 548-770, 548-771, 548-772, 548-773, 548-774, 548-775, 548-776, 548-777, 548-778, 548-779, 548-780, 548-781, 548-782, 548-783, 548-784, 548-785, 548-786, 548-787, 548-788, 548-789, 548-790, 548-791;
549-741, 549-742, 549-743, 549-744, 549-745, 549-746, 549-747, 549-748, 549-749, 549-750, 549-751, 549-752, 549-753, 549-754, 549-755, 549-756, 549-757, 549-758, 549-759, 549-760, 549-761, 549-762, 549-763, 549-764, 549-765, 549-766, 549-767, 549-768, 549-769, 549-770, 549-771, 549-772, 549-773, 549-774, 549-775, 549-776, 549-777, 549-778, 549-779, 549-780, 549-781, 549-782, 549-783, 549-784, 549-785, 549-786, 549-787, 549-788, 549-789, 549-790, 549-791;
550-741, 550-742, 550-743, 550-744, 550-745, 550-746, 550-747, 550-748, 550-749,

TABLE 1-continued

Non-limiting Examples of Variants of Microplasmin
The variants of microplasmin listed below correspond to the amino acid sequence
and numbering of human plasminogen, which consists of amino acids 1-791
(see, FIG. 1, SEQ ID NO: 10).

550-750, 550-751, 550-752, 550-753, 550-754, 550-755, 550-756, 550-757, 550-758,
550-759, 550-760, 550-761, 550-762, 550-763, 550-764, 550-765, 550-766, 550-767,
550-768, 550-769, 550-770, 550-771, 550-772, 550-773, 550-774, 550-775, 550-776,
550-777, 550-778, 550-779, 550-780, 550-781, 550-782, 550-783, 550-784, 550-785,
550-786, 550-787, 550-788, 550-789, 550-790, 550-791;
551-741, 551-742, 551-743, 551-744, 551-745, 551-746, 551-747, 551-748, 551-749,
551-750, 551-751, 551-752, 551-753, 551-754, 551-755, 551-756, 551-757, 551-758,
551-759, 551-760, 551-761, 551-762, 551-763, 551-764, 551-765, 551-766, 551-767,
551-768, 551-769, 551-770, 551-771, 551-772, 551-773, 551-774, 551-775, 551-776,
551-777, 551-778, 551-779, 551-780, 551-781, 551-782, 551-783, 551-784, 551-785,
551-786, 551-787, 551-788, 551-789, 551-790, 551-791;
552-741, 552-742, 552-743, 552-744, 552-745, 552-746, 552-747, 552-748, 552-749,
552-750, 552-751, 552-752, 552-753, 552-754, 552-755, 552-756, 552-757, 552-758,
552-759, 552-760, 552-761, 552-762, 552-763, 552-764, 552-765, 552-766, 552-767,
552-768, 552-769, 552-770, 552-771, 552-772, 552-773, 552-774, 552-775, 552-776,
552-777, 552-778, 552-779, 552-780, 552-781, 552-782, 552-783, 552-784, 552-785,
552-786, 552-787, 552-788, 552-789, 552-790, 552-791;
553-741, 553-742, 553-743, 553-744, 553-745, 553-746, 553-747, 553-748, 553-749,
553-750, 553-751, 553-752, 553-753, 553-754, 553-755, 553-756, 553-757, 553-758,
553-759, 553-760, 553-761, 553-762, 553-763, 553-764, 553-765, 553-766, 553-767,
553-768, 553-769, 553-770, 553-771, 553-772, 553-773, 553-774, 553-775, 553-776,
553-777, 553-778, 553-779, 553-780, 553-781, 553-782, 553-783, 553-784, 553-785,
553-786, 553-787, 553-788, 553-789, 553-790, 553-791;
554-741, 554-742, 554-743, 554-744, 554-745, 554-746, 554-747, 554-748, 554-749,
554-750, 554-751, 554-752, 554-753, 554-754, 554-755, 554-756, 554-757, 554-758,
554-759, 554-760, 554-761, 554-762, 554-763, 554-764, 554-765, 554-766, 554-767,
554-768, 554-769, 554-770, 554-771, 554-772, 554-773, 554-774, 554-775, 554-776,
554-777, 554-778, 554-779, 554-780, 5544-781, 554-782, 554-783, 554-784, 554-785,
554-786, 554-787, 554-788, 554-789, 554-790, 554-791;
555-741, 555-742, 555-743, 555-744, 555-745, 555-746, 555-747, 555-748, 555-749,
555-750, 555-751, 555-752, 555-753, 555-754, 555-755, 555-756, 555-757, 555-758,
555-759, 555-760, 555-761, 555-762, 555-763, 555-764, 555-765, 555-766, 555-767,
555-768, 555-769, 555-770, 555-771, 555-772, 555-773, 555-774, 555-775, 555-776,
555-777, 555-778, 555-779, 555-780, 555-781, 555-782, 555-783, 555-784, 555-785,
555-786, 555-787, 555-788, 555-789, 555-790, 555-791;
556-741, 556-742, 556-743, 556-744, 556-745, 556-746, 556-747, 556-748, 556-749,
556-750, 556-751, 556-752, 556-753, 556-754, 556-755, 556-756, 556-757, 556-758,
556-759, 556-760, 556-761, 556-762, 556-763, 556-764, 556-765, 556-766, 556-767,
556-768, 556-769, 556-770, 556-771, 556-772, 556-773, 556-774, 556-775, 556-776,
556-777, 556-778, 556-779, 556-780, 556-781, 556-782, 556-783, 556-784, 556-785,
556-786, 556-787, 556-788, 556-789, 556-790, 556-791;
557-741, 557-742, 557-743, 557-744, 557-745, 557-746, 557-747, 557-748, 557-749,
557-750, 557-751, 557-752, 557-753, 557-754, 557-755, 557-756, 557-757, 557-758,
557-759, 557-760, 557-761, 557-762, 557-763, 557-764, 557-765, 557-766, 557-767,
557-768, 557-769, 557-770, 557-771, 557-772, 557-773, 557-774, 557-775, 557-776,
557-777, 557-778, 557-779, 557-780, 557-781, 557-782, 557-783, 557-784, 557-785,
557-786, 557-787, 557-788, 557-789, 557-790, 557-791;
558-741, 558-742, 558-743, 558-744, 558-745, 558-746, 558-747, 558-748, 558-749,
558-750, 558-751, 558-752, 558-753, 558-754, 558-755, 558-756, 558-757, 558-758,
558-759, 558-760, 558-761, 558-762, 558-763, 558-764, 558-765, 558-766, 558-767,
558-768, 558-769, 558-770, 558-771, 558-772, 558-773, 558-774, 558-775, 558-776,
558-777, 558-778, 558-779, 558-780, 558-781, 558-782, 558-783, 558-784, 558-785,
558-786, 558-787, 558-788, 558-789, 558-790, 558-791;
559-741, 559-742, 559-743, 559-744, 559-745, 559-746, 559-747, 559-748, 559-749,
559-750, 559-751, 559-752, 559-753, 559-754, 559-755, 559-756, 559-757, 559-758,
559-759, 559-760, 559-761, 559-762, 559-763, 559-764, 559-765, 559-766, 559-767,
559-768, 559-769, 559-770, 559-771, 559-772, 559-773, 559-774, 559-775, 559-776,
559-777, 559-778, 559-779, 559-780, 559-781, 559-782, 559-783, 559-784, 559-785,
559-786, 559-787, 559-788, 559-789, 559-790, 559-791;
560-741, 560-742, 560-743, 560-744, 560-745, 560-746, 560-747, 560-748, 560-749,
560-750, 560-751, 560-752, 560-753, 560-754, 560-755, 560-756, 560-757, 560-758,
560-759, 560-760, 560-761, 560-762, 560-763, 560-764, 560-765, 560-766, 560-767,
560-768, 560-769, 560-770, 560-771, 560-772, 560-773, 560-774, 560-775, 560-776,
560-777, 560-778, 560-779, 560-780, 560-781, 560-782, 560-783, 560-784, 560-785,
560-786, 560-787, 560-788, 560-789, 560-790, 560-791;
561-741, 561-742, 561-743, 561-744, 561-745, 561-746, 561-747, 561-748, 561-749,
561-750, 561-751, 561-752, 561-753, 561-754, 561-755, 561-756, 561-757, 561-758,
561-759, 561-760, 561-761, 561-762, 561-763, 561-764, 561-765, 561-766, 561-767,
561-768, 561-769, 561-770, 561-771, 561-772, 561-773, 561-774, 561-775, 561-776,
561-777, 561-778, 561-779, 561-780, 561-781, 561-782, 561-783, 561-784, 561-785,
561-786, 561-787, 561-788, 561-789, 561-790, 561-791;
562-741, 562-742, 562-743, 562-744, 562-745, 562-746, 562-747, 562-748, 562-749,
562-750, 562-751, 562-752, 562-753, 562-754, 562-755, 562-756, 562-757, 562-758,
562-759, 562-760, 562-761, 562-762, 562-763, 562-764, 562-765, 562-766, 562-767,
562-768, 562-769, 562-770, 562-771, 562-772, 562-773, 562-774, 562-775, 562-776,

TABLE 1-continued

Non-limiting Examples of Variants of Microplasmin
The variants of microplasmin listed below correspond to the amino acid sequence
and numbering of human plasminogen, which consists of amino acids 1-791
(see, FIG. 1, SEQ ID NO: 10).

562-777, 562-778, 562-779, 562-780, 562-781, 562-782, 562-783, 562-784, 562-785, 562-786, 562-787, 562-788, 562-789, 562-790, 562-791;
563-741, 563-742, 563-743, 563-744, 563-745, 563-746, 563-747, 563-748, 563-749, 563-750, 563-751, 563-752, 563-753, 563-754, 563-755, 563-756, 563-757, 563-758, 563-759, 563-760, 563-761, 563-762, 563-763, 563-764, 563-765, 563-766, 563-767, 563-768, 563-769, 563-770, 563-771, 563-772, 563-773, 563-774, 563-775, 563-776, 563-777, 563-778, 563-779, 563-780, 563-781, 563-782, 563-783, 563-784, 563-785, 563-786, 563-787, 563-788, 563-789, 563-790, 563-791;
564-741, 564-742, 564-743, 564-744, 564-745, 564-746, 564-747, 564-748, 564-749, 564-750, 564-751, 564-752, 564-753, 564-754, 564-755, 564-756, 564-757, 564-758, 564-759, 564-760, 564-761, 564-762, 564-763, 564-764, 564-765, 564-766, 564-767, 564-768, 564-769, 564-770, 564-771, 564-772, 564-773, 564-774, 564-775, 564-776, 564-777, 564-778, 564-779, 564-780, 564-781, 564-782, 564-783, 564-784, 564-785, 564-786, 564-787, 564-788, 564-789, 564-790, 564-791;
565-741, 565-742, 565-743, 565-744, 565-745, 565-746, 565-747, 565-748, 565-749, 565-750, 565-751, 565-752, 565-753, 565-754, 565-755, 565-756, 565-757, 565-758, 565-759, 565-760, 565-761, 565-762, 565-763, 565-764, 565-765, 565-766, 565-767, 565-768, 565-769, 565-770, 565-771, 565-772, 565-773, 565-774, 565-775, 565-776, 565-777, 565-778, 565-779, 565-780, 565-781, 565-782, 565-783, 565-784, 565-785, 565-786, 565-787, 565-788, 565-789, 565-790, 565-791;
566-741, 566-742, 566-743, 566-744, 566-745, 566-746, 566-747, 566-748, 566-749, 566-750, 566-751, 566-752, 566-753, 566-754, 566-755, 566-756, 566-757, 566-758, 566-759, 566-760, 566-761, 566-762, 566-763, 566-764, 566-765, 566-766, 566-767, 566-768, 566-769, 566-770, 566-771, 566-772, 566-773, 566-774, 566-775, 566-776, 566-777, 566-778, 566-779, 566-780, 566-781, 566-782, 566-783, 566-784, 566-785, 566-786, 566-787, 566-788, 566-789, 566-790, 566-791;
567-741, 567-742, 567-743, 567-744, 567-745, 567-746, 567-747, 567-748, 567-749, 567-750, 567-751, 567-752, 567-753, 567-754, 567-755, 567-756, 567-757, 567-758, 567-759, 567-760, 567-761, 567-762, 567-763, 567-764, 567-765, 567-766, 567-767, 567-768, 567-769, 567-770, 567-771, 567-772, 567-773, 567-774, 567-775, 567-776, 567-777, 567-778, 567-779, 567-780, 567-781, 567-782, 567-783, 567-784, 567-785, 567-786, 567-787, 567-788, 567-789, 567-790, 567-791;
568-741, 568-742, 568-743, 568-744, 568-745, 568-746, 568-747, 568-748, 568-749, 568-750, 568-751, 568-752, 568-753, 568-754, 568-755, 568-756, 568-757, 568-758, 568-759, 568-760, 568-761, 568-762, 568-763, 568-764, 568-765, 568-766, 568-767, 568-768, 568-769, 568-770, 568-771, 568-772, 568-773, 568-774, 568-775, 568-776, 568-777, 568-778, 568-779, 568-780, 568-781, 568-782, 568-783, 568-784, 568-785, 568-786, 568-787, 568-788, 568-789, 568-790, 568-791;
569-741, 569-742, 569-743, 569-744, 569-745, 569-746, 569-747, 569-748, 569-749, 569-750, 569-751, 569-752, 569-753, 569-754, 569-755, 569-756, 569-757, 569-758, 569-759, 569-760, 569-761, 569-762, 569-763, 569-764, 569-765, 569-766, 569-767, 569-768, 569-769, 569-770, 569-771, 569-772, 569-773, 569-774, 569-775, 569-776, 569-777, 569-778, 569-779, 569-780, 569-781, 569-782, 569-783, 569-784, 569-785, 569-786, 569-787, 569-788, 569-789, 569-790, 569-791;
570-741, 570-742, 570-743, 570-744, 570-745, 570-746, 570-747, 570-748, 570-749, 570-750, 570-751, 570-752, 570-753, 570-754, 570-755, 570-756, 570-757, 570-758, 570-759, 570-760, 570-761, 570-762, 570-763, 570-764, 570-765, 570-766, 570-767, 570-768, 570-769, 570-770, 570-771, 570-772, 570-773, 570-774, 570-775, 570-776, 570-777, 570-778, 570-779, 570-780, 570-781, 570-782, 570-783, 570-784, 570-785, 570-786, 570-787, 570-788, 570-789, 570-790, 570-791;
571-741, 571-742, 571-743, 571-744, 571-745, 571-746, 571-747, 571-748, 571-749, 571-750, 571-751, 571-752, 571-753, 571-754, 571-755, 571-756, 571-757, 571-758, 571-759, 571-760, 571-761, 571-762, 571-763, 571-764, 571-765, 571-766, 571-767, 571-768, 571-769, 571-770, 571-771, 571-772, 571-773, 571-774, 571-775, 571-776, 571-777, 571-778, 571-779, 571-780, 571-781, 571-782, 571-783, 571-784, 571-785, 571-786, 571-787, 571-788, 571-789, 571-790, 571-791;
572-741, 572-742, 572-743, 572-744, 572-745, 572-746, 572-747, 572-748, 572-749, 572-750, 572-751, 572-752, 572-753, 572-754, 572-755, 572-756, 572-757, 572-758, 572-759, 572-760, 572-761, 572-762, 572-763, 572-764, 572-765, 572-766, 572-767, 572-768, 572-769, 572-770, 572-771, 572-772, 572-773, 572-774, 572-775, 572-776, 572-777, 572-778, 572-779, 572-780, 572-781, 572-782, 572-783, 572-784, 572-785, 572-786, 572-787, 572-788, 572-789, 572-790, 572-791;
573-741, 573-742, 573-743, 573-744, 573-745, 573-746, 573-747, 573-748, 573-749, 573-750, 573-751, 573-752, 573-753, 573-754, 573-755, 573-756, 573-757, 573-758, 573-759, 573-760, 573-761, 573-762, 573-763, 573-764, 573-765, 573-766, 573-767, 573-768, 573-769, 573-770, 573-771, 573-772, 573-773, 573-774, 573-775, 573-776, 573-777, 573-778, 573-779, 573-780, 573-781, 573-782, 573-783, 573-784, 573-785, 573-786, 573-787, 573-788, 573-789, 573-790, 573-791;
574-741, 574-742, 574-743, 574-744, 574-745, 574-746, 574-747, 574-748, 574-749, 574-750, 574-751, 574-752, 574-753, 574-754, 574-755, 574-756, 574-757, 574-758, 574-759, 574-760, 574-761, 574-762, 574-763, 574-764, 574-765, 574-766, 574-767, 574-768, 574-769, 574-770, 574-771, 574-772, 574-773, 574-774, 574-775, 574-776, 574-777, 574-778, 574-779, 574-780, 574-781, 574-782, 574-783, 574-784, 574-785, 574-786, 574-787, 574-788, 574-789, 574-790, 574-791;
575-741, 575-742, 575-743, 575-744, 575-745, 575-746, 575-747, 575-748, 575-749,

TABLE 1-continued

Non-limiting Examples of Variants of Microplasmin
The variants of microplasmin listed below correspond to the amino acid sequence
and numbering of human plasminogen, which consists of amino acids 1-791
(see, FIG. 1, SEQ ID NO: 10).

575-750, 575-751, 575-752, 575-753, 575-754, 575-755, 575-756, 575-757, 575-758,
575-759, 575-760, 575-761, 575-762, 575-763, 575-764, 575-765, 575-766, 575-767,
575-768, 575-769, 575-770, 575-771, 575-772, 575-773, 575-774, 575-775, 575-776,
575-777, 575-778, 575-779, 575-780, 575-781, 575-782, 575-783, 575-784, 575-785,
575-786, 575-787, 575-788, 575-789, 575-790, 575-791;
576-741, 576-742, 576-743, 576-744, 576-745, 576-746, 576-747, 576-748, 576-749,
576-750, 576-751, 576-752, 576-753, 576-754, 576-755, 576-756, 576-757, 576-758,
576-759, 576-760, 576-761, 576-762, 576-763, 576-764, 576-765, 576-766, 576-767,
576-768, 576-769, 576-770, 576-771, 576-772, 576-773, 576-774, 576-775, 576-776,
576-777, 576-778, 576-779, 576-780, 576-781, 576-782, 576-783, 576-784, 576-785,
576-786, 576-787, 576-788, 576-789, 576-790, 576-791;
577-741, 577-742, 577-743, 577-744, 577-745, 577-746, 577-747, 577-748, 577-749,
577-750, 577-751, 577-752, 577-753, 577-754, 577-755, 577-756, 577-757, 577-758,
577-759, 577-760, 577-761, 577-762, 577-763, 577-764, 577-765, 577-766, 577-767,
577-768, 577-769, 577-770, 577-771, 577-772, 577-773, 577-774, 577-775, 577-776,
577-777, 577-778, 577-779, 577-780, 577-781, 577-782, 577-783, 577-784, 577-785,
577-786, 577-787, 577-788, 577-789, 577-790, 577-791;
578-741, 578-742, 578-743, 578-744, 578-745, 578-746, 578-747, 578-748, 578-749,
578-750, 578-751, 578-752, 578-753, 578-754, 578-755, 578-756, 578-757, 578-758,
578-759, 578-760, 578-761, 578-762, 578-763, 578-764, 578-765, 578-766, 578-767,
578-768, 578-769, 578-770, 578-771, 578-772, 578-773, 578-774, 578-775, 578-776,
578-777, 578-778, 578-779, 578-780, 578-781, 578-782, 578-783, 578-784, 578-785,
578-786, 578-787, 578-788, 578-789, 578-790, 578-791;
579-741, 579-742, 579-743, 579-744, 579-745, 579-746, 579-747, 579-748, 579-749,
579-750, 579-751, 579-752, 579-753, 579-754, 579-755, 579-756, 579-757, 579-758,
579-759, 579-760, 579-761, 579-762, 579-763, 579-764, 579-765, 579-766, 579-767,
579-768, 579-769, 579-770, 579-771, 579-772, 579-773, 579-774, 579-775, 579-776,
579-777, 579-778, 579-779, 579-780, 579-781, 579-782, 579-783, 579-784, 579-785,
579-786, 579-787, 579-788, 579-789, 579-790, 579-791;
580-741, 580-742, 580-743, 580-744, 580-745, 580-746, 580-747, 580-748, 580-749,
580-750, 580-751, 580-752, 580-753, 580-754, 580-755, 580-756, 580-757, 580-758,
580-759, 580-760, 580-761, 580-762, 580-763, 580-764, 580-765, 580-766, 580-767,
580-768, 580-769, 580-770, 580-771, 580-772, 580-773, 580-774, 580-775, 580-776,
580-777, 580-778, 580-779, 580-780, 580-781, 580-782, 580-783, 580-784, 580-785,
580-786, 580-787, 580-788, 580-789, 580-790, 580-791;
581-741, 581-742, 581-743, 581-744, 581-745, 581-746, 581-747, 581-748, 581-749,
581-750, 581-751, 581-752, 581-753, 581-754, 581-755, 581-756, 581-757, 581-758,
581-759, 581-760, 581-761, 581-762, 581-763, 581-764, 581-765, 581-766, 581-767,
581-768, 581-769, 581-770, 581-771, 581-772, 581-773, 581-774, 581-775, 581-776,
581-777, 581-778, 581-779, 581-780, 581-781, 581-782, 581-783, 581-784, 581-785,
581-786, 581-787, 581-788, 581-789, 581-790, 581-791;
582-741, 582-742, 582-743, 582-744, 582-745, 582-746, 582-747, 582-748, 582-749,
582-750, 582-751, 582-752, 582-753, 582-754, 582-755, 582-756, 582-757, 582-758,
582-759, 582-760, 582-761, 582-762, 582-763, 582-764, 582-765, 582-766, 582-767,
582-768, 582-769, 582-770, 582-771, 582-772, 582-773, 582-774, 582-775, 582-776,
582-777, 582-778, 582-779, 582-780, 582-781, 582-782, 582-783, 582-784, 582-785,
582-786, 582-787, 582-788, 582-789, 582-790, 582-791;
583-741, 583-742, 583-743, 583-744, 583-745, 583-746, 583-747, 583-748, 583-749,
583-750, 583-751, 583-752, 583-753, 583-754, 583-755, 583-756, 583-757, 583-758,
583-759, 583-760, 583-761, 583-762, 583-763, 583-764, 583-765, 583-766, 583-767,
583-768, 583-769, 583-770, 583-771, 583-772, 583-773, 583-774, 583-775, 583-776,
583-777, 583-778, 583-779, 583-780, 583-781, 583-782, 583-783, 583-784, 583-785,
583-786, 583-787, 583-788, 583-789, 583-790, 583-791;
584-741, 584-742, 584-743, 584-744, 584-745, 584-746, 584-747, 584-748, 584-749,
584-750, 584-751, 584-752, 584-753, 584-754, 584-755, 584-756, 584-757, 584-758,
584-759, 584-760, 584-761, 584-762, 584-763, 584-764, 584-765, 584-766, 584-767,
584-768, 584-769, 584-770, 584-771, 584-772, 584-773, 584-774, 584-775, 584-776,
584-777, 584-778, 584-779, 584-780, 584-781, 584-782, 584-783, 584-784, 584-785,
584-786, 584-787, 584-788, 584-789, 584-790, 584-791;
585-741, 585-742, 585-743, 585-744, 585-745, 585-746, 585-747, 585-748, 585-749,
585-750, 585-751, 585-752, 585-753, 585-754, 585-755, 585-756, 585-757, 585-758,
585-759, 585-760, 585-761, 585-762, 585-763, 585-764, 585-765, 585-766, 585-767,
585-768, 585-769, 585-770, 585-771, 585-772, 585-773, 585-774, 585-775, 585-776,
585-777, 585-778, 585-779, 585-780, 585-781, 585-782, 585-783, 585-784, 585-785,
585-786, 585-787, 585-788, 585-789, 585-790, 585-791;
586-741, 586-742, 586-743, 586-744, 586-745, 586-746, 586-747, 586-748, 586-749,
586-750, 586-751, 586-752, 586-753, 586-754, 586-755, 586-756, 586-757, 586-758,
586-759, 586-760, 586-761, 586-762, 586-763, 586-764, 586-765, 586-766, 586-767,
586-768, 586-769, 586-770, 586-771, 586-772, 586-773, 586-774, 586-775, 586-776,
586-777, 586-778, 586-779, 586-780, 586-781, 586-782, 586-783, 586-784, 586-785,
586-786, 586-787, 586-788, 586-789, 586-790, 586-791;
587-741, 587-742, 587-743, 587-744, 587-745, 587-746, 587-747, 587-748, 587-749,
587-750, 587-751, 587-752, 587-753, 587-754, 587-755, 587-756, 587-757, 587-758,
587-759, 587-760, 587-761, 587-762, 587-763, 587-764, 587-765, 587-766, 587-767,
587-768, 587-769, 587-770, 587-771, 587-772, 587-773, 587-774, 587-775, 587-776,

TABLE 1-continued

Non-limiting Examples of Variants of Microplasmin
The variants of microplasmin listed below correspond to the amino acid sequence
and numbering of human plasminogen, which consists of amino acids 1-791
(see, FIG. 1, SEQ ID NO: 10).

587-777, 587-778, 587-779, 587-780, 587-781, 587-782, 587-783, 587-784, 587-785, 587-786, 587-787, 587-788, 587-789, 587-790, 587-791;
588-741, 588-742, 588-743, 588-744, 588-745, 588-746, 588-747, 588-748, 588-749, 588-750, 588-751, 588-752, 588-753, 588-754, 588-755, 588-756, 588-757, 588-758, 588-759, 588-760, 588-761, 588-762, 588-763, 588-764, 588-765, 588-766, 588-767, 588-768, 588-769, 588-770, 588-771, 588-772, 588-773, 588-774, 588-775, 588-776, 588-777, 588-778, 588-779, 588-780, 588-781, 588-782, 588-783, 588-784, 588-785, 588-786, 588-787, 588-788, 588-789, 588-790, 588-791;
589-741, 589-742, 589-743, 589-744, 589-745, 589-746, 589-747, 589-748, 589-749, 589-750, 589-751, 589-752, 589-753, 589-754, 589-755, 589-756, 589-757, 589-758, 589-759, 589-760, 589-761, 589-762, 589-763, 589-764, 589-765, 589-766, 589-767, 589-768, 589-769, 589-770, 589-771, 589-772, 589-773, 589-774, 589-775, 589-776, 589-777, 589-778, 589-779, 589-780, 589-781, 589-782, 589-783, 589-784, 589-785, 589-786, 589-787, 589-788, 589-789, 589-790, 589-791;
590-741, 590-742, 590-743, 590-744, 590-745, 590-746, 590-747, 590-748, 590-749, 590-750, 590-751, 590-752, 590-753, 590-754, 590-755, 590-756, 590-757, 590-758, 590-759, 590-760, 590-761, 590-762, 590-763, 590-764, 590-765, 590-766, 590-767, 590-768, 590-769, 590-770, 590-771, 590-772, 590-773, 590-774, 590-775, 590-776, 590-777, 590-778, 590-779, 590-780, 590-781, 590-782, 590-783, 590-784, 590-785, 590-786, 590-787, 590-788, 590-789, 590-790, 590-791;
591-741, 591-742, 591-743, 591-744, 591-745, 591-746, 591-747, 591-748, 591-749, 591-750, 591-751, 591-752, 591-753, 591-754, 591-755, 591-756, 591-757, 591-758, 591-759, 591-760, 591-761, 591-762, 591-763, 591-764, 591-765, 591-766, 591-767, 591-768, 591-769, 591-770, 591-771, 591-772, 591-773, 591-774, 591-775, 591-776, 591-777, 591-778, 591-779, 591-780, 591-781, 591-782, 591-783, 591-784, 591-785, 591-786, 591-787, 591-788, 591-789, 591-790, 591-791;
592-741, 592-742, 592-743, 592-744, 592-745, 592-746, 592-747, 592-748, 592-749, 592-750, 592-751, 592-752, 592-753, 592-754, 592-755, 592-756, 592-757, 592-758, 592-759, 592-760, 592-761, 592-762, 592-763, 592-764, 592-765, 592-766, 592-767, 592-768, 592-769, 592-770, 592-771, 592-772, 592-773, 592-774, 592-775, 592-776, 592-777, 592-778, 592-779, 592-780, 592-781, 592-782, 592-783, 592-784, 592-785, 592-786, 592-787, 592-788, 592-789, 592-790, 592-791;
593-741, 593-742, 593-743, 593-744, 593-745, 593-746, 593-747, 593-748, 593-749, 593-750, 593-751, 593-752, 593-753, 593-754, 593-755, 593-756, 593-757, 593-758, 593-759, 593-760, 593-761, 593-762, 593-763, 593-764, 593-765, 593-766, 593-767, 593-768, 593-769, 593-770, 593-771, 593-772, 593-773, 593-774, 593-775, 593-776, 593-777, 593-778, 593-779, 593-780, 593-781, 593-782, 593-783, 593-784, 593-785, 593-786, 593-787, 593-788, 593-789, 593-790, 593-791;
594-741, 594-742, 594-743, 594-744, 594-745, 594-746, 594-747, 594-748, 594-749, 594-750, 594-751, 594-752, 594-753, 594-754, 594-755, 594-756, 594-757, 594-758, 594-759, 594-760, 594-761, 594-762, 594-763, 594-764, 594-765, 594-766, 594-767, 594-768, 594-769, 594-770, 594-771, 594-772, 594-773, 594-774, 594-775, 594-776, 594-777, 594-778, 594-779, 594-780, 594-781, 594-782, 594-783, 594-784, 594-785, 594-786, 594-787, 594-788, 594-789, 594-790, 594-791;
595-741, 595-742, 595-743, 595-744, 595-745, 595-746, 595-747, 595-748, 595-749, 595-750, 595-751, 595-752, 595-753, 595-754, 595-755, 595-756, 595-757, 595-758, 595-759, 595-760, 595-761, 595-762, 595-763, 595-764, 595-765, 595-766, 595-767, 595-768, 595-769, 595-770, 595-771, 595-772, 595-773, 595-774, 595-775, 595-776, 595-777, 595-778, 595-779, 595-780, 595-781, 595-782, 595-783, 595-784, 595-785, 595-786, 595-787, 595-788, 595-789, 595-790, 595-791;
596-741, 596-742, 596-743, 596-744, 596-745, 596-746, 596-747, 596-748, 596-749, 596-750, 596-751, 596-752, 596-753, 596-754, 596-755, 596-756, 596-757, 596-758, 596-759, 596-760, 596-761, 596-762, 596-763, 596-764, 596-765, 596-766, 596-767, 596-768, 596-769, 596-770, 596-771, 596-772, 596-773, 596-774, 596-775, 596-776, 596-777, 596-778, 596-779, 596-780, 596-781, 596-782, 596-783, 596-784, 596-785, 596-786, 596-787, 596-788, 596-789, 596-790, 596-791;
597-741, 597-742, 597-743, 597-744, 597-745, 597-746, 597-747, 597-748, 597-749, 597-750, 597-751, 597-752, 597-753, 597-754, 597-755, 597-756, 597-757, 597-758, 597-759, 597-760, 597-761, 597-762, 597-763, 597-764, 597-765, 597-766, 597-767, 597-768, 597-769, 597-770, 597-771, 597-772, 597-773, 597-774, 597-775, 597-776, 597-777, 597-778, 597-779, 597-780, 597-781, 597-782, 597-783, 597-784, 597-785, 597-786, 597-787, 597-788, 597-789, 597-790, 597-791;
598-741, 598-742, 598-743, 598-744, 598-745, 598-746, 598-747, 598-748, 598-749, 598-750, 598-751, 598-752, 598-753, 598-754, 598-755, 598-756, 598-757, 598-758, 598-759, 598-760, 598-761, 598-762, 598-763, 598-764, 598-765, 598-766, 598-767, 598-768, 598-769, 598-770, 598-771, 598-772, 598-773, 598-774, 598-775, 598-776, 598-777, 598-778, 598-779, 598-780, 598-781, 598-782, 598-783, 598-784, 598-785, 598-786, 598-787, 598-788, 598-789, 598-790, 598-791;
599-741, 599-742, 599-743, 599-744, 599-745, 599-746, 599-747, 599-748, 599-749, 599-750, 599-751, 599-752, 599-753, 599-754, 599-755, 599-756, 599-757, 599-758, 599-759, 599-760, 599-761, 599-762, 599-763, 599-764, 599-765, 599-766, 599-767, 599-768, 599-769, 599-770, 599-771, 599-772, 599-773, 599-774, 599-775, 599-776, 599-777, 599-778, 599-779, 599-780, 599-781, 599-782, 599-783, 599-784, 599-785, 599-786, 599-787, 599-788, 599-789, 599-790, 599-791;
600-741, 600-742, 600-743, 600-744, 600-745, 600-746, 600-747, 600-748, 600-749,

TABLE 1-continued

Non-limiting Examples of Variants of Microplasmin
The variants of microplasmin listed below correspond to the amino acid sequence
and numbering of human plasminogen, which consists of amino acids 1-791
(see, FIG. 1, SEQ ID NO: 10).

600-750, 600-751, 600-752, 600-753, 600-754, 600-755, 600-756, 600-757, 600-758,
600-759, 600-760, 600-761, 600-762, 600-763, 600-764, 600-765, 600-766, 600-767,
600-768, 600-769, 600-770, 600-771, 600-772, 600-773, 600-774, 600-775, 600-776,
600-777, 600-778, 600-779, 600-780, 600-781, 600-782, 600-783, 600-784, 600-785,
600-786, 600-787, 600-788, 600-789, 600-790, 600-791;
601-741, 601-742, 601-743, 601-744, 601-745, 601-746, 601-747, 601-748, 601-749,
601-750, 601-751, 601-752, 601-753, 601-754, 601-755, 601-756, 601-757, 601-758,
601-759, 601-760, 601-761, 601-762, 601-763, 601-764, 601-765, 601-766, 601-767,
601-768, 601-769, 601-770, 601-771, 601-772, 601-773, 601-774, 601-775, 601-776,
601-777, 601-778, 601-779, 601-780, 601-781, 601-782, 601-783, 601-784, 601-785,
601-786, 601-787, 601-788, 601-789, 601-790, 601-791;
602-741, 602-742, 602-743, 602-744, 602-745, 602-746, 602-747, 602-748, 602-749,
602-750, 602-751, 602-752, 602-753, 602-754, 602-755, 602-756, 602-757, 602-758,
602-759, 602-760, 602-761, 602-762, 602-763, 602-764, 602-765, 602-766, 602-767,
602-768, 602-769, 602-770, 602-771, 602-772, 602-773, 602-774, 602-775, 602-776,
602-777, 602-778, 602-779, 602-780, 602-781, 602-782, 602-783, 602-784, 602-785,
602-786, 602-787, 602-788, 602-789, 602-790, 602-791

Miniplasmin and microplasmin are produced upon the activation of miniplasminogen and microplasminogen by plasminogen activators such as, but not limited to, streptokinase, staphylokinase, tissue-type plasminogen activator or urokinase. Miniplasminogen and microplasminogen are derived from plasminogen, which is a single chain glycoprotein that is an important component of mammalian blood. Human plasminogen is a multi-domain protein of 791 residues (SEQ ID NO:10), composed of an N-terminal pre-activation domain, five homologous kringle domains each of about 80 amino acids, a serine protease catalytic domain and inter-domain connecting sequences. Plasmin or plasminogen activators cleave the peptide bonds between $Arg_{68}$-$Met_{69}$, or $Lys_{77}$-$Lys_{78}$ or $Lys_{78}$-$Val_{79}$ at the N-terminal of human plasminogen, resulting in shorter proenzymes called Lys-plasminogens (for example, proteins consisting of amino acids 69-791 or 78-791 or 79-791). Additional cleavage by the enzyme elastase removes the first four kringle domains producing the proenzyme, miniplasminogen (typically amino acids 442-791). Further cleavage of the fifth kringle yields the proenzyme, microplasminogen (typically amino acids 543-791). The kringles of plasminogen contain lysine-binding sites that mediate specific binding of plasminogen to substrates such as fibrin. The proenzyme forms of plasminogen are activated to their enzymatically active form by the cleavage of the peptide bond between $Arg_{561}$ and $Val_{562}$ to yield a disulfide bonded double chain form of the corresponding protein. The product of activation of a plasminogen protein is called a plasmin. Thus, the product of Lys-plasminogen activation is called Lys-plasmin, while the products of activation of miniplasminogen and microplasminogen, are referred to as miniplasmin and microplasmin, respectively. Lys-plasmin has a molecular weight of about 65,000 in its unglycosylated form and a molecular weight of about 83,000 daltons in its fully glycosylated form, while miniplasmin has a molecular weight of about 38,000 daltons, and microplasmin has a molecular weight of about 26,500 daltons in the reduced form and about 29,000 daltons in the non-reduced form. Like plasmin, miniplasmin and microplasmin possess catalytic activity. An advantage of miniplasmin and microplasmin over plasmin is their smaller size compared to plasmin. Thus, both microplasmin and miniplasmin are expected to have faster diffusion rates in the vitreous than plasmin (Xu, J. et al., *Pharmaceutical Research* 17: 664-669, 2000).

In one embodiment, a TPCD has a molecular weight of less than about 40,000 daltons. In another embodiment, a TPCD has a molecular weight of between about 20,000 and about 30,000 daltons. In yet another embodiment, a TPCD has a molecular weight of about 26,500 daltons in reduced form and about 29,000 daltons in non-reduced form. In a further embodiment a TPCD has a molecular weight less than about 20,000 daltons.

Microplasmin can be prepared by the autolytic reaction of plasmin and plasminogen in high alkaline solution having a pH ranging from about 9.5 to 11.5, as described in U.S. Pat. No. 4,774,087. Alternatively, microplasmin and miniplasmin can be prepared by recombinant methods as described in PCT application WO 02/50290. Briefly, DNA encoding miniplasminogen and microplasminogen are independently cloned into a yeast expression vector (for e.g., pPICZα A secretion vector from Invitrogen Corporation) that can be used to express these proteins in methylotropic yeasts (e.g., *Hansenula, Pichia, Candida*, and *Torulopsis*). Yeast clones that produce proteins with the highest miniplasmin and microplasmin activity are selected for large-scale production. These clones can be grown at any scale, but typically at about a 20 liter to about a 500 liter scale. The secreted miniplasminogen or microplasminogen are purified in a three-step process comprising cation exchange expanded bed chromatography, hydrophobic chromatography, and affinity chromatography. The purified microplasminogen and miniplasminogen obtained by this process are activated to their active forms using a molar ratio of a plasminogen activator (e.g., urokinase, streptokinase, staphylokinase, the SY162 staphylokinase variant, etc.). It should be noted that the recombinant process for producing miniplasmin and microplasmin can be extended to produce any TPCD. An advantage of using a recombinant TPCD compared to autologous plasmin enzyme is that the recombinant proteins can be prepared from large production batches resulting in enzymes of uniform activity. Because these proteins are of uniform activity, standardized protocols can be implemented. A further advantage is that these proteins could be readily available without the delay and other attendant problems associated with the isolation and purification of plasmin from each patient.

The TPCD obtained by the processes described above can be concentrated, stabilized and/or lyophilized. Methods of concentrating proteins are well known to those of ordinary skill in the art (see for example, *Protein Purification Methods: A Practical Approach*, Harris, E. L. V and Angal, S. (eds.), IRL Press, 1989; *A Guide to Protein Isolation* (Second Edition), Clive Dennison, Kluwer Academic Publications, 2003; and *Protein Methods* (Second Edition), Daniel M. Bollag, Michael D. Rozycki, Stuart J. Edelstein (eds.), Wiley, 1996).

Stabilization is a method of protecting a protein from degradation and/or inactivation through the use of one or more stabilizing agents (for e.g., by contacting a TPCD with a stabilizing agent, or purifying a TPCD in the presence of a stabilizing agent). Stabilizing agents include without limitation, tranexamic acid, hexanoic acid, lysine, serine, threonine, methionine, glutamine, alanine, glycine, isoleucine, valine, alanine aspartic acid, polyhydric alcohol, pharmaceutically acceptable carbohydrates, glucosamine, thiamine, niacinamide, any acidic buffer comprising citric acid, acetic acid, hydrochloric acid, carboxylic acid, lactic acid, malic acid, tartaric acid, or benzoic acid, and salts such as sodium chloride, potassium chloride, magnesium chloride, calcium chloride, and any derivatives or combinations thereof. One advantage of using stabilized, recombinantly produced TPCD compared to autologous plasmin enzyme is that these proteins are more stable than autologous plasmin enzyme, which is obtained by collecting blood and, purifying, preparing and storing plasmin enzyme on a patient-by-patient basis. Unlike autologous plasmin enzyme, which needs to be used very soon after its preparation, stabilized, recombinant TPCD can be used even after a significant period of time from the time of purification.

Lyophilization of a TPCD of the invention can be performed immediately after the concentration of the purified proteins or after stabilization. Methods of lyophilizing proteins are well known to those of ordinary skill in the art. The lyophilized TPCD can be stored in vials (e.g., glass) in any amount, but preferably, in amounts that can be readily reconstituted for use.

Lyophilized microplasmin, miniplasmin, or any other TPCD, can be reconstituted in an ophthalmologically acceptable carrier prior to being used for contacting the vitreous and/or aqueous humor. In one embodiment an ophthalmologically acceptable carrier is a sterile solvent having a pH and osmolarity that is compatible with the vitreous of the subject. Nonlimiting examples of ophthalmologically acceptable carriers are isotonic saline solution, balanced salt solution (BSS) and BSS PLUS®. A balanced salt solution typically contains: 0.64% sodium chloride, 0.075% potassium chloride, 0.048% calcium chloride dehydrate, 0.03% magnesium chloride hexahydrate, 0.39% sodium acetate trihydrate, 0.17% sodium citrate dihydrate, sodium hydride/hydrochloric acid to adjust the pH, and water.

The method of contacting the vitreous and/or aqueous humor using compositions comprising a TPCD will depend upon the particular subject, the severity of the condition being treated and the dosage required for therapeutic efficacy, and can be determined by a physician on a patient-by-patient basis. Any method of contacting the vitreous and/or aqueous humor that provides an effective amount of a TPCD to the vitreous and/or aqueous humor can be utilized. It should be understood that such contact with the vitreous and/or aqueous humor does not have to take place simultaneously with the administration of a composition comprising a TPCD. The contact may be delayed or occur over an extended period of time from the time of administration. One method of contacting the vitreous and/or aqueous humor is by one or more intraocular injections directly into the vitreous and/or aqueous humor respectively. The vitreous and/or aqueous humor can also be contacted by sub-conjunctival, intramuscular or intravenous injections. Any of these injections can be provided using a liquid solution comprising a TPCD according to procedures well known in the art. Alternatively, however, the vitreous and/or aqueous humor can be contacted with a TPCD by any other suitable method, which results in sufficient distribution of the TPCD to the vitreous and/or aqueous humor to treat or prevent the disorder, or a complication of a disorder, of the eye of a subject. A composition comprising a TPCD can also be administered by placing an intra-vitreal implantable devices including, but not limited to, OCUSERT® (Alza Corp., Palo Alto, Calif.) and VITRASERT® (Bausch and Lomb, Inc., Rochester, N.Y.). The present invention also envisions that the vitreous and/or aqueous humor can be contacted with a TPCD using a depot, sustained release formulation, or any implantable device so that a TPCD is supplied continuously.

Dosing regimens for TPCD can be readily determined by one of ordinary skill in the art and will vary depending on the patient and the effect sought. TPCD can be used at any dose, which brings about desirable therapeutic effects, including but not limited to vitreous liquefaction, posterior vitreous detachment, and/or clearing of blood, toxic materials or foreign substances from the vitreous cavity, without causing significant toxicity to the eye (especially the retina) or associated anatomical structures. Additionally, a TPCD may be administered as a single dose or in multiple doses. A typical TPCD dosage is in the range of about 0.005 mg to about 0.2 mg per eye. If injected, TPCD can be provided in a delivery volume of about 0.05 ml to about 0.3 ml of a sterile solvent (e.g. sterile BSS or BSS PLUS®) per eye. In those instances where a vitrectomy is to be performed, the TPCD is left in the vitreous and/or aqueous humor for between about 15 and 120 minutes before removal of the vitreous. In one embodiment of the invention, a dose of 0.125 mg of TPCD is delivered in 0.1 ml of sterile BSS or BSS PLUS® per eye. In another embodiment, a dose of 0.125 mg of TPCD is delivered in 0.1 ml of sterile BSS or BSS PLUS® per eye for about 15-120 minutes prior to vitrectomy.

The present invention also contemplates the use of compositions comprising more than one TPCD. Accordingly, in one aspect of the invention, the vitreous and/or aqueous humor is contacted with a composition comprising a first TPCD and a second TPCD. In one particular embodiment of this aspect of the invention, the first and second TPCD are selected from the group consisting of miniplasmin, recombinant miniplasmin, stabilized miniplasmin, stabilized, recombinant miniplasmin, variants of miniplasmin, microplasmin, recombinant microplasmin, stabilized microplasmin, stabilized, recombinant microplasmin, variants of microplasmin, and any combinations thereof. In another aspect of the invention, the vitreous and/or aqueous humor is contacted with a first composition comprising at least one TPCD and with a second composition comprising at least one TPCD. The TPCD can be the same or different proteins and can be administered at substantially the same time or at different times. Additionally, a TPCD can also be administered as a composition further comprising at least one second agent. Furthermore, the vitreous and/or aqueous humor may be contacted with a composition comprising at least one TPCD followed by a composition comprising at least one second agent or vice versa. This may be necessary where the time required for each of these compositions is different, i.e., where one compositions needs more time to act compared to the other. A second agent is any protein (but not a TPCD), chemical or other substance that is useful in treating or preventing eye disorders, or complications of an eye disorder. Such second agents are described in U.S. Pat. Nos. 4,820,516; 5,292,509; 5,866,120; 6,051,698; 6,462,071; 6,596,725; and 6,610,292. Non-limiting examples of second agents usable with the present invention include glycosaminoglycanase enzymes such as hyaluronidases, chondroitinase ABC, chondroitinase AC, chondroitinase B, chondroitin 4-sulfatase, chondroitin 6-sulfatase and B-glucuronidase; collagenase enzymes; dispase; RGD containing peptides such as RGD, GRGDS, GRGDTP, Echistatin and Falvoridin; anti-integrin antibody; P2Y receptor antagonists; urea, hydroxyurea, thiourea and anti-angiogenic agents such as, but not limited to, vascular endothelial growth factor (VEGF) inhibitors (e.g., anti-VEGF antibodies, VEGF aptamers, soluble VEGF receptors, etc.) and placental growth factor (PlGF) inhibitors (e.g., anti-PlGF antibodies, PlGF aptamers, soluble VEGF receptors, etc.). Most of these second agents are themselves capable of promoting vitreous liquefaction and/or inducing posterior vitreous detachment. Anti-angiogenic second agents could be useful in preventing neo-vascularization in the eye. Expression of VEGF and/or PlGF from an hypoxic retina are thought to result in the development of extraretinal neovascularization. Thus, inhibiting VEGF and/or PlGF would be an effective way to prevent neovascularization.

A composition comprising a TPCD is useful to effect the liquefaction of the vitreous and/or the disinsertion or detachment of the vitreous from the retina and other tissues (e.g., epiretinal membranes, macula). As a result of this vitreous liquefaction and/or vitreous detachment, the tractional forces of the vitreous on the retina and other tissues are minimized and the rate of natural turnover of fluids within the vitreous is accelerated. Accordingly, compositions comprising a TPCD are particularly suitable for the treatment or prevention of many disorders of the eye, which benefit from vitreous liquefaction, posterior vitreous detachment, decreasing extraretinal neovascularization and/or accelerated clearance of toxins or other deleterious substances (e.g., angiogenic factors, edema fluids, hemorrhagic blood etc.) from the posterior chamber of the eye and/or tissues adjacent to the posterior chamber (e.g., retina or macula). Examples of such eye disorders include, but are not limited to, retinal detachment, retinal tear, vitreous hemorrhage, diabetic vitreous hemorrhage, proliferative diabetic retinopathy, non-proliferative diabetic retinopathy, age-related macular degeneration, macular holes, vitreomacular traction, macular pucker, macular exudates, cystoid macular edema, fibrin deposition, retinal vein occlusion, retinal artery occlusion, subretinal hemorrhage, amblyopia, endophthalmitis, retinopathy of prematurity, glaucoma and retinitis pigmentosa, and others in which the clinical symptoms of these disorders respond to TPCD administration. The present invention contemplates the treatment of disorders of the eye comprising contacting the vitreous with a composition comprising a TPCD. Such contact is expected to liquefy the vitreous and/or induce posterior vitreous detachment and/or clear the vitreous cavity of blood or other toxic substances and/or decrease extraretinal neovascularization, thereby treating or preventing the disorder.

The present invention is also directed to methods of preventing or inhibiting the onset of various disorders of the eye that are the result of, or exacerbated by, vitreous adhesion to the retina and vitreous contraction. In one embodiment, the methods of the present invention are able to prevent or inhibit the disorders, or complications resulting from a disorder in the eye of a subject without removing the vitreous from the eye. In particular, the invention is directed to a process of treating a patient with proliferative disorders or at risk of developing proliferative disorders, such as, but not limited to, a diabetic patient, by inducing posterior vitreous detachment as a prophylactic step in preventing or delaying the onset of disorders associated with vitreous contraction or neovascularization into the vitreous. In one embodiment of the invention, the composition is introduced into the eye of a diabetic patient to inhibit progression of diabetic retinopathy. Preferably, the composition is introduced into the eye before the proliferative disorders occur. In one embodiment, the composition is introduced into the vitreous of the eye before the onset of proliferative disorders and allowed to remain in the eye indefinitely without removing the vitreous from the eye. In further embodiments, the invention is directed to a process for inhibiting complications in central and branch retinal vein occlusion, such as retinal neovascularization and macular edema by inducing posterior vitreous detachment in a patient in need of such treatment. The present invention provides a process for treating impending or full-thickness macular hole (whether idiopathic or traumatic) by inducing posterior vitreous detachment. Preventing or reducing the incidence of retinal detachment, retinal tears and retinal hemorrhage caused by vitreous contraction can be achieved by inducing posterior vitreous detachment before such disorders occur and without removing the vitreous from the eye.

Many ophthalmic disorders have as a causative component, a destabilization of the blood-retina membrane. This destabilization permits various components (e.g., serum components, lipids, proteins) of the choriocapillaries to enter the vitreal chamber and damage the retinal surface. This destabilization is also a precursor to vascular infiltration of the vitreal chamber, known as neovascularization. Neovascularization of the vitreous is dependent on the matrix of the vitreous. Thus, liquefaction of the vitreous, which removes the matrix in the form of the polymerized vitreous, blocks neovascularization. In one embodiment, the invention provides a method of treating or preventing eye disorders by preventing or reducing the incidence of retinal neovascularization comprising contacting the vitreous with a composition comprising a TPCD.

Several ophthalmological disorders including diabetic retinopathy and trauma result in the rupture or leakage of retinal blood vessels with resultant bleeding into the vitreous (i.e., vitreous hemorrhage). Vitreous hemorrhage typically manifests as clouding or opacification of the vitreous and is sometimes, but not always, accompanied by tearing or detachment of the retina. In cases where the vitreous hemorrhage is accompanied by a retinal tear or detachment, it is important that such retinal tear or detachment be promptly diagnosed and surgically repaired. Failure to promptly diagnose and repair the retinal tear or detachment may allow photoreceptor cells of the retina, in the region of the tear or detachment, to become necrotic. Necrosis of the photoreceptor cells of the retina may result in loss of vision. Furthermore, allowing the retinal detachment to remain unrepaired for such extended period of time may result in further vitreous hemorrhage and/or the formation of fibrous tissue at the site of the hemorrhage. Fibrous tissue may result in the formation of an undesirable permanent fibrous attachment between the vitreous body and the retina. In the absence of any treatment, hemorrhagic clouding of the vitreous can take between 6-12 months or longer to clear sufficiently to allow trans-vitreal viewing of the retina. In such cases, where a physician would need to repair any part of the retinal surface, or where a physician would need to view the retinal surface of a patient that is prevented by an opaque or cloudy vitreous, a microsurgical procedure known as vitrectomy may need to be performed. This procedure involves removal of all or a portion of the vitreous with a microsurgical cutter and the replacement of the vitreous with a clear liquid or other substance that allows the ocular cavity to maintain its shape. Standard vitrectomy surgical procedures are well known to those of ordinary skill in the art. In one embodiment, the present invention contemplates contacting the vitreous with a composition comprising at least one TPCD as an adjunct to vitrectomy. In other embodiments, the vitreous is contacted with the composition comprising at least one TPCD in the absence of performing a vitrectomy.

The invention is illustrated further by the following examples, which are not to be construed as limiting the invention in scope or spirit to the specific procedures described therein. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Vector Construction for Expression of Human Microplasminogen and Human Miniplasminogen in *Pichia pastoris*

(a) The pPICZα A Vector

The pPICZα A secretion vector purchased from Invitrogen Corporation (Carlsbad, Calif.) was used to direct expression and secretion of recombinant human microplasminogen and miniplasminogen in *Pichia pastoris*. Notable features of this vector include: (i) a 942 by fragment containing the alcohol oxidase 1 (AOX1) promoter that allows methanol-inducible, high level expression of recombinant protein in *Pichia*, as well as targeted plasmid integration to the AOX1 chromosomal locus; (ii) the native transcription termination and polyadenylation signal from the AOX1 gene; (iii) an expression cassette conferring zeocin resistance to *Escherichia coli* and *Pichia pastoris;* (iv) a ColE1 origin of replication for propagation and maintenance of the plasmid in *Escherichia coli*; (v) a c-myc epitope and a polyhistidine (6×His) tag, which can be used for protein detection and purification; and (vi) unique restriction sites (for example, Sac I, Pme I, BstXI) that permit linearization of the vector at the AOX1 locus for efficient integration into the *Pichia* genome.

In addition to the above features, this vector contains the secretion signal of the *Saccharomyces cerevisiae* α-factor prepropeptide, allowing expression of heterologous proteins as secreted proteins into the medium. The processing of the α factor mating signal sequence in pPICZα occurs in two steps:
1. the preliminary cleavage of the signal sequence by the KEX2 gene product occurring between arginine and glutamine in the sequence Glu-Lys-Arg*Glu-Ala-Glu-Ala, where * is the site of cleavage. However, the Glu-Ala repeats are not always necessary for cleavage by Kex2.
2. the Glu-Ala repeats are further cleaved by the STE13 gene product. In some cases where Ste13 cleavage is not efficient, the Glu-Ala repeats are left on the NH$_2$-terminus of the expressed protein of interest.

Engineered immediately downstream of the α factor signal sequence in the pPICZα A vector is a multi-cloning site with recognition sequences for the enzymes EcoR I, Sfi I, Kpn I, Xho I, Sac II and Xba I to facilitate the cloning of foreign genes. In addition to the Xho I site in the multiple cloning site, there is a Xho I recognition sequence at the carboxyl-terminus of the α factor secretion signal, immediately upstream of the Lys-Arg Kex2 cleavage site. This Xho I restriction site may be used to clone the gene of interest flush with the Kex2 cleavage site by using a PCR cloning approach and an appropriate forward primer to rebuild the sequence from the Xho I site to the arginine codon. The recombinant protein of interest will then be expressed with a native NH$_2$-terminus.

(b) Expression Vector Construction for Microplasminogen

The nucleic acid sequence encoding the human microplasminogen protein (amino acids 543 to 791 (SEQ ID NO: 4)) was amplified ("PCR-rescue") from the vector Fmyc-μPli (Lasters et al. in *Eur. J. Biochem.* 244:946, 1997) using the Advantage cDNA polymerase mix available from Clontech (Palo Alto, Calif.). After a DNA template denaturation step of 3 minutes at 94° C., 30 rounds of thermal cycling were performed (30 seconds at 94° C., 30 seconds at 50° C., 30 seconds at 72° C.), followed by a 2 minutes final elongation step at 72° C. The following oligonucleotide primers LY-MPLG1 (sense) and LY-MPLG2 (antisense) were used in this reaction:

```
LY-MPLG1:
                                        (SEQ ID NO: 1)
5' GGGGTATCT CTC GAG AAA AGA GCC CCT TCA TTT GAT
TG

LY-MPLG2:
                                        (SEQ ID NO: 2)
5' GTTTTTGT TCT AGA TTA ATT ATT TCT CAT CAC TCC
CTC
```

The LY-MPLG1 primer had an annealing region corresponding to residues 543-548 of human plasminogen (Ala-Pro-Ser-Phe-Asp-Cys) preceded by a non-annealing extension which included the last four residues of the α factor mating signal (Leu-Glu-Lys Arg). In this extension, the Leu-Glu codons determine the Xho I restriction site (underlined) allowing the cloning of the gene of interest flush with the Kex2 cleavage site. The LY-MPLG2 primer had an annealing region corresponding to the last seven residues of plasminogen, followed by a TAA stop-codon and a non-annealing region comprising a Xba I recognition sequence (underlined).

The amplified fragment having the expected size (~780 bp) was digested with Xho I and Xba I, and directionally cloned into the vector pPICZα A. The recipient vector-fragment was prepared by Xho I and Xba I restriction, and purified from agarose gel using the Qiaquick gel extraction kit (Qiagen GmbH, Germany). The *E. coli* strain TG1 (DSMZ collection #1208, Germany) was transformed with the ligation mixture, and zeocin resistant clones were selected. Based on restriction analysis, a plasmid clone containing an insert of the expected size was retained for further characterization. Sequence determination of the vector pPICZα-MPLG1 (clone #5) using the primers 5'AOX and 3'AOX, which were provided in the EasySelect *Pichia* expression kit from Invitrogen Corporation (Carlsbad, Calif.), confirmed the precise insertion of the microplasminogen coding region fused to the α factor mating signal, as well as the absence of unwanted mutations in the coding region.

The determined nucleotide sequence and the deduced amino-acid sequence of human microplasminogen used are represented in SEQ ID NO: 3 and SEQ ID NO: 4, respectively. Compared to the sequence previously determined by Forsgren et al. in *FEBS Lett.* 213: 254, 1987, the nucleotide sequence differs in 10 positions. However, the amino acid sequence was identical.

(c) Expression Vector Construction for Miniplasminogen

A pPICZα-derived secretion vector was constructed as follows for miniplasminogen expression, making use of the hereinabove described pPICZα-MPLG1 vector.

A 500 bp DNA fragment encoding kringle five and part of the catalytic domain of the miniplasminogen protein (amino acids 444 to 604 of SEQ ID NO:10) was amplified ("PCR-rescue") from the vector FdTet-SN-miniPlg (Lasters et al., cited supra). After a DNA template denaturation step of 3 minutes at 94° C., 30 rounds of thermal cycling were performed (10 seconds at 94° C., 10 seconds at 50° C., 15 seconds at 72° C.), followed by a 2 minutes final elongation step at 72° C. The following oligonucleotide primers LY-MINPLG1 (sense) and LY-MINPLG2 (antisense) were used in this reaction:

LY-MINPLG1:
(SEQ ID NO: 5)
5' GGGGTATCT CTC GAG AAA AGA GCA CCT CCG CCT GTT

GTC CTG CTT CC

LY-MINPLG2:
(SEQ ID NO: 6)
5' GCA GTG GGC TGC AGT CAA CAC CCA CTC

The LY-MINPLG1 primer has an annealing region corresponding to residues 444-452 of plasminogen (Ala-Pro-Pro-Pro-Val-Val-Leu-Leu-Pro) preceded by a non-annealing extension which included the last four residues of the factor mating signal (Leu-Glu-Lys-Arg). In this extension, the Leu-Glu codons determine the Xho I restriction site (underlined) allowing the cloning of the gene of interest flush with the Kex2 cleavage site.

The LY-MINPLG2 primer has an annealing region corresponding to the residues 596-604 of human plasminogen (Glu-Trp-Val-Leu-Thr-Ala-Ala-His-Cys). This annealing region of the catalytic domain, also present in the microplasminogen expression vector, comprises a unique Pst I recognition sequence (underlined).

The amplified fragment having the expected size was digested with Xho I and Pst I, and directionally cloned into the recipient vector fragment derived from pPICZα-MPLG1 (described above). The recipient vector-fragment was prepared by Xho I and Pst I restriction, and purified from agarose gel using the Qiaquick gel extraction kit (Qiagen GmbH, Germany). The E. coli strain TG1 (DSMZ collection #1208, Germany) was transformed with the ligation mixture, and zeocin resistant clones were selected. Based on restriction analysis, a plasmid clone containing an insert of the expected size was retained for further characterization. Sequence determination of the vector pPICZα-KMPLG1 (clone #3), using the primers 5'AOX and 3'AOX, confirmed the precise insertion of the amplified fragment fused to the α-factor mating signal, as well as the absence of any mutations in the cloned region.

EXAMPLE 2

Method of Preparing Recombinant, Stabilized Microplasmin (a) Transformation of Pichia with pPICZα-MPLG1
Ten μg of the vector pPICZα-MPLG1 was digested with Pme I, which linearizes the vector in the 5' AOX1 region. The DNA was precipitated and concentrated to about 0.33 μg/μl in sterile distilled water, and 5 μl was used to transform competent Pichia pastoris X33 cells prepared according to the manual provided in the EasySelect Pichia expression kit.
(b) Selection of a High-Expression Strain
The selection of a high-expression strain was performed as follows. Zeocin resistant transformants were selected on YPDSZ plates (1% yeast extract, 2% peptone, 2% glucose, 1M sorbitol, 2% agar, 100 μg/ml zeocin). Thirty-four single colonies were inoculated in 10 ml BMYZ-glycerol medium (1% yeast extract, 2% peptone, 1% glycerol, 100 mM potassium phosphate, pH 6.0, 1.34% yeast nitrogen base, $4\times10^{-5}$% biotin, 100 μg/ml zeocin) in 50 ml Falcon tubes and cultured for 16 hours at 30° C. The cells were pelleted and re-suspended in 2 ml of BMYZ-methanol medium (same as BMYZ-glycerol but with 0.5% methanol instead of glycerol) to induce expression from the AOX1 promoter, and cultured for 40 hours. 4 pulses of 0.5% methanol were supplied to the cultures over this period (after 6, 22, 26 and 30 hours). At the end of the induction culture, the presence of microplasminogen in the culture supernatant was estimated as described by Lijnen et al. in *Eur. J. Biochem.* 120:149, 1981. Briefly, the microplasminogen in pure or 10-fold diluted supernatants was incubated with urokinase for 30 minutes to activate microplasminogen to microplasmin. The generated microplasmin activity, as determined by its amidolytic activity measured with the chromogenic substrate S2403 (available from Chromogenix, Antwerp, Belgium) at different times, was compared to the activity of known amounts of purified plasmin or microplasmin preparations. The clone X33-MPLG1 #5, showing the highest microplasmin activity after urokinase activation, was selected for subsequent large scale production. This clone was deposited under the provisions of the Budapest Treaty with the Belgian Coordinated Collections of Microorganisms (BCCM-MUCL-COLLECTION) on Dec. 12, 2001, under Accession Number MUCL 43676.
(c) Fermentation
Fermentation of X33-MPLG1#5 at a 50 liter scale was carried out in four steps as follows. Two liter flask cell cultures were performed for 23 hours at 30° C. in 400 ml YSG+ (6 g/l of yeast extract, 5 g/l of soya peptone, 20 g/l of glycerol) using an inoculum of 0.7 ml (of cell bank vial number glycerol OOC17) and 270 rpm agitation, yielding (at the end of the pre-culture step) an OD600 of 15. Fermentation was then performed in a MRP80 fermentation device in 30 l basal medium (26.7 ml/l H3PO4 85%, 1.05 g/l CaSO4.2H2O, 18.2 g/l K2SO4, 14.9 g/l MgSO4.7H2O, 4.13 g/l KOH, 40 g/l of 100% glycerol and 4.76 ml/l PTM1 salt solution [comprising 6 g/l CuSO4.5H2O, 0.08 g/l NaI, 3.36 g/l MnSO4.H2O, 0.2 g/l NaMoO4.2H2O, 0.02 g/l Boric acid, 0.82 g/l CoCl2.6H2O, 20 g/l ZnCl2, 65 g/l FeSO4.7H2O, 0.2 g/l d-biotin and 5 ml/l HSSO4]), using 600 ml inoculum at 30° C. with an air flow of 50 l/min at atmospheric pressure, dissolved oxygen (DO)>20% and 200-500 rpm agitation, pH being maintained at 5.8 with 12.5% ammonia. At 24 hours and OD 600 of 50 (end of batch step), glycerol depletion was evidenced by a rapid increase of dissolved oxygen. Glycerol feeding (632 g/l glycerol 100% and 12 ml/l PTM1) increased the OD 600 up to 258 in 24 hours. Methanol feeding was then carried out with an increasing flow of up to 250 ml/h within 6 hours, which was maintained for 66 hours using 988 ml/l methanol and 12 ml/l PTM1 to reach an OD 600 of 352 at the end of culture. Fermentation of X33-MPLG1#5 at a 350 liter scale provided proportionally similar results.
(d) Purification
The harvest was then purified in a three-steps process comprising cation exchange expanded bed chromatography, hydrophobic chromatography and affinity chromatography as follows:
i) Cation Exchange Expanded Bed Chromatography
Cation exchange expanded bed adsorption chromatography was conducted with Streamline SP (available from Pharmacia Biotechnology, Cat. No. 17-0993-01/02) packed in a Streamline 200 column (Pharmacia Biotechnology Cat No.

18-1100-22) with a bed volume of 5,120 cm³, expanded and equilibrated by applying an upward flow of 1 M NaCl, 25 mM sodium acetate (CH₃COONa.3 H₂O) buffer, pH 6.0, for two column volumes followed by column volumes of 25 mM sodium acetate buffer, pH 6.0. The fermentation broth was on line diluted (7×) with water and passed upwards through the expanded bed at a flow rate of 1000 ml/min. Loosely bound material was washed out with the upward flow of 25 mM sodium acetate buffer pH 6.0. The column adaptor was then lowered to the surface of the sedimented bed at a height of 16.3 cm. Flow was reversed and the captured proteins eluted with 2 column volumes of 0.5 M NaCl, 25 mM sodium acetate buffer, pH 6.0. Solid ammonium sulfate was added to the eluted Streamline fraction to reach 30% saturation (164 g ammonium sulfate per liter of eluted Streamline fraction) and the mixture was gently stirred at 4-8° C. for 1 hour.

ii) Hydrophobic Chromatography

Hydrophobic chromatography was conducted with Hexyl TSK 650C (available from Toso-Haas Cat. No. 19027) packed in a Vantage 180/500 column (available from Millipore, Cat. No. 87018001) with a packed volume of 2,700 cm³ at 4-8° C. The eluted streamline fraction was loaded on the column at a flow rate of 38 l/hour. The column was then washed with 1.5 column volumes of 25 mM sodium acetate buffer, pH 6.0, containing 164 g/l ammonium sulfate and eluted from the column with 7 column volumes of 25 mM sodium acetate buffer, pH 6.0.

iii) Affinity chromatography

Affinity chromatography was conducted with Blue Sepharose 6 Fast Flow (available from Pharmacia Biotechnology, Cat. No. 17-0948-02/03) packed in a Vantage 130/500 column (available from Millipore, Cat. No. 87013001) with a packed volume of 3,186 cm³ at 4-8° C. The eluted fraction was loaded on the column at a flow rate of 20 l/hour, and washed with one column volume of 25 mM disodium hydrogenophosphate (Na₂HPO₄.12 H₂O) buffer, pH 7.0. The microplasminogen protein fraction was eluted from the column with 5 column volumes of 0.5 M NaCl, 25 mM disodium hydrogenophosphate buffer, pH 7.0, and kept frozen at −20° C. The purity of the material was above 98% as demonstrated by SDS gel electrophoresis.

(e) Quantitative Activation to and Stabilization of Microplasmin i) Quantitative Activation The activation of microplasminogen to microplasmin was performed at 23° C. for 30 minutes at a molar ratio of 0.5% of a staphylokinase variant SY162 in 0.5 M NaCl, 25 mM disodium hydrogenophosphate (Na₂HPO₄.12 H₂O) buffer, pH 7.0. SY162 is a staphylokinase variant with reduced immunogenicity comprising 12 amino-acid substitutions (K35A, E65Q, K74R, E80A, D82A, T90A, E99D, T101S, E108A, K109A, K130T and K135R) as compared to wild-type, as described by WO 99/40198. Solid ammonium sulfate was added to microplasmin at a final concentration of 1 M (132 g/l) and the mixture stirred at 4-8° C. for 15 minutes.

ii) Hydrophobic Chromatography

Hydrophobic chromatography was conducted with Phenyl Sepharose 6 Fast Flow (available from Pharmacia Biotechnology, Cat. No. 17-0965-03/05) packed in a BPG 100/500 column (available from Pharmacia Biotechnology, Cat. No. 18-1103-01) having a packed volume of 1,738 cm³, equilibrated with 4 column volumes of 25 mM Na₂HPO₄.12 H₂O buffer, pH 7.0, containing 0.1 M of the stabilizing agent, tranexamic acid (available from Bournonville Pharma, Braine-L'Alleud, Belgium) and 1 M (NH₄)₂SO₄ pH 7.0, at 4-8° C. The activated product was loaded on the column at a linear flow rate of 18 l/hour and washed with 4.5 column volumes of 25 mM Na₂HPO₄.12 H₂O buffer, pH 7.0, containing 0.1 M tranexamic acid and 1 M (NH₄)₂SO₄. Microplasmin was eluted from the column at a linear flow rate of 6 l/hour with 5 column volumes of 25 mM Na₂HPO₄.12 H₂O buffer, pH 7.0, containing 0.1 M tranexamic acid and 0.7 M (NH₄)₂SO₄ and equilibrated with phosphate buffered saline containing 0.1 M tranexamic acid. Staphylokinase variant SY162 was eluted from the column with 25 mM Na₂HPO₄.12H₂O buffer, pH 7.0 containing 0.1 M tranexamic acid. This procedure removed above 99% of staphylokinase from the microplasmin peak as demonstrated with a specific ELISA assay.

iii) Concentration and Diafiltration by Tangential Ultrafiltration

In this step, the eluate from step (ii) was concentrated and the buffer was exchanged for the low pH citric acid buffer. The tranexamic acid of step (ii) was removed during this step and microplasmin was stabilized by the low pH citric acid buffer.

Ultrafiltration was conducted with 2 Pellicon 2 Biomax membranes (5 kDa, 2.5 μm, available from Millipore, Bedford, Mass., Cat. No. P2B005A25) at 2-8° C. The membranes were mounted in a Pellicon 2 Process Holder connected to a Microgon Pump Cart System (available from Microgon, Laguna Hills, Calif.). The membranes were washed with purified water and membrane integrity tested before operation. Sanitization was performed by continuous recirculation with 0.5 M NaOH for 60 minutes and with 0.1 M NaOH during 60 minutes. The sanitization step deep cleans the membrane to eliminate any potential trace of protein left on the membrane before applying the sample. The membranes were then rinsed with 5 mM citric acid, pH 3.1, until the permeate reached a pH of 3.1. The pH of the Phenyl Sepharose eluate was adjusted to 3.1 and the protein was concentrated to 4 mg/ml by ultrafiltration. Diafiltration was performed for 60 to 90 minutes against 5 volumes of 5 mM citric acid, pH 3.1. Yields (expressed in grams) of three runs performed on a 50 liter fermentation apparatus are summarized in Table 2.

TABLE 2

|  | Run 1 | Run 2 | Run 3 |
| --- | --- | --- | --- |
| Fermentor | 220 | 240 | ND |
| Streamline | 50 | 79 | 130 |
| Hexyl | 36 | 37 | ND |
| Blue | 25 | 28 | 30 |
| Phenyl | 17 | 20 | 26 |
| Diafiltration | — | — | 22 |

(Key: ND: not determined)

iv) Sterile Filtration (0.2 μm)

This step was performed to ensure absence of microbial contamination.

Mannitol was added at 2-8° C. to a concentration of 1.5 g/g of protein and sterile filtration performed at 23° C. on a Millipak 100 filter (size 500 cm²) (available from Millipore, Cat. No. MPGL10CA3) and rinsed with about 500 ml of 5 mM citric acid, pH 3.1, with a peristaltic pump at a flow rate of 500 ml/minute. The filtrate was collected in a sterile and pyrogen free bag and stored at −20° C.

EXAMPLE 3

Method of Preparing a Recombinant, Stabilized Miniplasmin

About 15 μg of the vector pPICZα-KMPLG1 was digested in a 20 μl reaction with Pme I, which linearizes the vector in the 5' AOX1 region. The linear DNA (3 μg) was used to transform competent *Pichia pastoris* X33 cells prepared according to the manual provided in the EasySelect *Pichia* Expression kit.

The selection of high-expression strain was performed essentially as follows. Zeocin resistant transformants were selected on YPDSZ plates (as defined in example 2). Fifty isolated colonies were inoculated in 15 ml BMYZ-glycerol medium (as defined in example 2) in 50 ml Falcon tubes and cultured for 16 hours at 30° C. The cells were pelleted and re-suspended in 1.5 ml of BMYZ-methanol medium (as defined in example 2) to induce expression from the AOX1 promoter, and cultured for 40 hours. 3 or 4 pulses of 0.5% methanol were regularly supplied to the cultures over this period. At the end of the induction culture, the presence of miniplasminogen in the culture supernatant was estimated as described by Lijnen et al. (cited supra). Briefly, the miniplasminogen in 10-fold diluted supernatants was incubated with streptokinase for 10 minutes to form an active complex. The generated miniplasmin activity, as determined with the chromogenic substrate S2403 (see example 2) at different times, was compared to the activity of known amounts of a purified plasminogen preparation. In these conditions, all tested clones produced miniplasminogen with yields varying between 3 and 15 mg/l. The two clones X33-KMPLG1 #6 and X33-KMPLG1 #25, showing the highest miniplasmin activity, were selected for subsequent large scale production. These two clones were deposited under the provisions of the Budapest Treaty with the Belgian Coordinated Collections of Microorganisms (BCCM-MUCL-COLLECTION) on Dec. 4, 2003 and have been accorded Accession Number MUCL 45309 (clone X33-KMPLG1 #6) and Accession Number MUCL 45308 (clone X33-KMPLG1 #25).

EXAMPLE 4

Novel Method of Fixation

This experiment was carried out to establish a fixation technique that is reliable to investigate the effects of media and different agents on posterior vitreous detachment (PVD) in normal porcine eyes.

Freshly isolated porcine eyes obtained from the slaughterhouse were either immediately processed or allowed to sit at room temperature for up to 6 hours. The cornea was removed to facilitate fixation. Eyes were fixed in Peter's solution (1.25% glutaraldehyde/1% paraformaldehyde in 0.08 M cacodylate buffer pH 7.4) at 0° C. for 24 to 36 hours to stop enzymatic reactions. The eyes were then washed with 0.1 M cacodylate buffer pH 7.4 and progressively dehydrated in progressively higher concentrations of ethanol up to 100%.

Both the freshly processed eyes and the eyes allowed to sit for 6 hours showed no significant change in the ultrastructure of the retina, and the vitreous remained attached to the retinal surface. Thus, this method provides a non-traumatic fixation procedure for eye tissue and minimizes the possibility of the separation of the vitreous from the retinal surface. Furthermore, this procedure allows the whole retinal surface, from the optic nerve to the retinal periphery to be studied.

EXAMPLE 5

Effect of Microplasmin on the Vitreoretinal Interface in Post-Mortem Porcine Eyes This experiment was carried out to determine the ability of microplasmin to disinsert the posterior vitreous cortex from the inner limiting membrane of the retinal surface.

Microplasmin was used at the following doses: 0.0625, 0.125, 0.156, 0.25 and 0.390 mg, in a volume of 0.1 ml of the intraocular irrigating solution, BSS PLUS®. The pH of these microplasmin solutions ranged from 7.92 for the 0.0625 mg dose to 6.52 for the 0.390 mg dose.

The microplasmin solutions disclosed above were separately injected into the vitreous humor of eyes obtained from freshly slaughtered pigs at room temperature (24° C.). The eyes were fixed as described in Example 4, after 15 minutes, 30 minutes, 60 minutes or 120 minutes following injection of microplasmin. Posterior vitreous detachment (PVD) was observed after 1 hour of treatment with 0.0625 mg of microplasmin, whereas PVD was visible from about 30 minutes after the injection for all doses including and above 0.125 mg of microplasmin. This detachment was most apparent around 120 minutes post-injection (FIG. 4, Panel A), in all sections of the retina surface, except near the vitreous base (the zone extending from the peripheral retina to the ora serrata where the adhesion to the vitreous is strong). In addition to posterior vitreous detachment (FIG. 4, Panels B-E), electron microscopy showed that the structure of the vitreous was altered to have less fibrillary structure present. The fibrillar structure was modified to a more amorphous, ground glass consistency, which indicates liquefaction of the vitreous humor (FIG. 4, Panel F).

Figure 5:
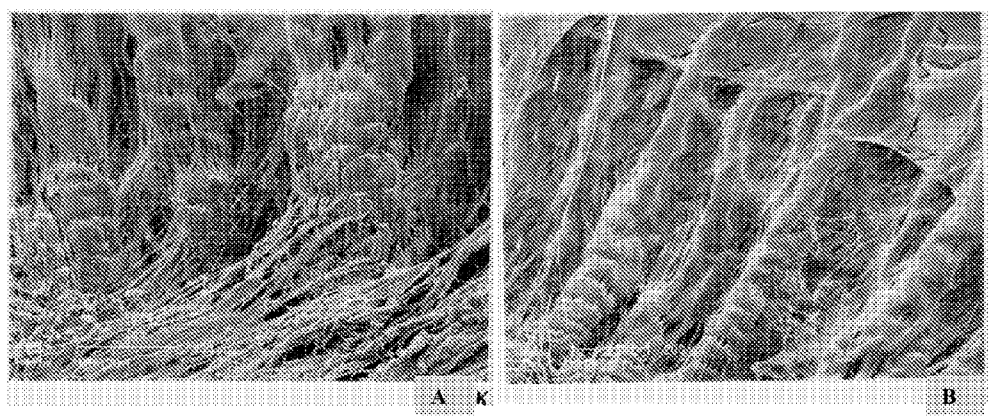
FIG. 5 shows that ciliary processes in the porcine eye are intact after 120 minute treatment with microplasmin (Panels A and B).

Doses lower than 0.25 mg did not result in any ocular or retinal toxicity as determined by gross examination or histopathology, including electron microscopy. In particular, there was no sign of autolysis. Vacuolation of cells is often seen as an early sign of autolysis and at doses lower than 0.390 mg, no vacuolation was observed. We also examined other ocular structures by electron microscopy (FIG. 5, Panels A and B). No structural alterations to the retina were observed at doses lower than 0.390 mg. However, in a few eyes treated with 0.25 mg of microplasmin, retinal elevations and small numbers of inflammatory cells were sparsely distributed on the retinal surface. Gross histology of the eye treated with the highest dose of microplasmin (0.390 mg), indicated that the retinal interface had a whitish appearance. Electron microscopy of this eye revealed that there were multiple small elevations in the retinal surface, which suggests localized retinal detachment.

These experiments show that microplasmin used at a dosage of 0.06 to 0.2 mg resulted in consistent separation of the posterior hyaloid without inducing any ultrastructural changes in the retina. The posterior hyaloid separation is not only at the optic nerve but also all the way to the vitreous base. The posterior hyaloid separation leaves a clear, smooth retinal surface on which no collagen fibers can be recognized using high-electron microscopic scanning (12,000× magnification), a magnification that is high enough to exclude the possibility of undetected fibers.

EXAMPLE 6

Posterior Vitreous Detachment in Human Post-Mortem Eyes

This experiment was performed to determine whether microplasmin could efficiently induce vitreoretinal separation in human eyes.

Methods (a) Dosage and Treatment of Human Post-Mortem Eyes

Twenty-six human globes with no known eye pathology were obtained from the Munich eye bank. These globes were removed from 13 donors, whose ages ranged from 34 to 69 years, within 19 hours of their death. After harvesting the cornea using a 14 mm diameter trephine, the 26 globes were incubated in a moist chamber at 37° C. for 15 minutes. 0.2 ml of microplasmin was then injected into the vitreous cavity of thirteen eyes. Specifically, 1.25 mg of microplasmin was diluted with 4 ml, 2 ml, or 1.5 ml of the intraocular irrigating solution, BSS PLUS® to achieve concentrations of 0.3125 mg/ml, 0.625 mg/ml, and 0.9375 mg/ml respectively. A total volume of 0.2 ml of these solutions was injected into the vitreous cavity, resulting in a final dose of 62.5 µg, 125 µg, and 188 µg of microplasmin respectively within the eye. The 13 fellow eyes, which served as controls, received an injection of 0.2 ml of balanced salt solution (BSS PLUS®).

Of the 13 eyes treated with microplasmin, 9 eyes were treated by an intravitreal injection of microplasmin alone. A dose of 62.5 µg of microplasmin (pH 7.4) was injected into the vitreous cavity of two eyes; a dose of 125 µg of microplasmin (pH 7.2) was injected into the vitreous cavity of 5 eyes; and a dose of 188 µg of microplasmin (pH 7.2) was administered in 2 eyes. Of the remaining 4 eyes, two were treated with 62.5 µg of microplasmin and 0.6 ml of sulfurhexafluoride ($SF_6$) and two were treated with 125 µg of microplasmin and 0.6 ml of sulfurhexafluoride ($SF_6$). The additional treatment with $SF_6$ was performed because of previous reports that plasmin only induces PVD in combination with vitrectomy or gas injection. The dosing and treatment discussed above are summarized in Table 3.

TABLE 3

| Number of eyes | Dose of microplasmin in µg | Treatment |
| --- | --- | --- |
| 2 | 62.5 | Intravitreal injection |
| 5 | 125 | Intravitreal injection |
| 2 | 188 | Intravitreal injection |
| 2 | 62.5 | Intravitreal injection and gas tamponade (0.6 ml $SF_6$) |
| 2 | 125 | Intravitreal injection and gas tamponade (0.6 ml $SF_6$) |

Following treatment, all eyes were incubated at 37° C. for 30 minutes. After that time, the globes were placed in 4% paraformaldehyde, and 0.1 ml of fixative (4% paraformaldehyde) was also injected into the vitreous cavity to stop enzymatic action within the eye. The globes that were treated with microplasmin and $SF_6$ were fixed with the posterior pole in an upright position.

(b) Scanning and Transmission Electron Microscopy

The globes were then hemisected along the pars plana, and the anterior segment was discarded. A corneal trephine of 12.5 mm diameter was slowly moved through the vitreous and the posterior pole was punched out. Retinal specimens for scanning and transmission electron microscopy were then obtained from the posterior pole using a corneal trephine of 4 mm diameter.

Retinal discs for scanning electron microscopy were post-fixed in 2% osmium tetroxide (Dalton's fixative), dehydrated in ethanol, dried to the critical point, sputter-coated in gold, and photographed using a ISM-35 CF electron microscope (JEOL®, Tokyo, Japan).

Specimens for transmission electron microscopy were post-fixed in Dalton's fixative, dehydrated, and embedded in EPON™. Semithin sections were stained with 2% toluidine blue. Ultrathin sections were contrasted contrasted with uranyl acetate and lead citrate, and analyzed using a Zeiss EM 9 electron microscope (Zeiss, Jena, Germany).

Two observers independently evaluated the electron micrographs. Each observer evaluated the degree of vitreoretinal separation by deciding whether a continuous or discontinuous network of collagen fibrils covered the inner limiting membrane (ILM), or whether single or sparse collagen fibrils were present at the ILM, or whether the ILM was devoid of any collagen fibrils (bare ILM).

Results (a) Scanning Electron Microscopy

Figure 6:
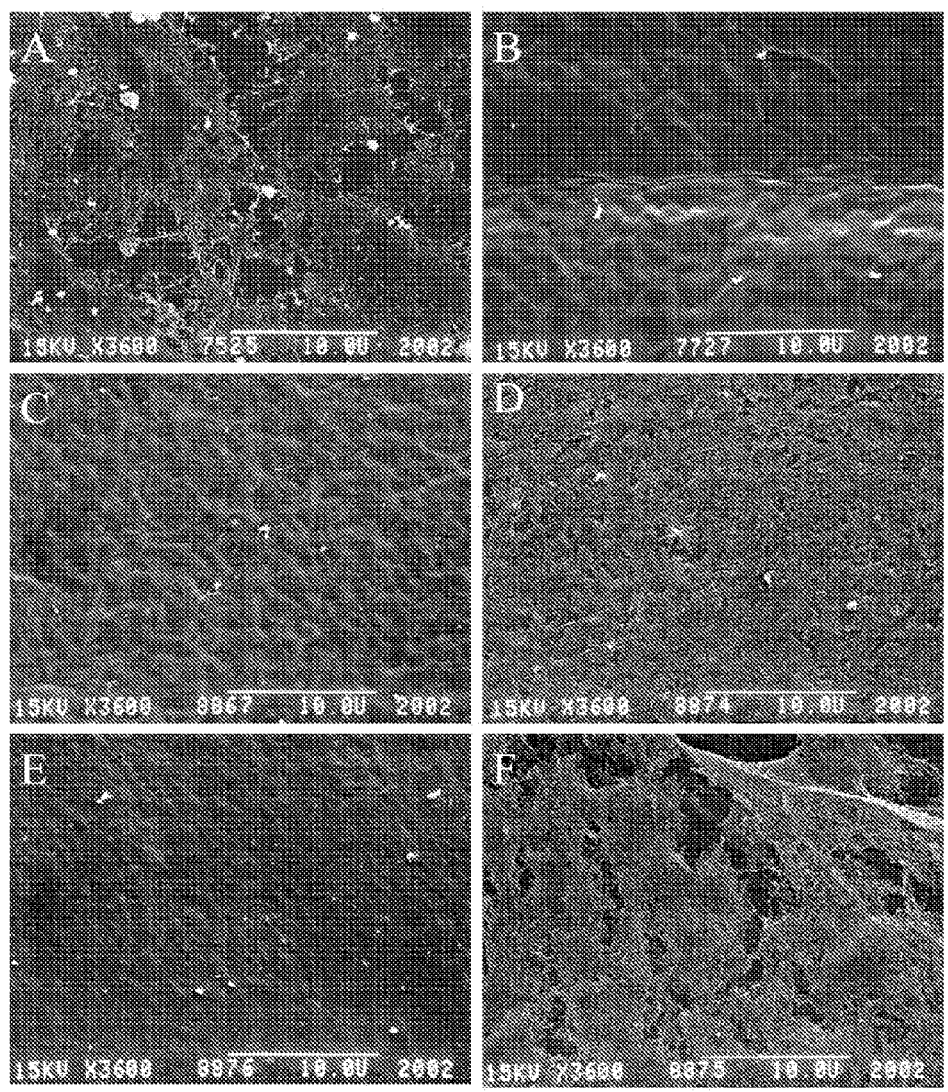
FIG. 6 provides scanning electron micrographs (magnification of 3600×) of the vitreoretinal interface in human post-mortem eyes. Intravitreal injection of 62.5 µg of microplasmin resulted in posterior vitreous detachment (PVD) leaving discontinuous remnants of collagen fibrils covering the ILM (Panel A). 125 µg (Panel B) and 188 µg (Panel C) of microplasmin produced complete PVD and a bare ILM. Panel D shows the compression of collagen fibrils towards the ILM in an eye treated with 62.5 µg microplasmin and gas. Panel E shows complete PVD following treatment with 125 µg microplasmin and gas. Unlike the PVD observed in microplasmin treated eyes, there is a dense network of collagen fibrils in the control eye (Panel F).

Scanning electron microscopy (SEM) of post-mortem human eyes injected with 62.5 µg of microplasmin revealed a posterior vitreous detachment leaving a discontinuous network of collagen fibrils covering the ILM (FIG. 6, Panel A). SEM of eyes injected with 125 µg (FIG. 6, Panel B) and 188 µg (FIG. 6, Panel C) of microplasmin respectively revealed a bare ILM consistent with complete vitreoretinal separation. Both these higher doses resulted in a similar ultrastructure of the vitreoretinal interface.

In eyes injected with 62.5 µg of microplasmin and $SF_6$, remnants of cortical vitreous covering the ILM were observed (FIG. 6, Panel D). However in eyes injected with 125 µg of microplasmin followed by gas tamponade, complete vitreoretinal separation consistent with a bare ILM was observed (FIG. 6, Panel E).

In contrast to the microplasmin-treated eyes discussed above, control eyes did not exhibit posterior vitreous detachment as determined by SEM (FIG. 6, Panel F). These results are summarized in Table 4.

TABLE 4

| Dose of microplasmin in µg | Treatment | Degree of residual cortical vitreous | |
| --- | --- | --- | --- |
| | | Treated eyes | Control eyes |
| 62.5 | Intravitreal injection | ++ | +++ |
| 125 | Intravitreal injection | − | +++ |
| 188 | Intravitreal injection | − | +++ |
| 62.5 | Intravitreal injection and gas tamponade | ++ | +++ |
| 125 | Intravitreal injection and gas tamponade | − | +++ |

[Key: +++ continuous network of collagen fibrils; ++ discontinuous network of collagen fibrils; + sparse collagen fibrils; − no collagen fibrils, bare ILM]

(b) Transmission Electron Microscopy

Figure 7:
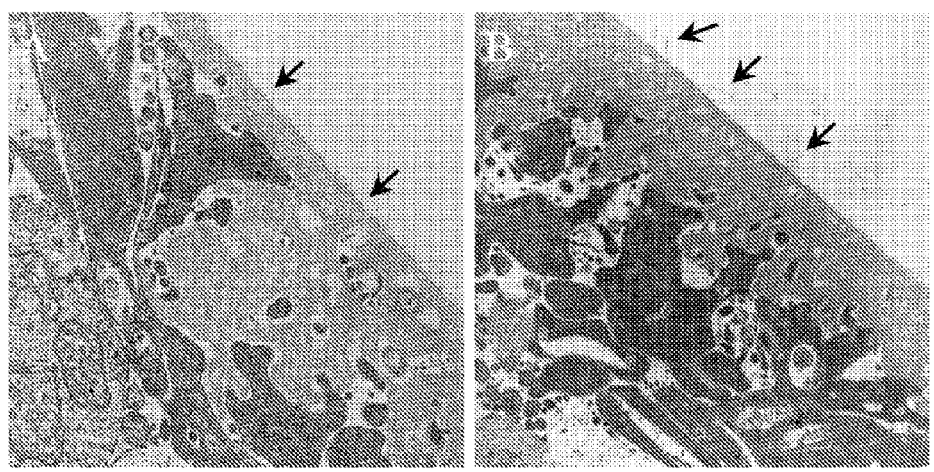
FIG. 7 provides transmission electron micrographs of the ILM in human post-mortem eyes. Note the absence of collagen fibrils (arrows) on the ILM in the microplasmin-treated eye (Panel A, magnification 13,600×). In contrast, collagen fibrils are still present (arrows) on the ILM in the control eye (Panel B; magnification 6800×).

The intraretinal morphology of all microplasmin-treated eyes was unchanged compared to control eyes. The ultrastructure of the ILM was well preserved in microplasmin-treated eyes (FIG. 7, Panel A), as compared to the control eye (FIG. 7, Panel B).

Conclusion

These data indicate that intravitreal injection of microplasmin can induce a cleavage between the vitreous cortex and the inner limiting membrane of the human eye without vitrectomy or any other surgical intervention. 125 µg of microplasmin cleaves the human vitreoretinal junction within 30 minutes. In terms of enzymatic action, 125 µg of microplasmin is the equivalent dose of 2 U of plasmin (Sigma-Aldrich, Munich, Germany), which caused complete vitreoretinal separation in pig cadaver eyes and in human donor eyes. These data also show that the application of a gas bubble into the vitreous of a microplasmin-treated eye did not affect the dose needed to cleave the vitreoretinal junction.

EXAMPLE 7

In Vivo Analysis of Microplasmin-Induced Posterior Vitreous Detachment

The purpose of these experiments was to determine the utility of microplasmin for PVD in vivo.

Methods (a) The Feline Model

The feline retina has been extensively studied by anatomists and physiologists making this a useful model to assess the safety of pharmacologically induced PVD. Like the human retina, the cat retina is rod-dominated and has an intraretinal circulation, outside the fovea. This is in contrast to the rabbit retina, which has no intraretinal vessels. The rabbit inner retina is perfused by vasculature that lies on its vitreal surface, and this limits the value of experimental studies primarily focused on the vitreoretinal interface in the rabbit. For years, the feline model has provided high-quality data on the cellular responses of the retina to detachment. Thus, we used a feline model to study the utility of microplasmin in effecting PVD in vivo.

Five adult domestic cats aged between 12 and 23 months were anesthetized with an intramuscular injection of 0.5 ml of ketamine (Ketaset, Park-Davis, Eastleigh, UK) and 0.3 ml of medetomide (Dormitor, Pfizer, UK). The anesthetized cats received an intravitreal injection of 14.5 μg or 25 μg of microplasmin, while the fellow eyes of these cats received an injection of balanced salt solution (BSS-PLUS®) and served as controls. Of the 5 cats used in this study, 3 cats received an intravitreal injection of 25 μg of microplasmin. One of these cats was sacrificed after one day of receiving the injection; the second was sacrificed after 3 days and the third was sacrificed after 3 weeks. The two remaining cats were injected with 14.5 μg microplasmin. Of these, one was sacrificed after 3 days while the other was sacrificed after 3 weeks.

(b) Scanning and Transmission Electron Microscopy

The globes were removed from the sacrificed cats, fixed and processed for electron microscopy as described for human post-mortem eyes in Example 6. Electron micrographs were evaluated independently by two observers. Each observer evaluated the degree of vitreoretinal separation by deciding whether a continuous or discontinuous network of collagen fibrils covered the ILM, or whether single or sparse collagen fibrils were present at the ILM, or whether the ILM was devoid of any collagen fibrils.

(c) Confocal Microscopy

The eye specimens were rinsed in phosphate buffered saline (PBS) and orientated in 5% agarose (Sigma, St Louis Mo., USA) prepared in PBS. One hundred micrometer thick sections were cut using a vibratome (Technical Products International, Polysciences, Warrington, Pa., USA) and incubated in normal donkey serum (1:20; Dianova, Hamburg, Germany) in PBS containing 0.5% bovine serum albumin (BSA; Fisher Scientific, Pittsburgh, Pa., USA), 0.1% Triton X-100 (Roche Boehringer, Mannheim, Germany) and 0.1% sodium azide (Sigma-Aldrich, Munich, Germany) (this PBS solution containing BSA, Triton and azide is referred to as PBTA) overnight at 4° C. on a rotator. After removal of blocking serum, primary antibodies were added in six sets of pairs: anti-glial fibrillary acidic protein (GFAP; 1:500; DAKO, Hamburg, Germany) with anti-collagen IV (1:50; DAKO); anti-vimentin (1:50; DAKO) with anti-fibronectin (1:400; DAKO); anti-synaptophysin (1:50; DAKO) with anti-neurofilament (1:25; DAKO); anti-laminin (1:25; DAKO) with anti-CD 68 (1:50; DAKO); anti-red/green opsin (1:100; Santa Cruz Biotechnology, USA) with anti-rhodopsin (1:200; Santa Cruz Biotech); anti-blue opsin (1:100; Santa Cruz Biotech, Santa Cruz, Calif., USA) with anti-rhodopsin (1:200; Santa Cruz Biotech). The specifity of the antibodies used in this experiment is listed in Table 5.

TABLE 5

| Antibody | Specifity |
| --- | --- |
| Anti-glial fibrillic acidic protein (GFAP) | Intermediate filament proteins of Müller cells |
| Anti-vimentin | |
| Anti-neurofilament | Neurofilaments in ganglion cells and in horizontal cells |
| Anti-synaptophysin | Synaptic vesicles in plexiform layers |
| Anti-red/green opsin | Cones |
| Anti-blue opsin | |
| Anti-rhodopsin | Rods |
| Anti-fibronectin | Fibronectin |
| Anti-laminin | Laminin |
| Anti-collagen IV | Collagen type IV |
| Anti-CD68 | Macrophages |

After overnight incubation at 4° C. on a rotator, sections were rinsed in PBTA and incubated again overnight at 4° C. with the secondary antibody. Donkey anti-mouse and donkey anti-rabbit secondary antibodies were used for each combination of primary antibodies, conjugated to Cy2 or Cy3 (Dianova, Hamburg, Germany). All secondary antibodies were used at a dilution of 1:100, and all the antibodies were diluted in PBTA. The sections were then rinsed, mounted in N-propyl gallate in glycerol and viewed on a laser scanning confocal microscope (LSM 510, Zeiss, Germany).

Results (a) Scanning Electron Microscopy

Figure 8:
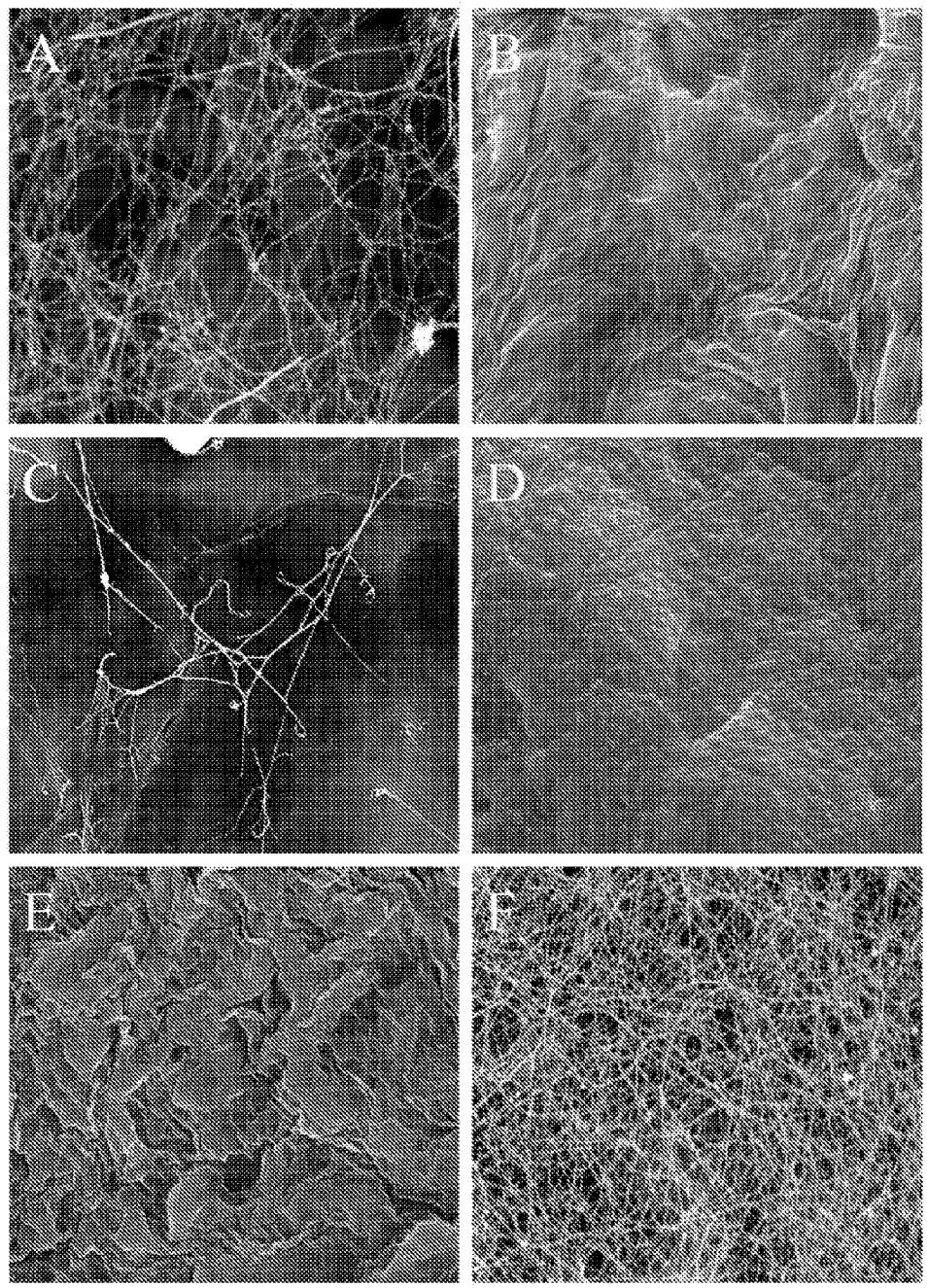
FIG. 8 presents scanning electron micrographs (magnification 3600×) of the vitreoretinal interface in cat eyes. Intravitreal injection of 25 µg of microplasmin left remnants of collagen fibrils on the ILM one day after treatment (Panel A). Three days after treatment, 25 µg of microplasmin resulted in complete PVD (Panel B). Remnants of collagen fibrils were observed three days following treatment with 14.5 µg of microplasmin (Panel C). A bare ILM was observed three weeks after injection of 14.5 µg of microplasmin (Panel D) and 25 µg of microplasmin (Panel E). In striking contrast, the control eye showed a dense attached cortical vitreous (Panel F).

One day following intravitreal injection of 25 μg microplasmin, sparse collagen fibrils covered the ILM (FIG. 8, Panel A). Three days after treatment, 25 μg microplasmin resulted in complete vitreoretinal separation (FIG. 8, Panel B); there were no remnants of collagen fibrils left on the vitreoretinal interface. The eye which received 14.5 μg of microplasmin revealed sparse collagen fibrils covering the ILM 3 days after the injection (FIG. 8, Panel C). 21 days after treatment, with 14.5 μg (FIG. 8, Panel D) and 25 μg of microplasmin (FIG. 8, Panel E) a bare ILM was observed. All fellow control eyes had a dense network of collagen fibrils covering the retina (FIG. 8, Panel F). These data are summarized in Table 6.

TABLE 6

| Dose of microplasmin in μg | Duration of treatment in days | Degree of residual cortical vitreous | |
| --- | --- | --- | --- |
| | | Treated eyes | Control eyes |
| 14.5 | 3 | + | +++ |
| 14.5 | 21 | − | +++ |
| 25 | 1 | + | +++ |
| 25 | 3 | − | +++ |
| 25 | 21 | − | +++ |

[Key: +++ continuous network of collagen fibrils; ++ discontinuous network of collagen fibrils; + sparse collagen fibrils; − no collagen fibrils, bare ILM]

(b) Light and Transmission Electron Microscopy

Figure 9:
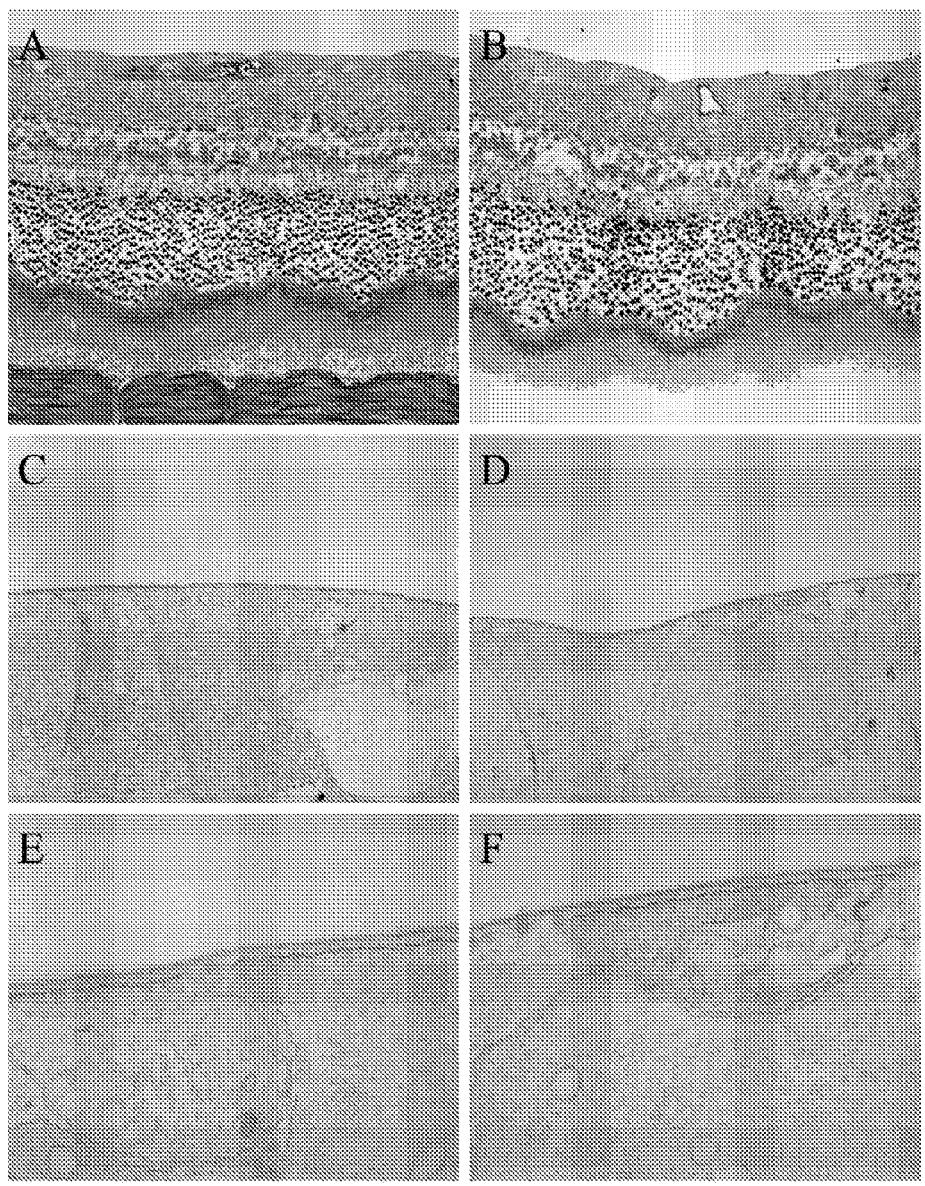
FIG. 9 presents the results of light microscopy studies of semi-thin sections of cat eyes. These studies showed that the normal cytoarchitecture of the retina observed in control eyes (Panel B) was also observed in microplasmin-treated eyes (Panel A). Transmission electron microscopy revealed a well-preserved inner retina and ILM in microplasmin-treated eyes (Panels C and E) as observed in control eyes (Panels D and F). The magnification used for Panels A and B was 250×; the magnification for Panels C and D was 6000×; while the magnification for Panels E and F was 30,000×.

Regarding the cytoarchitecture of the retina, no difference was observed between microplasmin-treated eyes (FIG. 9, Panel A) and control eyes (FIG. 9, Panel B). The ultrastructure of the inner retina and the ILM of microplasmin treated eyes (FIG. 9, Panels C and E) were well preserved compared to the inner retina and the ILM of control eyes (FIG. 9, Panels D and F).

(c) Laser Confocal Microscopy

Figure 10:
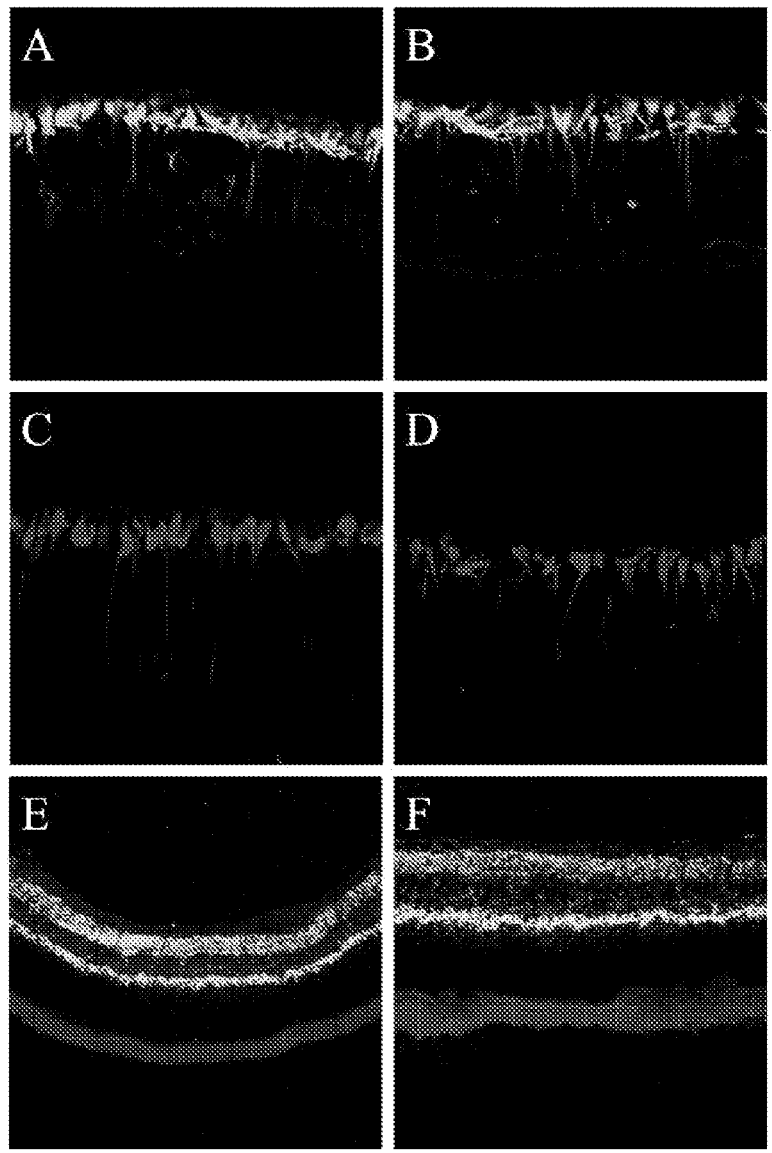
FIG. 10 presents the results of confocal laser scanning microscopy with probes to glial fibrillic acidic protein (Panels A and B, green) and vimentin (Panels C and D, red). There is no difference in the staining of GFAP and vimentin between microplasmin-treated eyes (Panels A and C) and control eyes (Panels B and D). Double-label immunohistochemistry with probes to synaptophysin (green) and neurofilament (red) also shows no difference between microplasmin-treated eyes (Panel E) and a control eyes (Panel F). Magnification for Panels A, B and C was 400×; magnification for Panel D was 250×; and magnification for Panels E and F was 160×.

In microplasmin-treated eyes and in control eyes, the endfoot portion of Müller cells was clearly labeled by anti-GFAP (FIG. 10, Panels A and B) and anti-vimentin (FIG. 10, Panels C and D). There was no extended staining of Müller cell processes beyond the inner nuclear layer. No significant staining was observed with anti-collagen IV and anti-fibronectin (data not shown). This may relate to species specifity of these antibodies. The ILM was stained by anti-laminin. Few macrophages were present in both treated eyes and control eyes. The ganglion cell axons and dendrites, the horizontal cells, and the inner and outer plexiform layer were clearly labeled by anti-neurofilament and anti-synaptophysin (FIG. 10, Panels E and F). The photoreceptor layer was labeled by anti-neurofilament. There was no difference between microplasmin-treated eyes (Panels A, C, E) and control eyes (FIG. 10, Panels B, D and F) at any time point of the study, with respect to any of the antibodies used.

Discussion

To assess the cleaving effect of microplasmin at the vitreoretinal interface in vivo, we administered two different doses into the vitreous cavity of five adult cats. The first dose we used was 25 µg of microplasmin, which is one-fifth of the dose that was found sufficient to induce complete PVD in human post-mortem eyes. Notably 25 µg of microplasmin is equivalent to 0.4 U of plasmin (Sigma), and clinically 0.4 U of autologous plasmin has been applied to the vitreous cavity of human eyes with macular holes and diabetic retinopathy. The second dose of 14.5 µg of microplasmin is equivalent to a dose of 25 µg of microplasmin in the human eye, if one adjusts for the smaller vitreous volume of the cat eye (roughly 60% of the vitreous volume of the human eye).

Three days following an intravitreal application of 25 µg of microplasmin in the cat eye, there was complete vitreoretinal separation, whereas one day after treatment some collagen fibrils were still present at the vitreoretinal interface. This indicates that the effect of microplasmin continues beyond 24 hours and stands in striking contrast to the rapid inactivation of plasmin in the blood by its natural antagonist alpha-2-antiplasmin. One reason for the longevity of microplasmin activity may be that alpha-2-antiplasmin is saturated by another substrate, or that microplasmin has a different affinity for the antiplasmin antagonist compared to plasmin. Another possible reason could be that pathways downstream of microplasmin (for example, activation of collagenases or matrix metalloproteinases) remain active after microplasmin is inactivated by alpha-2-antiplasmin.

The cytoarchitecture of the retina of microplasmin-treated eyes was unchanged compared to control eyes. In ultrastructural terms, there was no difference in the retinal anatomy between microplasmin-treated eyes and control eyes. The ILM and the retina were well preserved in all specimens. Additionally we did not observe any signs of an inflammatory reaction following microplasmin injection. Specifically, electron microscopy and laser confocal microscopy did not show any evidence of inflammatory cellular infiltration of the retina.

In the feline model, retinal detachment produces a significant proliferation of Müller cells and a massive upregulation of intermediate filament proteins in their cytoplasm, such as glial fibrillic acidic protein (GFAP) and vimentin. This Müller cell response is widely known as gliosis, and is supposed to play a key role in the complex cellular responses of the retina to detachment. In the normal retina, Müller cells appear quiescent and express very small amounts of GFAP and vimentin. However, even vitrectomy without inducing retinal detachment has been shown to cause upregulation of GFAP. Recent work by our group demonstrated marked upregulation of intermediate filament proteins following attempted peeling of the ILM in cat eyes (unpublished data). These data point to the high reactivity of Müller cells to any form of surgical trauma.

In the present study, we did not observe any change of Müller cell reactivity following induction of PVD by microplasmin. Moreover, there was no difference between treated eyes and control eyes with respect to any antibody applied. The quiescent state of Müller cells at any time point of the study in association with the unchanged ultrastructure and immunoreactivity of the retina provides experimental evidence pointing to the safety of microplasmin in inducing PVD.

In conclusion, these studies show that microplasmin is effective in inducing PVD in vivo. In addition, these studies indicate that microplasmin appears safe in that no retinal alterations were observed at the ultrastructural level.

EXAMPLE 8

Evaluation of the Effects of Microplasmin on Porcine Vitreous by Use of Dynamic Light Scattering This study was conducted to evaluate the effects of microplasmin (µPli) to characterize the biophysical effects of µPli on fresh, post-mortem porcine vitreous in vitro and in-situ using the non-invasive technique of dynamic light scattering (DLS). DLS provides information about the dynamics of particles and macromolecules in solutions and suspensions by measuring time fluctuations in the intensity of the scattered light.

In a DLS experiment, a constantly fluctuating speckle pattern is seen in the far field when light passes through an ensemble of small particles suspended in a fluid (see, Chu B., *Laser light scattering: Basic prinicples and practice*, Academic Press, New York, 1991). This speckle pattern is the result of interference in the light paths and it fluctuates as the particles in the scattering medium perform random movements on a time scale of $\geq 1$ µsec due to the collisions between themselves and the fluid molecules (Brownian motion). In the absence of particle-particle interactions (dilute dispersions) light scattered from small particles fluctuates rapidly while light scattered from large particles fluctuates more slowly.

Figure 11:
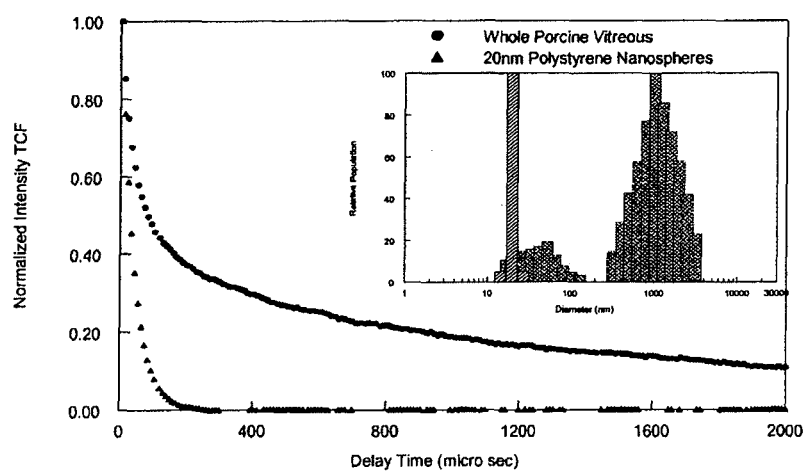
FIG. 11 presents a time correlation function (TCF) of whole porcine vitreous as compared to a solution of 20 nm polystyrene nanospheres. In the vitreous there are two-components to the curve. The early (fast) component is due to the presence of hyaluronan (HA) that is freely diffusible and exhibits considerable molecular (Brownian) motion. The late (slow) component is due to collagen, which is larger and diffuses less freely (stiffer), resulting in slower Brownian movement. In contrast, the solution of polystyrene nanospheres has only one component (monodisperse) that is very fast because of the small size of the nanospeheres and their perfectly spherical structure allowing for very rapid movements in the solution.

The DLS apparatus built for our studies provides dynamic information such as diffusion coefficient, size, scattered intensity, and polydispersity (measure of heterogeneity). In general, an increase in particle sizes (from nanometers to a few microns) and an increase in the number or density of these particles result in an increase in scattered light intensity. Polydispersity is a measure of the number of distinct groups of species with different size(s). In a DLS measurement up to three groups differing in size can be identified since they diffuse at different time scales (small particles move faster and larger slower). Therefore, a change in scattered light intensity and polydispersity can complement the particle size data. If after pharmacologic intervention vitreous particle sizes decrease and scattered intensity increases, then there is probably an increased number of smaller size molecular species in the solution, either due to breakdown of larger molecular species, and/or, as in the case of these experiments, an influx of 20 nm polystyrene nanospheres that were previously excluded by the inherent vitreous structure. If polydispersity decreases, then the most likely explanation is that there is increased homogeneity in the population of molecular species in the sample, again indicative of the influx of 20 nm polystyrene nanospheres that were previously excluded. The most attractive features of DLS are that it is non-invasive and quantitative, works effectively for particle sizes ranging from a few nm to few um, requires small samples volume, and works reasonably well for polydisperse or multiple size (up to 2-3 component) dispersions. The data presented herein was analyzed using the cumulant and exponential size distribution routines obtained from Brookhaven Instruments, NY. These schemes have been reviewed by Stock and Ray (Stock R. S. and Ray W. H., *J. Polym. Sci.* 23:1393, 1985). As an example, FIG. 11 shows a typical DLS measurement in terms of a time autocorrelation function or TCF for the whole porcine vitreous (polydisperse system) and a solution of polystyrene nanospheres of 20 nm diameter (monodisperse system).

Materials and Methods (a) Fabrication of DLS Apparatus for Vitreous Studies

A new compact DLS fiber-optic probe (U.S. Pat. No. 5,973,779) was fabricated for the vitreous studies described herein. It comprises of a pair of 0.25 pitch Selfoc GRIN lenses, and it has a penetration depth of ~16 mm and a scattering angle of 160°. A fiber optic probe comprising two monomode optical fibers and two GRIN lenses provides a compact and remote means of studying the dynamic characteristics of the macromolecules in the eye. Two monomode optical fibers, each housed in a stainless steel ferrule, are mounted into a separate stainless steel housing. An air gap is intentionally left between the fiber housing and the lens housing in order to produce a tightly focused spot in the scattering volume. The two optical fibers in their housings are aligned and fixed into position off-axis with the micro lens. The two housings are placed inside a third (outer) housing made of stainless steel, and the back end of the housing is covered with a heat-shrink tubing. The two free ends of the optical fibers were terminated with FC/PC-type male connectors for easy mating with the laser and photo-detector module.

The experimental set up's main components consist of a DLS compact fiber optic probe (described above), a computer (Gateway PC 500S) containing a digital correlator card (BI-9000 Brookhaven Instruments NY), and a 635 nm wavelength 1 mW solid-state laser (OZ Optics, Canada), and an avalanche photo diode detector (Perkin Elmer, Canada). The probe is mounted on an optical assembly connected through translational stages controlled manually to access and direct the probe to a desired location in the eye.

Each temporal autocorrelation function (TCF) took 20 seconds to collect (except for the filtered cuvette studies which took 1 minute). The delay time of 5 microseconds was kept constant for all the measurements. Prior to starting the vitreous study, the instrument was thoroughly tested for its stability, reliability, and reproducibility by using aqueous dispersions of polystyrene standards (latex nanospheres of 20 nm diameter).

(b) Dynamic Light Scattering of Vitreous and Viscosity Issues

DLS is able to non-invasively provide objective quantification of the average diameter of particles suspended in a solution, in this case the vitreous. To calculate particle sizes accurately it is necessary to either know, or assume the viscosity of the solvent. As previously mentioned, it is not presently possible to accurately measure the viscosity of a non-Newtonian fluid, so assumptions must be made. Given that vitreous is approximately 99% water, it is reasonable to ascribe the viscosity of water to the vitreous. To test the validity of this assumption, DLS measurements were made on whole vitreous gel, the sub-fraction of vitreous that did not pass through a strainer (gel), the sub-fraction of vitreous that did pass through the strainer (non-gel), and the sub-fraction of vitreous that passed through a 0.22 μm Millipore filter (liquid vitreous). These studies were done in optical cuvettes and diffusing 20 nm polystyrene nanospheres were added as a tracer with a known diameter that is highly uniform. DLS measurements in whole vitreous and all the different sub-fractions yielded similar results indicating the vitreous microviscosity is indeed very close to that of pure water. Microviscosity in vitreous refers to the viscosity of trapped water in which the hyaluronan (HA) molecules and collagen bundles are suspended. The Brownian motion of HA molecules are much faster than the collagen bundles which are fairly large in size compared to HA molecules. In the DLS spectra, HA molecular information is embedded at faster (short) delay times and the collagen at slower (longer) delay times. The derived information is shown in the particle size distribution(s).

(c) Reagents

All solutions were prepared using BSS PLUS® (ALCON Labs, Ft. Worth, Tex.). Microplasmin was used at a concentration of 4 mg/ml stock solution. Polystyrene nanospheres (Bangs Laboratories, Fishers, Ind.) of 20 nm diameter and suspended in doubly distilled de-ionized water were added at a fixed ratio in all samples, assuring a uniform number of nanospheres in all samples.

(d) Open Sky Model

Fresh, unfixed porcine eyes (n=11) underwent dissection of the anterior segment via a pars planar incision and sharp dissection of the lens/iris diaphragm off the anterior vitreous. The dissection was carried as close to the posterior lens capsule as possible, without incising this tissue. The eyes were maintained in a holder with the posterior segment below.

The specimens were treated with controls and μPli at doses of 0.08, 0.125, 0.4, 0.6 and 0.8 mg at room temperature by placing the solutions (300 μl) that contained 60 μL of 20 nm polystyrene nanosphere solution onto the anterior surface of the exposed vitreous body. DLS was performed at a single point along the central optical axis located 1, 2, and 4 mm below the vitreous/air interface. Every 15 minutes a DLS reading was obtained for a duration of 90 to 360 minutes.

(e) Closed Eye Model

A 30 G needle was used to inject 300 μL of experimental and control solutions containing polystyrene nanospheres and μPli at doses of 0.0125, 0.025, 0.05, 0.125, 0.25, 0.5, 0.6, and 0.8 mg via a stab incision at the pars plana of intact porcine eyes (n=39). Eyes were incubated in a holder that maintained the cornea above and the posterior segment below (mimicking the supine position) at 37 degrees Celsius for either 30 or 120 minutes. Prior to placing the eye in the temperature-controlled water bath (at all times avoiding any contact between the specimen and the water) and every 15 minutes thereafter, the eye was rotated about the optical axis for 10-15 seconds. After incubation, the eyes underwent excision of the anterior segment via a pars planar incision. DLS was performed at several points (mean=18.6, s.d.=11.8) along the optical axis and along a horizontal axis (mean=30.8 points, s.d.=18.0) at a depth of 4 mm behind the vitreous/air interface.

Results (a) Molecular Morphology of Porcine Vitreous

DLS measurements of whole (intact) vitreous obtained at multiple points along the optical axis of the eye cup (anterior segment dissected away) demonstrate very similar findings at all points from 1.25 mm to 4.75 mm below the air-vitreous interface. These findings are also similar to those obtained in excised whole vitreous placed into a cuvette, in the residual vitreous retained after straining, and in the sub-fraction of vitreous that passed through the strainer. All showed nearly identical particle size distributions. The group of larger particle sizes (to the right) has an average size of about 1000 nm and represents primarily collagen. The smaller particle size distribution (to the left) primarily represents hyaluronan (HA). This particle size distribution pattern was the same in eyes that received polystyrene nanosphere injection.

(b) Open Sky Model

Figure 12:
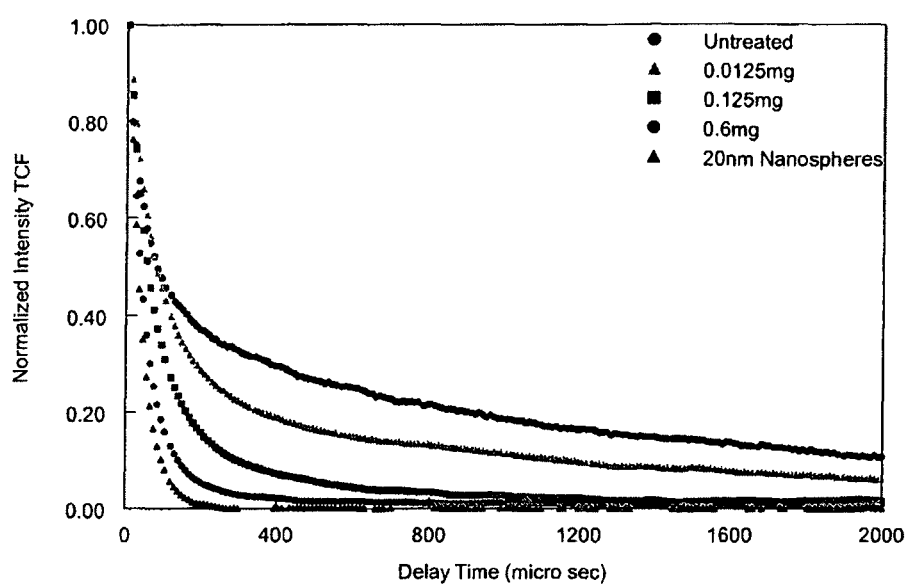
FIG. 12 presents normalized time correlation functions for 5 porcine eyes undergoing microplasmin (µPli) pharmacologic vitreolysis at different doses and a solution of 20 nm polystyrene nanospheres. DLS measurements were made in the optical axis, 4 mm below the air/vitreous interface. In the untreated (vehicle) vitreous there are two-components to the curve. The early (fast) component is due to the presence of hyaluronan (HA) that is freely diffusible and exhibits considerable molecular (Brownian) motion. The late (slow) component is due to collagen, which is larger and diffuses less freely (stiffer), resulting in slower Brownian movement. At the other extreme, the solution of polystyrene nanospheres has only one component (monodisperse) that is very fast because of the small size of the nanospeheres and their perfectly spherical structure allowing for very rapid movements in the solution. With increasing doses of µPli there is a decrease in the slope of the TCF with disappearance of the slow component (larger molecular species) ultimately approaching the TCF of pure 20 nm nanospheres, i.e., all smaller size molecular species.

FIG. 12 shows the TCF's obtained from a point 4 mm below the air/vitreous interface in 5 different porcine eyes and from a solution of 20 nm polystyrene nanospheres, for comparison. It can be seen that with increasing doses of μPli there is a decrease in the slope of the TCF with disappearance of the slow component (larger molecular species) ultimately approaching the TCF of pure 20 nm nanospheres, i.e. all smaller size molecular species.

The results of DLS measurements (n=5) at a depth of 1 mm following treatment with various solutions at room temperature: Placebo and 0.08 mg were essentially the same throughout. With a dose of 0.125 mg there was about a one-third reduction in the overall average particle size after 210 minutes. There was about an 80% reduction in average particle size after 60 minutes and nearly complete reduction of average particle sizes (only 20 nm polystyrene nanospheres were detected) with the 0.6 mg dose.

At a measurement depth of 2 mm behind the air/vitreous interface (n=3) there was about a one-third reduction in the overall average particle size after 180 minutes (data not shown). Incubating the specimen at 37 degrees Celsius and maintaining that temperature during DLS measurements resulted in a 40% reduction in the overall average particle size after treatment with 0.5 mg μPli for 60 minutes in two separate eyes at two different times. The total intensity measurements and the polydispersity measurements for all of these specimens supported and corroborated the particle size determinations.

(c) Closed Eye Model

After a 30-minute incubation at 37 degrees Celsius with μPli doses ranging from 0.0125 to 0.8 mg there were significant changes along both the optical and horizontal axes. In the optical axis there was a seven-fold diminution in the normalized average particle size at the highest dose of 0.8 mg. The dose of 0.125 mg yielded a diminution in the normalized average particle size of about one-third after 30 minutes. The lowest dose of 0.0125 mg did not appear to have any significant effects. Across the entire range of doses the diminution in particle size was inversely proportional to the dose of μPli (coefficient of correlation=0.93). The data was fitted to a linear (straight-line) fitting routine. The normalized total intensity and polydispersity plots further support the reliability of this data. The particle size distributions demonstrate a significant shift to the left in the distribution of particle sizes with increasing doses of μPli. This suggests that μPli is effective in significantly weakening and breaking various chemical bonds and lysing vitreous macromolecular structure. Similar changes were detected along the horizontal axis.

There were also significant changes after a 2-hour incubation at 37 degrees Celsius with μPli doses ranging from 0.0125 to 0.6 mg. At the highest dose there was an 87.5% decrease in the normalized average particle size measured along the optical axis. Normalized scattering intensity and normalized polydispersity plots corroborate this data. The particle size distributions showed a shift to the left with increasing doses, attaining significant proportions with the higher doses. DLS measurements along a horizontal axis at a depth of 4 mm showed similar results, with about an 85% diminution in the normalized average particle sizes and supportive findings on normalized scattering intensity and polydispersity plots.

Comparison of the results at 30 minutes and at 2 hours demonstrates a more extensive degree of particle size breakdown with longer incubation. Consider that at a dose of 0.6 mg the normalized average particle diameter was about 20% in the 30-minute incubation and about 10% in the 2-hour incubation. Thus, there was about a two-fold greater decrease in particle size with longer incubation.

The primary parameter that derives from the DLS measurements is the diffusion coefficient. A change in the diffusion coefficient indicates a change in the vitreous macromolecular structure in response to μPli treatment. With increasing μPli doses there is an increase in the diffusion coefficient of the vitreous. Across the range of μPli doses, diffusion coefficients were directly proportional to μPli dose. Thus, with increasing μPli dose there were decreasing diffusion coefficients and, similar to particle size determinations, this correlation was statistically significant (r=0.93).

Discussion

In this experiment DLS was used to non-invasively assess molecular structure in vitreous by measuring particle sizes, scattering intensity, and polydispersity. The results showed that there are similar DLS profiles in various locations within whole vitreous. The most pronounced effects of microplasmin were upon whole vitreous incubated at 37 degrees C. for 30 min, especially at higher doses. There was a substantial diminution in normalized average particle size and a statistically significant dose-response relation was established. This suggests that μPli would be useful as an adjunct for vitreoretinal surgery, since a 30 minute time frame is reasonable for a drug effect that does not interfere with current surgical practices. In conjunction with the data in the previous Examples suggesting that μPli induces dehiscence at the vitreo-retinal interface, this drug appears to achieve the two desired components for pharmacologic vitreolysis: posterior vitreous detachment and a breakdown in vitreous macromolecules with consequent increases in vitreous diffusion coefficients and ultimately liquefaction.

EXAMPLE 9

Microplasmin as an Adjunct to Surgical Vitrectomy

A patient presenting vitreoretinal disease in which surgical vitrectomy is indicated is treated with an injection of microplasmin prior to the surgical vitrectomy procedure. The patient is to receive a full ophthalmic examination to establish a baseline of ocular health. The ophthalmic examination includes indirect ophthalmoscopy, slit-lamp biomicroscopy, peripheral retinal examination, intraocular pressure measurements, visual acuity (unaided and best corrected) symptomatology, fundus photography, fluorescein angiography, electroretinography and A-scan measurements.

Either up to 30 minutes or up to 1 day prior to the start of vitrectomy, the eye to be treated is injected with 0.025 to 0.125 mg of microplasmin in 0.2 ml of the intraocular irrigating solution, BSS PLUS® or other irrigating solution to promote the liquefaction of the vitreous and/or induce posterior vitreous detachment.

By promoting liquefaction of the vitreous and/or posterior vitreous detachment, the surgical vitrectomy may be made quicker and easier with less iatrogenic retinal trauma and risk of surgical complications. Allowing for more complete removal of vitreous may also lessen the risk of post-operative complications such as proliferative vitreoretinopathy.

EXAMPLE 10

Treatment of Diabetic Retinopathy with Microplasmin

In this Example, a diabetic patient manifesting diabetic retinopathy is treated by the intravitreal injection of microplasmin.

The diabetic patient is to receive a full ophthalmic examination to establish a baseline of ocular health. The ophthalmic examination includes indirect ophthalmoscopy, slit-lamp biomicroscopy, peripheral retinal examination, intraocular pressure measurements, visual acuity (unaided and best corrected) symptomatology, fundus photography, fluorescein angiography, electroretinography and A-scan measurements.

Following the preliminary examination, an intravitreal injection of microplasmin is given to the patient's affected eye. If both eyes are affected, they may be treated separately. The eye to be treated is injected with a dose ranging from 0.005 mg to 0.125 mg of microplasmin in 0.05 to 0.2 ml of BSS PLUS® or other irrigating solution intravitreally to promote the liquefaction of the vitreous.

After treatment, the patients' eyes are to be examined periodically. The extent of diabetic retinopathy presented by the patient is continuously monitored through periodic retinal examinations and fluorescein angiograms to monitor the extent of venous beading, IRMA, retinal ischemia, traction retinal detachment, vitreous hemorrhage, need for vitrectomy, or other complications of diabetic retinopathy.

EXAMPLE 11

Effect of Microplasmin Compared to Plasmin on Speed of Fluorescein Diffusion in Post-mortem Pig Eyes Microplasmin is approximately one-third the molecular weight of full-length plasmin. Due to its smaller size, microplasmin is expected to diffuse more rapidly in the vitreous than plasmin (Xu, J. et al., cited supra). More rapid diffusion would be expected to lead to a more rapid pharmacologic effect. The present study was performed in order to confirm both that microplasmin diffuses more rapidly than plasmin, and that microplasmin is able to alter the vitreous gel.

Methods

Freshly isolated porcine eyes obtained from the slaughterhouse were used. In the first experiment, one eye was injected with microplasmin (0.125 mg) and the fellow eye with vehicle control (BSS-PLUS®). After maintaining both eyes at room temperature for 2 hours, both eyes were then injected with fluorescein and incubated an additional 30 minutes. Photographs were taken at time 0, 10, 20, and 30 minutes.

In the second experiment, eyes were injected with microplasmin 0.125 mg (N=2) or plasmin 1U (supplied by Sigma, N=2), and incubated at 37 degrees Celsius for 2 hours. All 4 eyes were then injected with fluorescein and incubated for an additional 30 minutes, with photographs taken at time 0, 10, 20, and 30 minutes.

Results

In the first experiment, in the control eye virtually no fluorescein diffusion within the vitreous was observed (data not shown). However, in the microplasmin-treated eye clear fluorescein diffusion was observed (data not shown).

Figure 13:
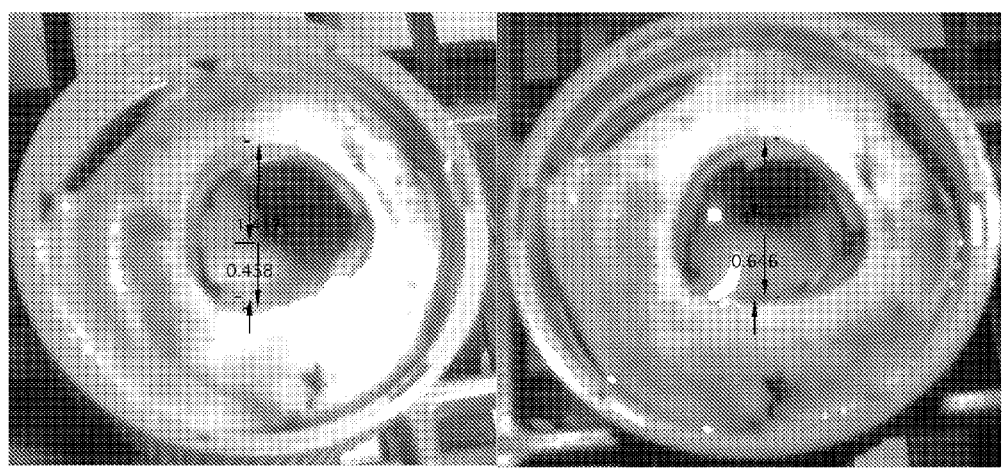
FIG. 13 presents representative photographs of porcine eyes after injection of microplasmin and fluorescein. Both images are of the same eye, with the right image captured 20 minutes after the left image, demonstrating fluorescein diffusion in the vitreous.
Figure 14:
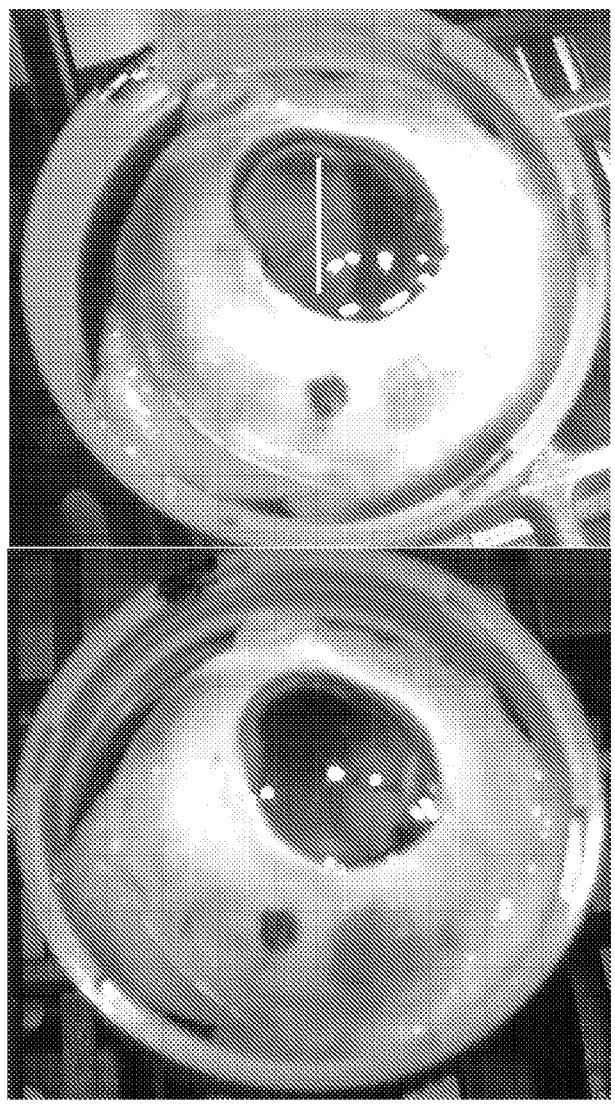
FIG. 14 presents representative photographs of porcine eyes after injection of plasmin and fluorescein. Both images are of the same eye, with the bottom image captured 20 minutes after the top image, demonstrating fluorescein diffusion in the vitreous to a lesser degree than that seen with microplasmin-treated eyes (FIG. 13).

In the second experiment, microplasmin-treated eyes had fluorescein diffusion of 14% and 16%, respectively, over 20 minutes (FIG. 13), while the plasmin-treated eye had fluorescein diffusion of less than 10% (FIG. 14).

Discussion

Microplasmin demonstrated a clear facilitation of fluorescein diffusion compared to vehicle control. Furthermore, as predicted based on molecular weight of microplasmin, this fluorescein diffusion was of a greater extent than that observed with full-length plasmin administration. These findings support the theoretical prediction that microplasmin diffuses more rapidly than plasmin. These findings may have clinical benefit, in allowing for more rapid pharmacologic effect.

---

The invention claimed is:

1. A method of treating a vitreoretinal disease or disorder, or of treating a complication of a vitreoretinal disease or disorder, of an eye of a subject, comprising contacting the vitreous in the eye of the subject with an effective amount of a microplasmin and with an effective amount of a second agent, wherein said second agent is selected from the group consisting of hyaluronidase, chondroitinase ABC, chondroitinase AC, chondroitinase B, chondroitin 4-sulfatase, chondroitin 6-sulfatase, β-glucuronidase, collagenase, dispase, RGD containing peptides, echistatin, falvoridin, anti-integrin antibody, P2Y receptor antagonists, urea, hydroxyurea, thiourea, anti-angiogenic agents, vascular endothelial growth factor (VEGF) inhibitors, placental growth factor (PlGF) inhibitors, and any combinations thereof, thereby treating the vitreoretinal disease or disorder, or the complication of the vitreoretinal disease or disorder, of the eye of the subject.

2. The method according to claim 1 wherein said vitreous is contacted with the second agent prior to, at the same time as, or after being contacted with said microplasmin.

3. The method according to claim 1 wherein said VEGF inhibitor is an anti-VEGF antibody, a VEGF-aptamer, or a soluble VEGF receptor.

4. The method according to claim 1 wherein said PlGF inhibitor is an anti-PlGF antibody, a PlGF-aptamer, or a soluble VEGF receptor.

5. The method according to claim 1 wherein said vitreoretinal disease or disorder is selected from the group consisting of retinal detachment, retinal tear, retinal neovascularization, vitreous hemorrhage, diabetic vitreous hemorrhage, proliferative diabetic retinopathy, non-proliferative diabetic retinopathy, macular pucker, macular exudates, fibrin deposition, retinal vein occlusion, retinal artery occlusion, subretinal hemorrhage, amblyopia, endophthalmitis, retinopathy of prematurity, glaucoma, retinitis pigmentosa, and any combination thereof.

6. The method according to claim 1 wherein said vitreoretinal disease or disorder is macular edema.

7. The method according to claim 6 wherein said macular edema is cystoid macular edema.

8. The method according to claim 1 wherein said vitreoretinal disease or disorder is age-related macular degeneration.

9. The method according to claim 1 wherein said vitreoretinal disease or disorder is macular hole.

10. The method according to claim 9 wherein said macular hole is selected from the group consisting of impending macular hole, full-thickness macular hole, idiopathic macular hole and traumatic macular hole.

11. The method according to claim 1 wherein said vitreoretinal disease or disorder is vitreomacular traction.

12. The method according to claim 1 wherein said vitreoretinal disease or disorder is incomplete posterior vitreous detachment.

13. The method according to claim 1 wherein said vitreoretinal disease or disorder is associated with vitreous contraction.

14. The method according to claim 1 wherein said microplasmin is selected from the group consisting of recombinant microplasmin, stabilized microplasmin, and stabilized, recombinant microplasmin.

15. The method according to claim 14 wherein said microplasmin is stabilized by contacting with a stabilizing agent.

16. The method according to claim 15 wherein said stabilizing agent is selected from the group consisting of tranexamic acid, hexanoic acid, lysine, serine, threonine, methionine, glutamine, alanine, glycine, isoleucine, valine, alanine aspartic acid, polyhydric alcohol, a pharmaceutically acceptable carbohydrate, glucosamine, thiamine, niacinamide, an acidic buffer, a salt, and any combination thereof.

17. The method according to claim 16 wherein said acidic buffer is comprising acetic acid, benzoic acid, carboxylic acid, citric acid, hydrochloric acid, lactic acid, malic acid or tartaric acid.

18. The method according to claim 16 wherein said salt is calcium chloride, magnesium chloride, potassium chloride or sodium chloride.

19. The method according to claim 14 wherein said microplasmin is purified in the presence of a stabilizing agent.

20. The method according to claim 19 wherein said stabilizing agent is selected from the group consisting of tranexamic acid, hexanoic acid, lysine, serine, threonine, methionine, glutamine, alanine, glycine, isoleucine, valine, alanine aspartic acid, polyhydric alcohol, a pharmaceutically acceptable carbohydrate, glucosamine, thiamine, niacinamide, an acidic buffer, a salt, and any combination thereof.

21. The method according to claim 20 wherein said acidic buffer is comprising acetic acid, benzoic acid, carboxylic acid, citric acid, hydrochloric acid, lactic acid, malic acid or tartaric acid.

22. The method according to claim 20 wherein said salt is calcium chloride, magnesium chloride, potassium chloride or sodium chloride.

23. The method according to claim 1 wherein the step of contacting the vitreous with the microplasmin comprises injecting the microplasmin into the vitreous or the aqueous humor.

24. The method according to claim 23 wherein the microplasmin is a human microplasmin.

25. The method according to claim 1 wherein the subject is a human.

26. The method according to claim 1 wherein the method is performed in the absence of mechanical vitrectomy.

27. The method according to claim 1 wherein the method is performed as an adjunct to mechanical vitrectomy.

28. The method according to claim 1 wherein the effective amount of the microplasmin is in the range of 0.005 mg to 0.2 mg per eye.

29. The method according to claim 1 wherein the microplasmin consists of a double chain polypeptide of amino acids 543 to 791 of SEQ ID NO:10 wherein the peptide bond between Arg561 and Val 562 is cleaved by a plasminogen activator.

30. The method according to claim 1 wherein the microplasmin is an activated microplasminogen wherein said microplasminogen is encoded by SEQ ID NO:3.

31. The method according to claim 1 wherein the microplasmin is produced by recombinant expression in a yeast.

32. The method according to claim 31 wherein said yeast is *Pichia pastoris*.

* * * * *

UNITED STATES PATENT AND TRADEMARK OFFICE
CERTIFICATE OF CORRECTION

PATENT NO. : 8,834,869 B2
APPLICATION NO. : 13/689025
DATED : September 16, 2014
INVENTOR(S) : Steve Pakola et al.

Page 1 of 1

It is certified that error appears in the above-identified patent and that said Letters Patent is hereby corrected as shown below:

In the specification
    At column 4, line 55, please delete "compositions";
    At column 6, line 59, please delete "nanospeheres" and insert --nanospheres--;
    At column 7, line 8, please delete "nanospeheres" and insert --nanospheres--;
    At column 15, Table 1, line starting with "554-777", please delete "5544-781" and insert --554-781--;
    At column 27, line 8, please insert --(SEQ ID NO:11)-- after "GRGDS", and insert --(SEQ ID NO:12)-- after "GRGDTP";
    At column 29, line 39, please insert --(SEQ ID NO:13)-- after "(6x His) tag";
    At column 29, line 52, please insert --(SEQ ID NO:14)-- after "Ala";
    At column 30, line 30, please delete "of human plasminogen";
    At column 30, line 31, please insert --of human plasminogen (SEQ ID NO:10)-- after "Pro-Ser-Phe-Asp-Cys)";
    At column 30, line 33, please insert --(SEQ ID NO:15)-- after "(Leu-Glu-Lys-Arg)";
    At column 31, line 23, please delete "of plasminogen";
    At column 31, line 23, please insert --of plasminogen (SEQ ID NO:10)-- after "Pro-Val-Val-Leu-Leu-Pro)";
    At column 31, line 26, please insert --(SEQ ID NO:15)-- after "(Leu-Glu-Lys-Arg)";
    At column 31, line 31, please delete "of human plasminogen";
    At column 31, line 32, please insert --of human plasminogen (SEQ ID NO:10)-- after "(Glu-Trp-Val-Leu-Thr-Ala-His-Cys)";
    At column 37, line 63, please delete 2nd "contrasted"; and
    At column 42, line 66, please delete "um" and insert --µm--.

Signed and Sealed this
Third Day of May, 2016

Michelle K. Lee
*Director of the United States Patent and Trademark Office*